US007985745B2

(12) United States Patent
Cowart et al.

(10) Patent No.: US 7,985,745 B2
(45) Date of Patent: Jul. 26, 2011

(54) METHOD FOR PAIN TREATMENT

(75) Inventors: Marlon D. Cowart, Round Lake Beach, IL (US); Robert J. Altenbach, Chicago, IL (US); Huaqing Liu, Buffalo Grove, IL (US); Irene Drizin, Wadsworth, IL (US); Neil Wishart, Jefferson, MA (US); David J. Babinski, Dallas, TX (US); Robert J. Gregg, Libertyville, IL (US); Arthur A. Hancock, Libertyville, IL (US); Kathryn J. Hancock, legal representative, Libertyville, IL (US); Timothy A. Esbenshade, Schaumburg, IL (US); Gin C. Hsieh, Long Grove, IL (US); Jorge D. Brioni, Vernon Hills, IL (US); Marie P. Honore, Evanston, IL (US); Lawrence A. Black, Libertyville, IL (US); Chen Zhao, Libertyville, IL (US); Brian D. Wakefield, Evanston, IL (US)

(73) Assignee: Abbott Laboratories, Abbott Park, IL (US)

(*) Notice: Subject to any disclaimer, the term of this patent is extended or adjusted under 35 U.S.C. 154(b) by 346 days.

(21) Appl. No.: 11/863,925

(22) Filed: Sep. 28, 2007

(65) Prior Publication Data

US 2008/0194538 A1     Aug. 14, 2008

Related U.S. Application Data

(60) Provisional application No. 60/848,954, filed on Oct. 2, 2006.

(51) Int. Cl.
| A61K 31/395 | (2006.01) |
| A61K 31/495 | (2006.01) |
| A61K 31/498 | (2006.01) |
| A61K 31/502 | (2006.01) |
| A61P 25/00 | (2006.01) |
| A61P 25/02 | (2006.01) |
| A61P 19/02 | (2006.01) |

(52) U.S. Cl. ............... 514/210.21; 514/252.14; 514/267
(58) Field of Classification Search ............ 514/210.21, 514/252.14, 267
See application file for complete search history.

(56) References Cited

U.S. PATENT DOCUMENTS

| 3,755,583 | A | 8/1973 | De Angelis et al. |
| 5,071,999 | A | 12/1991 | Schenke et al. |
| 6,204,017 | B1 | 3/2001 | Behan et al. |
| 6,803,362 | B2 | 10/2004 | Carruthers et al. |
| 2003/0207893 | A1 | 11/2003 | Carruthers et al. |
| 2004/0048878 | A1 | 3/2004 | Cai et al. |
| 2005/0070527 | A1 | 3/2005 | Edwards et al. |
| 2005/0070550 | A1 | 3/2005 | Arienti et al. |
| 2005/0101602 | A1 | 5/2005 | Basha et al. |
| 2006/0025614 | A1 | 2/2006 | Carroll et al. |
| 2006/0100194 | A1 | 5/2006 | Blackburn et al. |
| 2006/0111416 | A1 | 5/2006 | Lane et al. |
| 2007/0149541 | A1 | 6/2007 | Buzard et al. |
| 2007/0185075 | A1 | 8/2007 | Bell et al. |
| 2007/0185131 | A1 | 8/2007 | Cai et al. |
| 2008/0188452 | A1 | 8/2008 | Altenbach et al. |

FOREIGN PATENT DOCUMENTS

| EP | 1767537 | 3/2007 |
| JP | 2221262 A | 9/1990 |
| JP | 1994220059 | 1/1993 |
| WO | WO9507893 A1 | 3/1995 |
| WO | 0162233 | 8/2001 |
| WO | 02/072548 | 9/2002 |
| WO | 02072548 | 9/2002 |
| WO | 03020907 | 3/2003 |
| WO | 2004022061 | 3/2004 |
| WO | 2004066960 | 8/2004 |
| WO | 2005007648 | 1/2005 |
| WO | 2005/014556 | 2/2005 |
| WO | 2005014556 | 2/2005 |
| WO | 2005014579 | 2/2005 |
| WO | WO2005037825 A2 | 4/2005 |
| WO | WO2005042500 A1 | 5/2005 |
| WO | 2005/054239 | 6/2005 |
| WO | 2005054239 | 6/2005 |
| WO | 2005092066 | 10/2005 |
| WO | WO2006041773 A2 | 4/2006 |
| WO | 2006/050965 | 5/2006 |
| WO | 2006050965 | 5/2006 |
| WO | WO2006050965 A1 | 5/2006 |
| WO | 2007090852 | 2/2007 |
| WO | 2007072163 | 6/2007 |
| WO | 2007/090852 | 8/2007 |
| WO | 2007090853 | 8/2007 |
| WO | 2007090854 | 8/2007 |
| WO | WO2007090852 A1 | 8/2007 |
| WO | 2008031556 | 3/2008 |

OTHER PUBLICATIONS

Adami, M., Anti-inflammatory, Analgesic and Gastroprotective Effects of the Histamine H-4 Receptor Antagonist May 2005 Poster Session: Histamine Receptors, p. 47.
Akdis,, Cezmi and Simons, Estelle, "Histamine receptors are hot in immunopharmacology", European Journal of Pharmacology, vol. 533; pp. 69-76; (2006).
Collins, Susanne and Chessell, Iain, "Emerging therapies for neuropathic pain", Expert Opin. Emerging Drugs. vol. 10(1); pp. 95-108, (2005). Coruzzi, Gabriella, et al., "Anti-inflammatory and antinociceptive effects of the selective histamine $H_4$-receptor antagonists JNJ7777120 and VUF6002 in a rat model of carrageenan-induced acute inflammation", European Journal of Pharmacology. vol. 563, pp. 240-244 (2007).
de Esch, Iwan, et al. "The histamine $H_4$ receptor as a new therapeutic target for inflammation", Trends in Pharmacological Sciences. vol. 26 No. 9; pp. 462-469 (2005).
Dworkin, Robert H., "An overview of Neuropathic Pain: Syndromes, Symptoms, Sign, and Several Mechanisms", Clinical Journal of Pain. vol. 18: 343-349 (2002).
Joshi, Shailen and Honore, Prisca, "Animal models of pain for drug discovery", Expert Opin. Drug Discov, vol. 1(4); pp. 323-334, (2006).

(Continued)

*Primary Examiner* — Sreeni Padmanabhan
*Assistant Examiner* — Sahar Javanmard
(74) *Attorney, Agent, or Firm* — Nancy J. Gettel; Portia Chen; Gabryleda Ferrari-Dileo

(57) ABSTRACT

This invention discloses a method of treating pain by administering histamine $H_4$ receptor ligands and compositions comprising the same.

17 Claims, No Drawings

OTHER PUBLICATIONS

Smith, Peter A.. "Neuropathic Pain: Drug Targets for Current and Future Interventions" Drugs News Perspect 17(1), pp. 5-17; (2004).
Zhang, Mai et al.; "The histamine $H_4$ receptor in autoimmune disease", Expert Opin. Investig. Drugs. vol. 15(11); pp. 1443-1452 (2006).
Bennett and Xie, "A peripheral mononeuropathy in rat that produces disorders of pain sensation like those seen in man", Pain 33: 87-107 (1988).
Chaplan et al., "Quantitative assessment of tactile allodynia in the rat paw", J. Neuroscience Methods, 53: 55-63 (1994).
Coge, et al., "Structure and Expression of the Human Histamine H4-Receptor Gene", Biochemical and Biophysical Research Communications, 284: 301-309 (2001).
Collins, et al., "Emerging therapies for neuropathic pain", Expert Opinion on Emerging Drugs, 10(1): 95-108 (2005).
De Esch, et al., "The histamine H4 Receptor as a new therapeutic target for inflammation", Trends in Pharmacological Science, 26: 462-469 (2005).
Dixon, "Efficient Analysis of Experimental Observations", Annual Rev. Pharmacol. Toxicol., 20: 441-462 (1980).
Dray, et al., "Pharmacology of chronic pain", Trends in Pharmacological Sciences, 15(6): 190-197 (1994).
Dworkin, R., "An Overview of Neuropathic Pain: Syndromes, Symptons, Signs, and Several Mechanisms", Clinical Journal of Pain, 18(6): 343-349 (2002).
Esbenshade, et al., "Pharmacological and behavioral properties of A-349821, a selective and potent human histamine H3 receptor antagonist", Biochemical Pharmacology, 68: 933-945 (2004).
Furniss, et al., "Vogel's Textbook of Practical Organic Chemistry", 5th edition (1989), Longman Scientific & Technical, Essex CM20 2JE, England (Table of Contents).
Hartwig, "Transition Metal Catalyzed Synthesis of Arylamines and Aryl Ethers from Aryl Halides and Triflates: Scope and Mechanism", Angew. Chem. Int. Ed., 37:2046-2067 (1998).
Hartwig, et al. "Room-Temperature Palladium-Catalyzed Amination of Aryl Bromides and Chloride and Extended Scope of Aromatic C-N Bond Formation with a Commercial Ligand", J. Org. Chem., 64(15):5575-5580 (1999).
Honore, et al., "Interleukin-1 alpha beta gene-deficient mice show reduced nociceptive sensitivity in models of inflammatory and neuropathic pain but not post-operative pain", Behavioural Brain Research, 167: 355-364 (2006).
Hough, "Genomics Meets Histamine Receptors: New Subtypes, New Receptors", Molecular Pharmacology, 59: 415-419 (2001).
Higuchi et al., Pro-drugs as Novel Delivery Systems, V. 14 of the A.C.S. Symposium Series (Table of Contents), (1975).
Igaz, et al., Histamine: Biology and Medical Aspects, 89-96 (2004).
IUPAC 1974 Recommendations for Section E, Fundamental Stereochemistry, in Pure Appl. Chem., 45: 13-30 (1976).
Jablonowski, et al., "The First Potent and Selective Non-Imidazole Human Histamine H4 Receptor Antagonists", Journal of Medicinal Chemistry, 46: 3957-3960 (2003).
Joshi et al., "Animal models of pain for drug discovery", Expert Opinion in Drug Discovery, 1: 323-334 (2004).
Joshi, et al., "Involvement of the TTX-resistant sodium channel Nav 1.8 in inflammatory and neuropathic, but not post-operative, pain states", Pain, 123: 75-82 (2006).
Kim, et al., "An experimental model for peripheral neuropathy produced by segmental spinal nerve ligation in the rat", Pain, 50: 355-363 (1992).
Kiyomori et al., "An Efficient Copper-Catalyzed Coupling of Aryl Halides with Imidazoles", Tet. Lett., 40:2657-2640 (1999).
Klapars et al., "A General and Efficient Copper Catalyst for the Amidation of Aryl Halides and the N-Arylation of Nitrogen Heterocycles", J. Amer. Chem. Soc., 123:7727-7729 (2001).
Krueger, et al., "G Protein-Dependent Pharmacology of Histamine H3 Receptor Ligands: Evidence for Heterogeneous Active State Receptor Conformations", Journal of Pharmacology and Experimental Therapeutics, 314: 271-281 (2005).
Kwong et al., "Copper-Catalyst Coupling of Alkylamines and Aryl Iodides: An Efficient System Even in an Air Atmosphere", Org. Lett., 4:581-584 (2002).

Ling, et al., "Histamine H4 receptor mediates eosinophil chemotaxis with cell shape change and adhesion molecule upregulation", British Journal of Pharmacology, 142: 161-171 (2004).
Liu, et al., "Comparison of Human, Mouse, Rat, and Guinea Pig Histamine H4 Receptors Reveals Substantial Pharmacological Species Variation", Journal of Pharmacology and Experimental Therapeutics, 299: 121-130 (2001).
Liu, et al., "Cloning and Pharmacological Characterization of a Fourth Histamine Receptor (H4) Expressed in Bone Marrow", Molecular Pharmacology, 59: 420-426 (2001).
Morse, et al., "Cloning and Characterization of a Novel Human Histamine Receptor", Journal of Pharmacology and Experimental Therapeutics, 296: 1058-1066 (2001).
Nakamura, et al., "Molecular Cloning and Characterization of a new Human Histamine Receptor, HH4R", Biochemical and Biophysical Research Communications, 279: 615-620 (2000).
Nguyen, et al., "Discovery of a Novel Member of the Histamine Receptor Family", Molecular Pharmacology, 59: 427-433 (2001).
Parsons, et al., "Histamine and its receptors", British Journal of Pharmacology, 147: S127-S135 (2006).
Porreca, et al., "Antinociceptive Pharmacology of N-[[4-(4,5-Dihydro-1H-imidazol-2-yl)phenyl]methyl]-2-[2-[[(4-methoxy-2,6-dimethylphenyl)sulfonyl]methylamino]ethoxy]-N-methylacetamide, Fumarate (LF22-0542), a Novel Nonpeptidic Bradykinin B1 Receptor Antagonist", Journal of Pharmacology and Experimental Therapeutics, 318: 195-205 (2006).
Prescott, Ed., Methods in Cell Biology, vol. XIV, Academic Press, New York, N. Y., (1976), p. 33 et seq.
Roche, ed., Bioreversible Carriers in Drug Design, American Pharmaceutical Association and Pergamon Press (1987) Table of Contents.
Smith, et al., "Neuropathic Pain and the Electrophysiology and Pharmacology of Nerve Injury" Drug Development Research, 54(3): 140-153 (2001).
Stark, "Recent advances in histamine H3/H4 receptor ligands", Expert Opinion in Therapeutic Patents, 13: 851-865 (2003).
Sugahara et al., "A Facile Copper-Catalyzed Ullmann Condensation: N-Arylation of Heterocyclic Compounds Containing an -NHCO— Moiety", Chem. Pharm. Bull., 45:719-721 (1997).
Thurmond, et al., "A Potent and Selective Histamine H4 Receptor Antagonist with Anti-Inflammatory Properties", Journal of Pharmacology and Experimental Therapeutics, 309: 404-413 (2004).
Vinik, et al., "Diabetic neuropathies", Medical Clinics of North America, 88(4): 947-999 (2004).
Vogel, G., Drug Discovery and Evaluation, 2nd edition; Springer-Verlag, New York, 702-706 (2002).
Wolfe et al., "Rational Development of Practical Catalysts for Aromatic Carbon-Nitrogen Bond Formation", Acc. Chem. Res., 31:805-818 (1998).
Wolfe et al., "Simple, Efficient Catalyst System for the Palladium-Catalyzed Amination of Aryl Chlorides, Bromides, and Triflates", J. Org. Chem., 65:1158-1174, (2000).
Yang, et al., "Palladium-catalyzed amination of aryl halides and sulfonates", J. Organomet. Chem., 576:125-146 (1999).
Zhu, et al., "Cloning, Expression, and Pharmacological Characterization of a Novel Human Histamine Receptor", Molecular Pharmacology, 59:434-441 (2001).
PCT International Search Report for PCT/US2007/080132, mailed Sep. 12, 2008.
Adamin, et al., Antinflammatory, Analgesic and Gastroprotective Effects of the Novel and Selective Histamine H4-Receptor Antagonist VUF5949, Poster Session: Histamine Receptors.
Akdis, et al., "Histamine Receptors Are Hot in Immunopharmacology," European Journal of Pharmacology, 2006, vol. 533, pp. 69-76.
Bell, et al., "Involvement of Histamine H4 and H1 Receptors in Scratching Induced by Histamine Receptor Agonists in Balb C Mice," British Journal of Pharmacology, 2004, vol. 142, pp. 374-380.
Bennett, et al., "A Peripheral Mononeuropathy in Rat that Produces Disorders of Pain Sensation like those Seen in Man," Pain, 1988, vol. 33 (1), pp. 87-107.
Buckland, et al., "Histamine Induces Cytoskeletal Changes in Human Eosinophils via the H(4) Receptor," British Journal of Pharmacology, 2003, vol. 140, pp. 1117-1127.

Caubere, et al., "Condensations Aryniques D'enolates de Cetones," Bulletin de la Societe Chimique de France, 1974, pp. 1415-1420.

Chan, et al., "Design, Synthesis, and Antifolate Activity of New Analogues of Piritrexim and Other Diaminopyrimidine Dihydrofolate Reductase Inhibitors with Omega-Carboxyalkoxy or Omega-Carboxy-1-Alkynyl Substitution in the Side Chain," Journal of Medicinal Chemistry, 2005, vol. 48 (13), pp. 4420-4431.

Chaplan, et al., "Quantitative Assessment of Tactile Allodynia in the Rat Paw," Journal of Neuroscience Methods, 1994, vol. 53, pp. 55-63.

Cianchi, et al., "The role of Cyclooxygenase-2 in Mediating the Effects of Histamine on Cell Proliferation and Vascular Endothelial Growth Factor Production in Colorectal Cancer," Clinical Cancer Research, 2005, vol. 11 (19), pp. 6807-6815.

Coge, et al., "Structure and Expression of the Human Histamine H4-Receptor Gene," Biochemical and Biophysical Research Communications, 2001, vol. 284 (2), pp. 301-309.

Collins, et al., "Emerging Therapies for Neuropathic Pain," Expert Opinion on Emerging Drugs, 2005, vol. 10 (1), pp. 95-108.

Coruzzi, et al., "Anti-Inflammatory and Antinociceptive Effects of the Selective Histamine H4-Receptor Antagonists JNJ7777120 and VUF6002 in a Rat Model of Carrageenan-Induced Acute Inflammation," European Journal of Pharmacology, 2007, vol. 563 (1-3), pp. 240-244.

Coruzzi, et al., Gastric Effects of the Histamine H4 Receptor Antagonists JN7777120 and VU6002, 2006, XXXVth Annual Meeting, Greece.

Cross, et al., "IUPAC Commission on Nomenclature of Organic Chemistry: Rules for the Nomenclature of Organic Chemistry, Section E: Stereochemistry," Pure and Applied Chemistry, 1976, vol. 45, pp. 13-30.

De Esch, et al., "The Histamine H4 Receptor as a New Therapeutic Target for Inflammation," Trends in Pharmacological Science, 2005, vol. 26 (9), pp. 462-469.

Deshmukh, et al., "Reaction of 2-Butenoic Acid Dianion and Its N-(4Methoxyphenyl)amide with Methoxy-Substituted Arynes," Journal of Organic Chemistry, 1992, vol. 57 (2), pp. 667-670.

Dixon, "Efficient Analysis of Experimental Observations," Annual Review of Pharmacology and Toxicology, 1980, vol. 20, pp. 441-462.

Dray, et al., "Pharmacology of Chronic Pain," Trends in Pharmacological Sciences, 1994, vol. 15 (6), pp. 190-197.

Dunford, et al., "The Histamine H4 Receptor Mediates Allergic Airway Inflammation by Regulating the Activation of CD4+ T cells," the Journal of Immunology, 2006, vol. 176 (11), pp. 7062-7070.

Dworkin, "An Overview of Neuropathic Pain: Syndromes, Symptoms, Signs, and Several Mechanisms," Clinical Journal of Pain, 2002, vol. 18 (6), pp. 343-349.

Esbenshade, et al., "Pharmacological and Behavioral Properties of A-349821, a Selective and Potent Human Histamine H3 Receptor Antagonist," Biochemical Pharmacology, 2004, vol. 68 (5), pp. 933-945.

Fogel, et al., "Influence of H3/H4 Receptor Antagonist Thioperamide on Regional Haemodynamics in Rats with Trinitrobenzene Sulfonic Acid-Induced Colitis 35th Meeting of the European Histamine Research Society in Delphi, Greece," 2006, pp. 32.

Furniss, et al., Vogel's Textbook of Practical Organic Chemistry, 5th Edition, Longman Scientific & Technical, 1989, Table of Contents.

Gutzmer, et al., "Histamine H4 Receptor Stimulation Suppresses Il-12p70 Production and Mediates Chemotaxis in Human Monocyte-derived Dendritic Cells," Journal of Immunology, 2005, vol. 174 (9), pp. 5224-5232.

Hartwig, et al., "Room-Temperature Palladium-Catalyzed Amination of Aryl Bromides and Chloride and Extended Scope of Aromatic C-N Bond Formation with a Commercial Ligand," Journal of Organic Chemistry, 1999, vol. 64 (15), pp. 5575-5580.

Hartwig, et al., "Transition Metal Catalyzed Synthesis of Arylamines and Aryl Ethers from Aryl Halides and Triflates: Scope and Mechanism," Angewandte Chemie International Edition, 1998, 37, pp. 2046-2067.

Higuchi, et al., Pro-drugs as Novels Delivery Systems, vol. 14, ACS Symposium Series, 1975, Table of Contents.

Hirota, et al., "Polycyclic N-Hetero Compounds Synthesis and Anti-Platelet Aggregation Activity of 4-Substituted 5,6-Dihydrobenzo[h]Quinazolines," Heterocycles, 1990, vol. 31 (1), pp. 153-161.

Honore, et al., "Interleukin-1 Alpha Beta Gene-Deficient Mice Show Reduced Nociceptive Sensitivity in Models of Inflammatory and Neuropathic Pain but not Post- Operative Pain," Behavioural Brain Research, 2006, vol. 167 (2), pp. 355-364.

Ikawa, et al., "Histamine H4 Receptor Expression in Human Synovial Cells Obtained from Patients Suffering from Rheumatoid Arthritis," Biological and Pharmaceutical Bulletin, 2005, vol. 28 (10), pp. 2016-2018.

International Search Report for Application No. PCT/US2007/080133, mailed on May 9, 2008, 3 pages.

Jablonowska, et al., Distribution Pattern of Histamine H4 Receptor in Human Synovial Tissue from Patients with Rheumatoid Arthritis, 35th Meeting of the European Histamine Research Society in Delphi, Greece, Presentation 036.

Jantzen, et al., Modern Pharmaceuticals, 1996, pp. 596.

Joshi, et al., "Animal Models of Pain for Drug Discovery," Expert Opinion on Drug Discovery, 2006, vol. 1 (4), pp. 323-334.

Kim, et al., "An Experimental Model for Peripheral Neuropathy Produced by Segmental Spinal Nerve Ligation in the Rat," Pain, 1992, vol. 50 (3), pp. 355-363.

Kiyomori, et al., "An Efficient Copper-Catalyzed Coupling of Aryl Halides with Imidazoles," Tetrahedron Letters, 1999, vol. 40, pp. 2657-2660.

Klapars, et al., "A General and Efficient Copper Catalyst for the Amidation of Aryl Halides and the N-Arylation of Nitrogen Heterocycles," Journal of the American Chemical Society, 2001, vol. 123, pp. 7727-7729.

Krueger, et al., "G Protein-Dependent Pharmacology of Histamine H3 Receptor Ligands: Evidence for Heterogeneous Active State Receptor Conformations," Journal of Pharmacology and Experimental Therapeutics, 2005, vol. 314 (1), pp. 271-281.

Kwong, et al., "Copper-Catalyzed Coupling of Alkylamines and Aryl Iodides: An Efficient System Even in an Air Atmosphere," Organic Letters, 2002, vol. 4, pp. 581-584.

Lazar-Molnar, et al., Biology and Medical Aspects, pp. 89-96, 2004.

Liu, et al., "Cloning and Pharmacological Characterization of a Fourth Histamine Receptor (H4) Expressed in Bone Marrow," Molecular Pharmacology, 2001, vol. 59, pp. 420-426.

Liu, et al., "Comparison of Human, Mouse, Rat, and Guinea Pig Histamine H4 Receptors Reveals Substantial Pharmacological Species Variation," Journal of Pharmacology and Experimental Therapeutics, 2001, vol. 299 (1), pp. 121-130.

Maslinska, et al., Toll-like Receptors (TLRs) and Histamine Receptor H4 in Articular Tissues of Patients with Rheumatoid Arthritis (RA), 34th Meeting of the European Histamine Research Society in Bled, Slovenia, 2005, Poster P-03.

Nargund, et al., "Synthesis of 7-Substituted-4-(3",4", 5"-Trisubstituted-1- Pyrazolyl)Pyrimido-[5,4-c]Cinnolines and Their Anti-Inflammatory Activities," Drug Research, 1994, vol. 44 (2), pp. 156-158.

Nargund, et al., "Synthesis, Inhibition of Albumin Denaturation and Anti-Inflammatoryactivity of4-Arylaminopyrimido[5,4-c]Cinnolines," Revue Roumaine de Chimie, 1997, vol. 42 (11), pp. 1089-1091.

Nguyen, et al., "Discovery of a Novel Member of the Histamine Receptor Family," Molecular Pharmacology, 2001, vol. 59 (3), pp. 427-433.

Oda, et al., "Molecular Cloning of Monkey Histamine H4 Receptor," Journal of Pharmacological Sciences, 2005, vol. 98 (3), pp. 319-322.

Parsons, et al., "Histamine and its Receptors," British Journal of Pharmacology, 2006, vol. 147 Suppl., 1, pp. S127-S135.

Porreca, et al., "Antinociceptive Pharmacology of N-[[4-(4,5-Dihydro-1H-imidazol-2- yl)phenylmethyl]-242-[[(4- methoxy-2,6-dimethylphenyl)sulfonyl]methylaminojethoxyl-Nmethylacetamide, Fumarate (LF22-0542), a Novel Nonpeptidic Bradykinin B1 Receptor Antagonist," Journal of Pharmacology and Experimental Therapeutics, 2006, vol. 318, pp. 195- 205.

Poste, et al., "Lipid Vesicles as Carriers for Introducing Biologically Active Materials into Cells," Methods in Cell Biology, 1976, vol. 14, pp. 33-71.

Roche, Bioreversible Carries in Drug Design Theory and Application, Pergamon Press, 1987, Table of Contents.

Rover, et al., "High-Affinity, Non-Peptide Agonists for the ORL1 (Orphanin FQ/Nociceptin) Receptor," Journal of Medicinal Chemistry, 2000, vol. 43 (7), pp. 1329-1338.

Sambaiah, et al., "Highly Regio— and Stereoselective Cocyclotrimerization and Linear Cotrimerization of 0-Unsaturated Carbonyl Compounds with Alkynes Catalyzed by Nickel Complexes," The Journal of Organic Chemistry, 1999, vol. 64 (10), pp. 3663-3670.

Sasaki, et al. Journal of Heterocyclic Chemistry, 1990, vol. 27 (6), pp. 1771-1776.

Smith, et al., "Neuropathic Pain and the Electrophysiology and Pharmacology of Nerve Injury," Drug Development Research, 2001, vol. 54 (3), pp. 140-153.

Starck, "Recent Advances In Histamine H3/H4 Receptor Ligands," Expert Opinion in Therapeutic Patents, 2003, vol. 13 (6), pp. 851-865.

Sugahara, et al., "A Facile Copper-Catalyzed Ullmann Condensation: N-Arylation of Heterocyclic Compounds Containing an -NHCO- Moiety," Chemical & Pharmaceutical Bulletin, 1997, vol. 45, pp. 719-721.

Theis, et al., "A Ring Expansion Route to Benzo Substituted Medium- and Large-Ring Systems. Synthesis of trans-7,8-Benzocyclododeca-5,7-dien-1-one," Journal of Organic Chemistry, 1977, vol. 42 (2), pp. 280-281.

Thurmond, et al., "A Potent and Selective Histamine H4 Receptor Antagonist with Anti-Inflammatory Properties," Journal of Pharmacology and Experimental Therapeutics, 2004, vol. 309, pp. 404-413.

U.S. Appl. No. 11/863,559; Office Action mailed Mar. 11, 2010.

U.S. Appl. No. 11/863,559; Office Action mailed Sep. 13, 2010.

U.S. Appl. No. 11/863,559; Office Action mailed Feb. 16, 2011.

Varga, et al., "Inhibitory Effects of Histamine H4 Receptor Antagonists on Experimental Colitis in the Rat," European Journal of Pharmacology, 2005, vol. 522, pp. 130-138.

Vinik, et al., "Diabetic Neuropathies," The Medical Clinics of North America, 2004, vol. 88 (4), pp. 947-999.

Vogel, Drug Discovery and Evaluation: Pharmacological Assays, 2nd Edition, Springer-Verlag Berlin Heidelberg, 2002, pp. 702-706.

Wolfe, et al., "Rational Development of Practical Catalysts for Aromatic Carbon-Nitrogen Bond Formation," Accounts of Chemical Research, 1998, vol. 13, pp. 805-818.

Wolfe, et al., "Simple, Efficient Catalyst System for the Palladium-Catalyzed Amination of Aryl Chlorides, Bromides, and Triflates," Journal of Organic Chemistry, 2000, vol. 65 (4), pp. 1158-1174.

Yang, et al., "Palladium-catalyzed Amination of Aryl Halides and Sulfonates," Journal of Organometallic Chemistry, 1999, vol. 576, pp. 125-146.

Zhu, et al., "Cloning, Expression, and Pharmacological Characterization of a Novel Human Histamine Receptor," Molecular Pharmacology, 2001, vol. 59 (3), pp. 434-441.

METHOD FOR PAIN TREATMENT

This application claims priority to provisional application Ser. No. 60/848,954 filed on Oct. 2, 2006.

BACKGROUND OF THE INVENTION

1. Technical Field of the Invention

This invention relates to a method for pain treatment. The method more particularly relates to administering histamine $H_4$ receptor ligands or compositions comprising the same for treating various forms of pain as further described herein.

2. Description of Related Technology

Pain of various types and manifestations affects virtually all humans and animals. In the clinic, pain is the one of the most serious significant medical issues in health care, and affects the widest group of patients. A substantial number of medical disorders and conditions produce pain as part of the disorder or condition. The condition of pain can refer to various forms of pain, for example, inflammatory pain, post surgical pain, and neuropathic pain, among others.

Some methods for treating pain are currently known. Such methods typically involve the administration of a pharmaceutical agent that works through specific biological mechanisms to treat different pain states. However, significant drawbacks for available analgesic and antinociceptive agents exist. For example, selective and non-selective cyclooxygenase inhibitors have been associated with cardiovascular risks, gastric lesions, and bleeding side effects. Opioids have been associated with addiction, abuse liability, respiratory depression, and constipation. Moreover, even given such drawbacks, many current agents are only able to provide a partial or measured degree of relief against some forms of pain.

In particular, patients suffering from neuropathic pain are not well treated by any of the currently available drugs or by agents. Neuropathic pain can develop in response to previous injury or ongoing tissue injury, nerve injury, or diabetes. It is distinct from other types of pain (e.g. inflammatory pain) in that it persists long after signs of the original injury or damage have disappeared. Neuropathic pain also is associated with allodynia, hyperalgesia, or causalgia (Dworkin Clinical Journal of Pain (2002) vol. 18(6) pp. 343-9). Allodynia is the perception of pain following a stimulus that would not normally be painful. Hyperalgesia is an enhanced response to a mildly noxious stimulus. Causalgia is described as a chronic burning pain that shows persistence in the absence of obvious noxious stimuli.

In addition to neuropathic pain, there are other types of pain that are not inflammatory or not due to ongoing inflammation, including osteoarthritis pain, cancer pain, visceral pain.

Neuropathic pain is particularly difficult to treat and is not well treated with current therapies. The topic of neuropathic pain has been reviewed in the scientific literature, for example, Smith, et al. Drug Development Research (2001) vol. 54(3), pp. 140-153; Collins and Chessell Expert Opinion on Emerging Drugs (2005) vol. 10(1), pp. 95-108; Vinik and Mehrabyan Medical Clinics of North America (2004), vol. 88(4), pp. 947-999; Dray, Urban, and Dickenson Trends in Pharmacological Sciences (1994) vol. 15(6) pp. 190-7; Dworkin Clinical Journal of Pain (2002) vol. 18(6) pp. 343-9.

As such, it would be particularly beneficial to identify new methods for treating pain and, more particularly, neuropathic pain. It would be particularly beneficial if such methods are based on previously unexplored mechanisms for pain treatment that may offer improved pain relief or are less associated with side effects.

Histamine is understood to modulate a number of physiological activities, acting through specific histamine receptors (reviewed in Parsons and Ganellin, British Journal of Pharmacology (2006) 147, S127-S135; Igaz and Hegyesi, in Histamine: Biology and Medical Aspects (2004), 89-96; Editor(s): A. Falus; Pub. S. Karger A G, Basel). Four histamine receptors have been identified to date as playing distinct physiological roles. These are the histamine $H_1$ receptor, the histamine $H_2$ receptor, the histamine $H_3$ receptor, and the histamine $H_4$ receptor. The histamine $H_4$ receptor is the most recently identified histamine receptor and has been characterized as a distinct histamine receptor; it is found in a number of mammalian tissues and has been found to modulate a number of physiological processes, including immunological function.

The histamine $H_4$ receptor (also alternately known herein as the $H_4$ receptor) is a member of the 7-transmembrane G-protein coupled receptor (GPCR) family, and is located on the cell surface membrane, where it binds to the endogenous molecule histamine, and transduces signals that modulate specific cellular activities. General aspects of the histamine $H_4$ receptor, its pharmacology, and known ligands of the $H_4$ receptor have been reviewed in de Esch, et al. (Trends in Pharmacological Science (2005), v. 26, pp. 462-469). The human histamine $H_4$ receptor is distinct from other human histamine receptors, has low protein sequence homology with other human histamine receptors: 23% primary amino acid sequence identity with the histamine $H_1$ receptor, 22% primary amino acid sequence identity with the histamine $H_2$ receptor, and 31% primary amino acid sequence identity with the histamine $H_3$ receptor. The $H_4$ receptor was reported by Nakamura, et al. (Biochemical and Biophysical Research Communications (2000), v. 279, pp. 615-620), and was subsequently cloned by numerous research groups (e.g. Nakamura, ibid.; Coge, et al., Biochemical and Biophysical Research Communications (2001) v. 284, pp. 301-309; Liu, et al. Molecular Pharmacology (2001) v. 59, pp. 420-426; Morse, et al. Journal of Pharmacology and Experimental Therapeutics (2001), v. 296, pp. 1058-1066; Nguyen, et al. Molecular Pharmacology (2001), v. 59, pp. 427-433; Zhu, et al. Molecular Pharmacology, (2001), v. 59, pp. 434-441). For an overview of the early efforts on cloning and characterization of histamine $H_4$ receptors see Hough, Molecular Pharmacology, (2001), v. 59, pp. 415-419.

A search for $H_4$ receptor cDNA by RTPCR (reverse transcriptase polymerase chain reaction) of cellular and tissue mRNA located $H_4$ cDNA in various cells and tissues (Nakamura, ibid.). This has been confirmed in additional studies locating $H_4$ cDNA in cells such as leukocytes, eosinophils, mast cells, dendritic cells, and basophils, (Nakamura, ibid.; de Esch, ibid.; Ling, et al. British Journal of Pharmacology (2004) 142, 161-171). Furthermore, $H_4$ cDNA has been identified in several tissues, prominently bone marrow, spleen, lymph nodes, but also in heart, kidney, liver, lung, pancreas, skeletal muscle, leukocyte, prostate, small intestine, testis, and also in different brain regions ((Nakamura, ibid; de Esch, ibid; Coge, ibid).

Study of histamine $H_4$ ligands in animal disease models, as well as in in vitro and ex vivo studies, have demonstrated that the histamine $H_4$ receptor plays an important role in various physiological and pathophysiological processes. For example, in experiments with histamine $H_4$ deficient (knock out) animals and cells and tissues from such histamine $H_4$ deficient animals, the histamine $H_4$ receptor has been demonstrated to play an important role in various physiological and pathophysiological processes. However, study of diseases and disorders where histamine $H_4$ receptors have been found to play an important role predominantly have been related to, for example, asthma, allergy, rheumatoid arthritis, and inflammation.

SUMMARY OF THE INVENTION

The invention provides a method of pain treatment comprising administering a histamine $H_4$ receptor ligand, a salt, ester, or amide thereof, or a composition comprising such ligand, salt, ester, or amide. The histamine $H_4$ receptor ligands modulate or regulate the activity of histamine $H_4$ receptors. The ligands can demonstrate antagonist, inverse agonist, or partial agonist activity.

Antagonists are ligands that block receptor activation by an agonist. In the case of the histamine $H_4$ receptor, a histamine $H_4$ receptor antagonist blocks activation of the histamine $H_4$ receptor by a histamine $H_4$ receptor agonist such as the endogenous agonist ligand histamine. Inverse agonists are ligands that block receptor activation. More generally, they block intrinsic activation of a receptor that occurs in the absence of an activation by an agonist, and also block receptor activation by an agonist. Partial agonists are ligands that bind to receptors but only partially activate the receptor; in so doing, partial agonists compete with full agonists and block full activation of the receptor. In the case of the histamine $H_4$ receptor, the endogenous agonist histamine is a full agonist.

Preferably the ligands are histamine $H_4$ receptor antagonists. More preferably the ligands are histamine $H_4$ receptor inverse agonists.

Histamine $H_4$ receptor ligands of various structural classes have been identified and some are reviewed in Schwartz, Expert Opinion in Therapeutic Patents (2003) vol. 13, pp. 851-865. Additional histamine $H_4$ receptor ligands also are provided, and are considered within the scope of the invention.

The various forms of pain that can be treated can include all types of pain. Examples of pain for which the method can be carried out include, but are not limited to, for example, inflammatory pain, chemically induced pain, pain resulting from surgery, pain resulting from burns, pain resulting from osteoarthritis, non-inflammatory pain, post surgical pain, and neuropathic pain.

This invention discloses the novel method of treating pain (including diverse types of pain, including inflammatory pain, post surgical pain, and neuropathic pain) by administration of histamine $H_4$ receptor ligands. The utility of histamine $H_4$ receptor ligands to treat neuropathic pain is novel.

This invention discloses the novel utility of histamine $H_4$ receptor ligands to treat pain, including distinctly different types of pain, including inflammatory pain, chemically induced pain, pain resulting from surgery, pain resulting from burns, pain resulting from osteoarthritis, non-inflammatory pain, and to treat neuropathic pain. The method of the invention can demonstrate particular benefit in its effectiveness in treating osteoarthritis pain, post-surgical pain, and neuropathic pain.

These methods and further methods contemplated as part of the invention are further described herein.

DETAILED DESCRIPTION OF THE INVENTION

Histamine $H_4$ Receptor Ligands and Compositions Thereof

A number of histamine $H_4$ receptor ligands are known. Such compounds have been demonstrated to modulate or regulate the activity of histamine $H_4$ receptors. The ligands can demonstrate antagonist, inverse agonist, or partial agonist activity. Antagonists are ligands that block receptor activation by an agonist. In the case of the histamine $H_4$ receptor, a histamine $H_4$ receptor antagonist blocks activation of the histamine $H_4$ receptor by a histamine $H_4$ receptor agonist such as the endogenous agonist ligand histamine. Inverse agonists are ligands that block receptor activation. More generally, they block intrinsic receptor activation that occurs in the absence of an activation by an agonist, and they also act as antagonists, blocking receptor activation by an agonist. Partial agonists are ligands that bind to receptors but only partially activate the receptor; in so doing, partial agonists compete with full agonists and block full activation of the receptor. In the case of the histamine $H_4$ receptor, the endogenous agonist histamine is a full agonist. Preferably the ligands are histamine $H_4$ receptor antagonists. More preferably the ligands are histamine $H_4$ receptor inverse agonists. Administering histamine $H_4$ receptor ligands, or a salt, ester, or amide thereof, in accordance with the invention are useful for treating pain, and particularly inflammatory pain, osteoarthritis pain, post surgical pain, and neuropathic pain.

Histamine $H_4$ receptor ligands of various structural classes have been identified and some are reviewed in Schwartz, Expert Opinion in Therapeutic Patents (2003) vol. 13, pp. 851-865. To date, examples of histamine $H_4$ receptor ligands generally have a formula (I)-(XI).

For example, some histamine $H_4$ receptor ligands of formula (I):

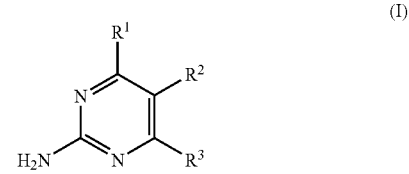

its tautomeric or stereoisomeric form, or a salt thereof:

wherein
R¹ represents

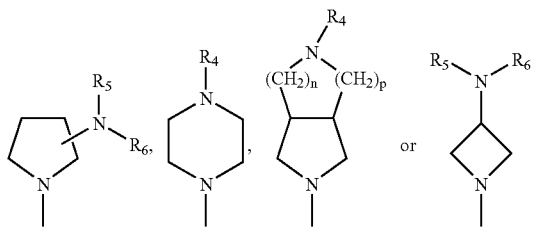

wherein
n represents an integer of 1, 2 or 3;
p represents an integer of 0 or 1;
$R_4$ represents hydrogen or $C_{1-6}$alkyl optionally substituted by halogen, cyano, hydroxy, carboxy, amino, N—($C_{1-6}$alkyl)amino, N,N-di($C_{1-6}$alkyl)amino, $C_{1-6}$alkylthio, $C_{1-6}$alkoxy, or $C_{3-8}$cycloalkyl;
$R_5$ and $R_6$ independently represent hydrogen or $C_{1-6}$alkyl optionally substituted by halogen, cyano, hydroxy, carboxy, amino, N—($C_{1-6}$alkyl)amino, N,N-di-($C_{1-6}$alkyl)amino, $C_{1-6}$alkylthio, $C_{1-6}$alkoxy, or $C_{3-8}$cycloalkyl;
$R^2$ represents hydrogen, halogen or $C_{1-6}$alkyl; and
$R^3$ represents aryl or heteroaryl,
wherein
said aryl and heteroaryl are optionally having one or more substituents selected from the group consisting of halogen, carboxy, hydroxy, cyano, nitro, $C_{3-8}$cyclo alkyl, phenyl, $C_{1-6}$alkanoyl, amino, N—($C_{1-6}$alkyl)amino, N—($C_{1-6}$alkanoyl)amino, N ($C_{1-6}$alkylsulfonyl)amino, N-(phenylsulfonyl)amino, N—($C_{1-6}$alkoxycarbonyl)amino, N-(aryl)amino, N-(aryl $C_{1-6}$alkyl)amino, N,N-di($C_{1-6}$alkyl)amino, $C_{1-6}$alkoxy-carbonyl, $C_{1-6}$alkylthio, aminocarbonyl, N—($C_{1-6}$alkyl)aminocarbonyl, N,N-di-($C_{1-6}$alkyl)aminocarbonyl, $C_{1-6}$alkylsulfonyl, sulfamoyl, aryl$C_{1-6}$alkoxycarbonyl, $C_{1-6}$alkyl optionally substituted by cyano, hydroxy, carboxy, amino, N—($C_{1-6}$alkyl)-amino, N,N-di($C_{1-6}$alkyl)amino, $C_{1-6}$alkylthio, $C_{1-6}$alkoxy, or mono-, di-, or tri-halogen, and $C_{1-6}$alkoxy optionally substituted by $C_{3-8}$cycloalkyl, or mono-, di-, or tri-halogen have been described in WO2005/054239A1, filed Nov. 24, 2004, and WO2005/014556A1, filed Jul. 23, 2004, to Sato, et al., each of which is herein incorporated by reference, as is the genus of histamine $H_4$ receptor antagonists described. Such compounds may be prepared by the following general synthetic methods:

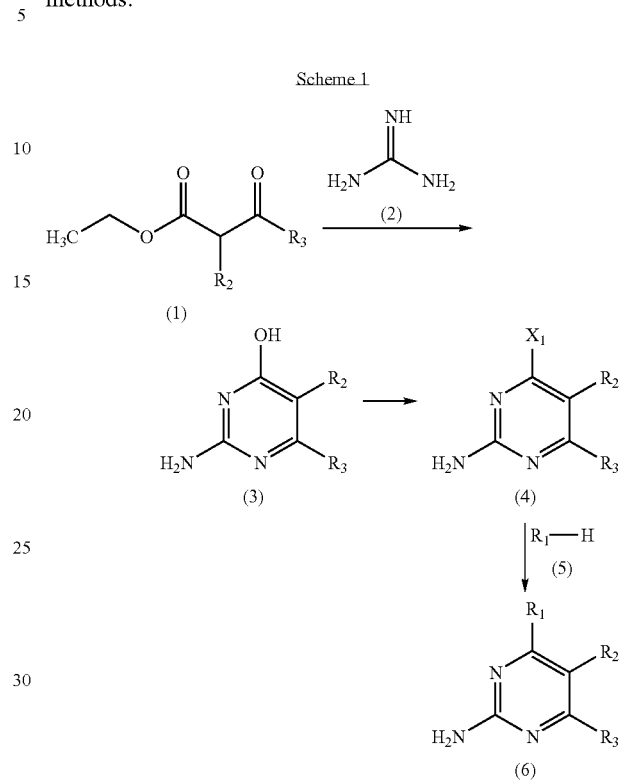

Compounds of formula (6), wherein $R_1$, $R_2$ and $R_3$ are defined in formula (I), can be made as described in Scheme 1. A keto-ester of formula (1) can be reacted with guanidine (2) or a salt of guanidine (2) in a solvent such as ethanol using a base such as sodium ethoxide to provide compounds of formula (3). Compounds of formula (3) can be reacted with a reagent such as $POCl_3$, $POBr_3$, or triflic anhydride to provide compounds of formula (4) wherein $X_1$ is a leaving group such as Cl, Br, or triflate. An intermediate of formula (4) can be reacted with a an amine of formula (5) wherein H is a proton on a nitrogen atom of the amine, to provide compounds of formula (6).

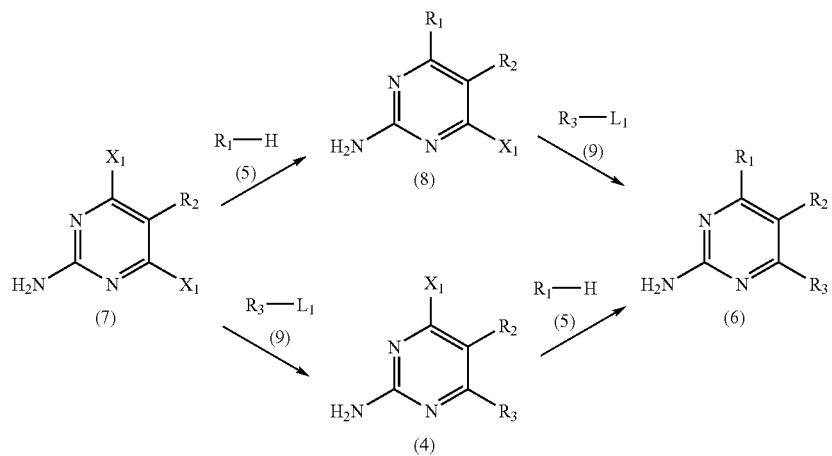

Compounds of formula (6), wherein $R_1$, $R_2$ and $R_3$ are defined in formula (I), can also be made as described in Scheme 2. A pyrimidine of formula (7), wherein $X_1$ is a leaving group such as chlorine or bromine, can be reacted with an amine of formula (5), wherein H is a hydrogen attached to a nitrogen atom of the amine, to provide compounds of formula (8). Compounds of formula (7), for example 2-amino-4,6-dichloropyrimidine (CAS # 56-05-3), can be obtained from commercial sources or prepared by one skilled in the art. Alternatively, a compound of formula (8) can be reacted with an organometallic reagent of formula (9), wherein $L_1$ represents a metal such as tin, zinc, or boron. $R_3$-$L_1$ reagents include reagents such as a boronic acids of formula $R_3B(OH)_2$ or pinacolboranyl-$R_3$, and an organostannanes such as $(R_3)SnBu_3$. The organometallic reagent (9) is reacted with a compound of formula (8) in the presence of a palladium catalyst such as $Pd(Ph_3P)_4$ and a base, such as $Na_2CO_3$, for example under the conditions such as used for the Suzuki reaction, the Stille reaction or the Negishi reaction, to provide compounds of formula (6). Alternatively, a compound of formula (7) can be reacted with a compound of formula (9), in a manner as described for the conversion of compounds of formula (8) to compounds of formula (6), to provide a compound of formula (4). Compound of formula (4) can be reacted with a compound (5), in a manner as described for the conversion of compounds of formula (7) to compounds of formula (8), to provide a compound of formula (6).

Examples of compounds of formula (I) include, but are not limited to, 5-((4aR,7aR)-tetrahydro-1H-pyrrolo[3,4-b]pyridin-6(2H,7H,7aH)-yl)biphenyl-3-amine; 3-(naphthalen-1-yl)-5-((4aR,7aR)-tetrahydro-1H-pyrrolo[3,4-b]pyridin-6(2H,7H,7aH)-yl)aniline; 5-((4aR,7aR)-tetrahydro-1H-pyrrolo[3,4-b]pyridin-6(2H,7H,7aH)-yl)-3'-(trifluoromethyl)biphenyl-3-amine; 3',4'-dichloro-5-((4aR,7aR)-tetrahydro-1H-pyrrolo[3,4-b]pyridin-6(2H,7H,7aH)-yl)biphenyl-3-amine; 6-fluoro-5-((4aR,7aR)-tetrahydro-1H-pyrrolo[3,4-b]pyridin-6(2H,7H,7aH)-yl)biphenyl-3-amine; 5-(1-methylhexahydropyrrolo[3,4-b]pyrrol-5(1H)-yl)biphenyl-3-amine; 1-(5-amino-3'-chlorobiphenyl-3-yl)-N-methylazetidin-3-amine; 1-(5-amino-3'-fluorobiphenyl-3-yl)-N-methylazetidin-3-amine; 1-(5-amino-2-fluorobiphenyl-3-yl)-N-methylazetidin-3-amine; and 1-(5-aminobiphenyl-3-yl)-N-ethylazetidin-3-amine.

Other compounds that have been characterized as histamine $H_4$ receptor ligands are compounds of structure (IIa) and (IIb):

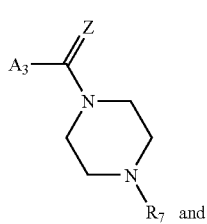

(IIa)

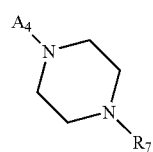

(IIb)

wherein
Z is oxygen or sulfur;
$R_7$ is hydrogen or chosen from alkyl or cycloalkyl;
the piperidine moiety is optionally substituted from one or more groups selected from alkyl, cycloalkyl, $CF_3$, or $CH_2OH$;
$A_3$ is a heterocyclic group selected from indol-2-yl, benzoimidazol-2-yl, benzofuran-2-yl, benzothiophen-2-yl, 4H-thieno[3,2-b]pyrrole-5-yl, 4H-furo[3,2-b]pyrrole-5-yl, 6H-thieno[2,3-b]pyrrole-5-yl, 6H-furo[2,3-b]pyrrole-5-yl, benzo[d]oxazol-2-yl, or benzo[d]thiazol-2-yl;
$A_4$ is a heterocyclic group selected from 3-oxo-3,4-dihydroquinoxalin-2-yl, and 3-oxo-3,4-dihydropyrido[2,3-b]pyrazin-2-yl, 3-thioxo-3,4-dihydroquinoxalin-2-yl, 3-thioxo-3,4-dihydropyrido[3,2-b]pyrazin-2-yl, 3-imino-3,4-dihydroquinoxalin-2-yl, or 3-imino-3,4-dihydropyrido[3,2-b]pyrazin-2-yl;
wherein the carbon atoms of $A_3$ and $A_4$ are optionally substituted with one or more groups selected from alkyl, fluoroalkyl, cyanoalkyl, cycloalkyl, fluorocycloalkyl, cycloalkoxyalkyl, alkylcycloalkyl, alkylfluorocycloalkyl, aryl, heteroaryl, heterocycle, O-aryl, O-heteroaryl, S-aryl, $CONR_8R_9$, $NR_8COalkyl$, acyl, acyloxy, alkenyl, alkoxy, alkoxyalkoxy, alkoxyalkyl, alkoxycarbonyl, alkoxyimino, alkoxysulfonyl, alkylcarbonyl, alkylsulfonyl, alkynyl, amido, carboxy, cyano, fluoroalkoxy, formyl, haloalkoxy, haloalkyl, halogen, hydroxy, hydroxyalkyl, mercapto, nitro, alkylthio, $-NR_8R_9$, -carbonyl($NR_8R_9$), $-SO_2$ ($NR_8R_9$), and $N(R_8)SO_2(R_9)$;
wherein $R_8$ and $R_9$ are each independently selected from hydrogen, alkyl, fluoroalkyl, cycloalkyl, cyanoalkyl, fluorocycloalkyl, cycloalkoxyalkyl, alkylcycloalkyl, alkylfluorocycloalkyl, aryl, heteroaryl, heterocycle, acyl, alkoxyalkyl, alkoxycarbonyl, alkylcarbonyl, alkylsulfonyl, amido, formyl, hydroxy, and hydroxyalkyl;

The following references describe histamine $H_4$ receptor ligands that are a subset of formula (IIa), and provide general synthetic methods, as well as specific examples of histamine $H_4$ receptor ligands in the following U.S. or International Patent Publications: US2004/0048878A1, filed Sep. 5, 2003, to Cai, et al.; U.S. Pat. No. 6,803,362B2, filed Mar. 8, 2002, to Carruthers, et al.; US2003/0207893A1, filed Mar. 8, 2002, to Carruthers et al.; WO2004/022061A1, filed Sep. 5, 2003, to Dunford et al.; and WO2002/072548A2, filed Mar. 8, 2002 to Carruthers, et al., each of which is herein incorporated by reference.

The following reference describes histamine $H_4$ receptor ligands that are a subset of formula (IIb), and provide general synthetic methods, as well as specific examples of histamine $H_4$ receptor ligands in the following U.S. or International Patent Publications: US2005/0070527A1, filed Sep. 29, 2004, to Edwards and Venable; each publication of which is herein incorporated by reference.

Compounds of formula (IIa) and (IIb) may be prepared by the following general synthetic methods:

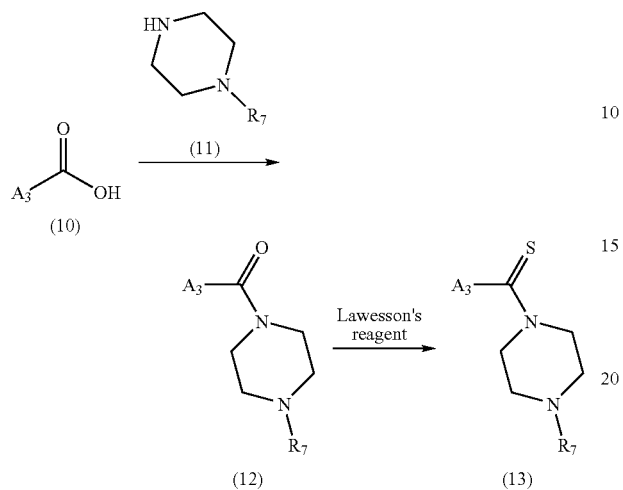

Scheme 3

Compounds of formula (12) and (13), wherein $R_7$ and $A_3$ are defined in formula (IIa), can be made as described in Scheme 3. An acid of formula (10) can be coupled with a piperazine of structure (11) using conventional methods of amide bond formation. For example, the carboxyl group of compound (10) may be activated as an active ester, acid chloride, anhydride, mixed anhydride, carbonic mixed anhydride or the like and treated with an amine of formula (II) to provide compounds of formula (12). For example, the compound of formula (10) may be converted to the corresponding active ester upon treatment with 1-hydroxybenzotraizole in the presence of a carbodiimide for example dicyclohexylcarbodiimide, optionally in the presence of a base such as triethyl amine. Acids of formula (10) can be obtained from commercial sources or prepared by one skilled in the art. Compounds of formula (12) can be treated with Lawesson's reagent in a solvent such as THF to provide compounds of formula (13).

Compounds of formula (IIb) can be generated by reaction of 2,3-dihalo substituted pyrido[3,2-b]pyrazines or 2,3-dihalo substituted quinoxalines with a suitably substituted piperazine, followed by treatment with ammonia, hydrogen sulfide or water to provide compounds of formula IIb. 2,3-Dihalo substituted pyrido[3,2-b]pyrazines and 2,3-dihalo substituted quinoxalines can be generated by the halogenation of pyrido[3,2-b]pyrazine-2,3(1H,4H)-diones and quinoxaline-2,3(1H,4H)-diones, respectively, using reagents such as thionyl chloride, thionyl bromide or phosphohorus oxychloride. Pyrido[3,2-b]pyrazine-2,3(1H,4H)-diones and quinoxaline-2,3(1H,4H)-diones can be generated by the reaction of pyridine-2,3-diamines and benzene-1,2-diamines, respectively, with oxylate derivatives such as dimethyl oxylate, diethyl oxylate or oxalyl chloride.

Examples of compounds of formula (IIa) include, but are not limited to, (5-chloro-1H-indol-2-yl)(3,4-dimethylpiperazin-1-yl)methanone; (5-bromobenzofuran-2-yl)(4-methylpiperazin-1-yl)methanone; (1H-indol-2-yl)(4-methylpiperazin-1-yl)methanethione; (7-methyl-1H-indol-2-yl)(4-methylpiperazin-1-yl)methanone; (2,3-dimethyl-4H-thieno[3,2-b]pyrrol-5-yl)(4-methylpiperazin-1-yl)methanone; (2-chloro-3-methyl-4H-thieno[3,2-b]pyrrol-5-yl)(4-methylpiperazin-1-yl)methanone; and (2,3-dichloro-4H-thieno[3,2-b]pyrrol-5-yl)(4-methylpiperazin-1-yl)methanone.

Examples of compounds of formula (IIb) include, but are not limited to, 8-methyl-3-(4-methylpiperazin-1-yl)quinoxalin-2(1H)-one; 8-methyl-3-(piperazin-1-yl)quinoxalin-2(1H)-one; 3-(4-methylpiperazin-1-yl)-6-(trifluoromethyl)quinoxalin-2(1H)-one; 7-chloro-6-fluoro-3-(4-methylpiperazin-1-yl)quinoxalin-2(1H)-one; and 6-chloro-7-fluoro-3-(4-methylpiperazin-1-yl)quinoxalin-2(1H)-one.

Compounds of formula (III) are histamine $H_4$ receptor ligands and are described in US2006/0111416A1, filed Nov. 21, 2005, to Lane and Price, the publication which is herein incorporated by reference. Compounds of formula (III):

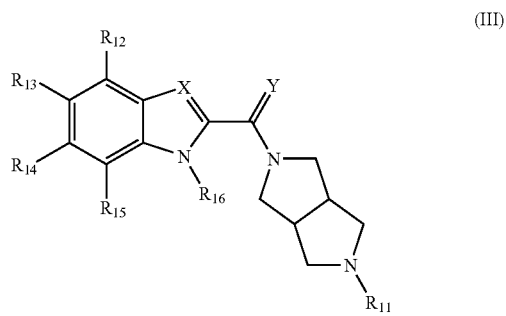

(III)

wherein $R_{11}$ is H or ($C_1$-$C_4$) alkyl optionally substituted with a hydroxy;

X is N or C—$R_{19}$ wherein $R_{19}$ is H or methyl;

Y is O or NH;

$R_{16}$ is H or methyl; and $R_{12}$, $R_{13}$, $R_{14}$ and $R_{15}$ are each independently selected from H, halo, cyano, ($C_1$-$C_4$) alkyl, ($C_1$-$C_4$)alkoxy, trifluoromethyl, trifluoromethoxy, hydroxy, $(CH_2)_r$—C(O)O—$R_{17}$, $(CH_2)_r$—O—$(CH_2)_p$—$R_{18}$ and $(CH_2)_r$—$R_{18}$, wherein p and r are both independently 0 or 1, $R_{17}$ is H or ($C_1$-$C_4$)alkyl and $R_{18}$ is phenyl.

Compounds of formula (III) may be prepared by the following general synthetic methods:

Scheme 4

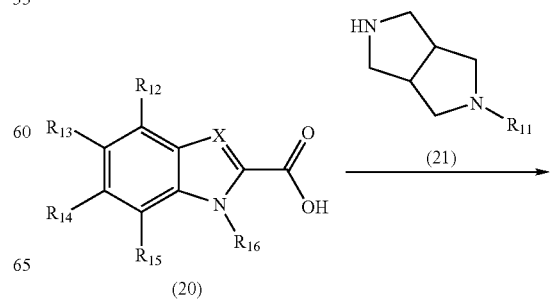

-continued

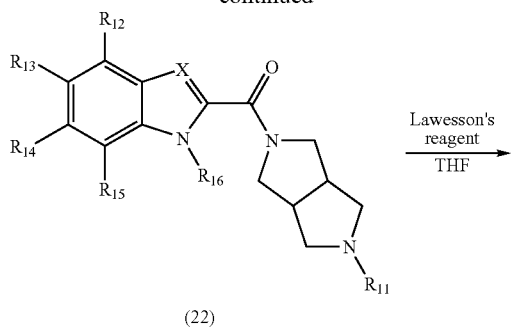

(22)

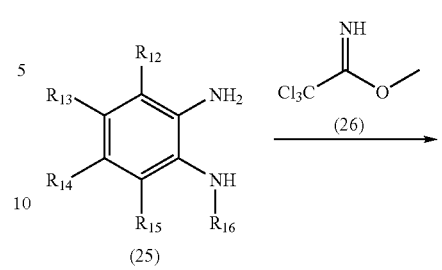

Scheme 5

(25) (26)

(27) (21)

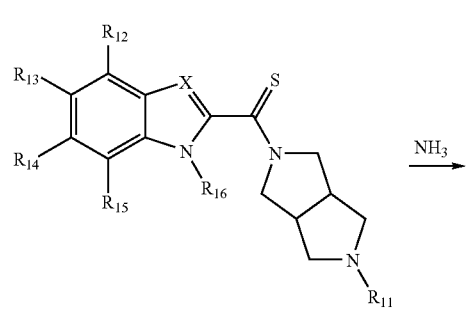

(23)

(24)

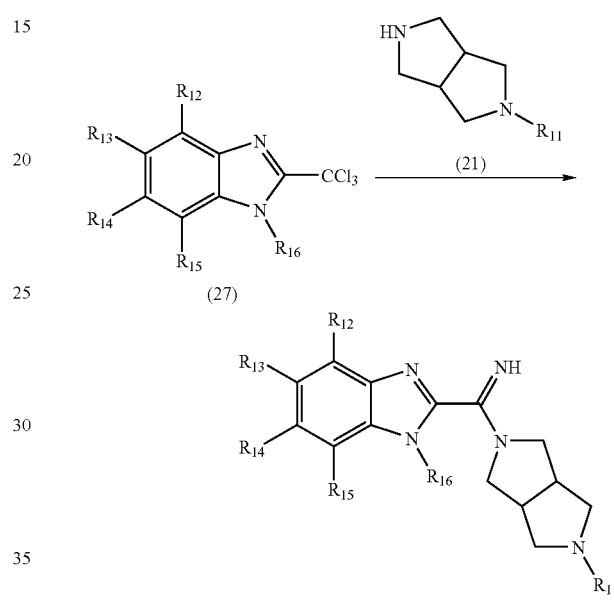

(28)

Compounds of formula (22) and (24), wherein $R_{11}$, $R_{12}$, $R_{13}$, $R_{14}$, $R_{15}$, $R_{16}$ and X are defined in formula (III) can be made as described in Scheme 4. Acids of formula (20) can be coupled with amines of formula (21) using conventional methods of amide bond formation. For example, the carboxyl group of compound (20) may be activated as an active ester, acid chloride, anhydride, mixed anhydride, carbonic mixed anhydride or the like and treated with an amine of formula (21) to provide compounds of formula (22). For example, the compound of formula (20) may be converted to the corresponding active ester upon treatment with 1-hydroxybenzotriazole in the presence of a carbodiimide for example dicyclohexylcarbodiimide in the presence of a base such as triethyl amine. Acids of formula (20) can be obtained from commercial sources or prepared by one skilled in the art. Compounds of formula (22) can be treated with Lawesson's reagent in a solvent such as THF to provide compounds of formula (23). Compounds of formula (23) can be treated with an excess of ammonia or an ammonium equivalent in the presence of an activating reagent such as methyl iodide or mercuric acetate in a suitable solvent such as THF to provide compounds of formula (24).

Compounds of formula (28), wherein $R_{11}$, $R_{12}$, $R_{13}$, $R_{14}$, $R_{15}$ and $R_{16}$ and Y are defined in formula (III) can be made as described in Scheme 5. A diamine of structure (25) can be condensed with acetimidate (26) in a solvent such as acetic acid to provide benzimidazoles of formula (27). Benzimidazoles of formula (27) can be treated with amines of formula (21) and a source of ammonia to provide compounds of formula (28).

Examples of compounds of formula (III) include, but are not limited to, (5-fluoro-1H-benzo[d]imidazol-2-yl)(5-methylhexahydropyrrolo[3,4-c]pyrrol-2(1H)-yl)methanimine; (5,6-difluoro-1H-benzo[d]imidazol-2-yl)(5-methylhexahydropyrrolo[3,4-c]pyrrol-2(1H)-yl)methanimine; (6-fluoro-7-methyl-1H-benzo[d]imidazol-2-yl)(5-methylhexahydropyrrolo[3,4-c]pyrrol-2(1H)-yl)methanimine; (7-methyl-1H-benzo[d]imidazol-2-yl)(5-methylhexahydropyrrolo[3,4-c]pyrrol-2(1H)-yl)methanimine; (7-fluoro-1H-indol-2-yl)(5-methylhexahydropyrrolo[3,4-c]pyrrol-2(1H)-yl)methanone; and (5-chloro-1H-indol-2-yl)(5-methylhexahydropyrrolo[3,4-c]pyrrol-2(1H)-yl)methanone.

Compounds of structure (IV) are histamine $H_4$ receptor ligands and are described in WO2006/050965A1, filed Nov. 11, 2005, to Harris, et al., which publication is herein incorporated by reference.

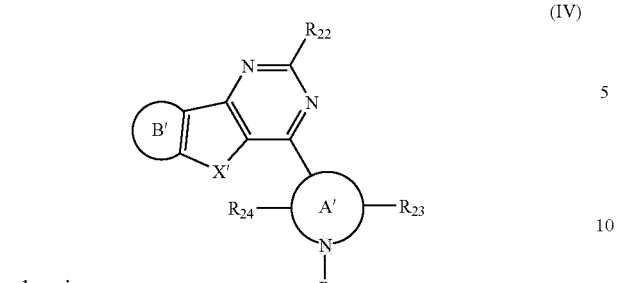

(IV)

wherein

A' represents a fully saturated or partially unsaturated ring of 5 to 7 atoms, at least one of which is a nitrogen atom;
B' represents aryl or heteroaryl ring of 5 to 6 atoms, wherein B' is optionally substituted with one up to three groups of formula $R_{25}$, where $R_{25}$ represents independently: H, F, Cl, Br, I, $C_{1-4}$alkyl, $C_{3-6}$-cycloalkyl, heterocycloalkyl, $C_{1-4}$-alkoxy, $C_{3-6}$cycloalkoxy, OH, $OCF_3$, $CF_3$, cyano, or $NR_{26}R_{27}$; $R_{26}$ and $R_{27}$ being independently H or $C_{1-4}$-alkyl;
X' represents O, NH, S, or $CH_2$;
$R_{21}$ represents H, or $C_{1-4}$-alkyl;
$R_{22}$ represents H, optionally substituted $C_{1-4}$alkyl, optionally substituted $C_{3-6}$-cycloalkyl, or optionally substituted aryl or heteroaryl;
$R_{23}$ and $R_{24}$ represent independently H, or $C_{1-2}$-alkyl; or $R_{23}$ and $R_{24}$ taken together may represent a $C_{1-4}$-alkylene group;
and corresponding N-oxides, pharmaceutically acceptable salts, solvates, metabolites and prodrugs of such compounds.

Compounds of formula (IV) can be prepared by the following synthetic methods:

Scheme 6

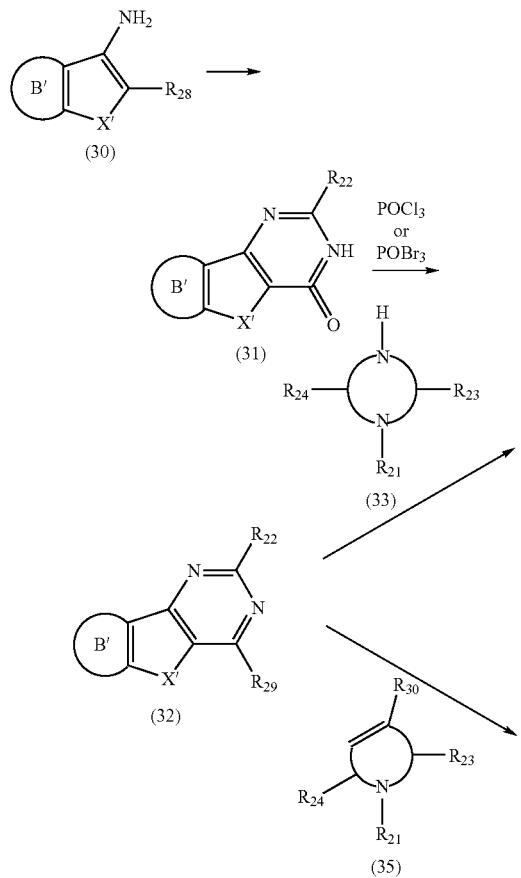

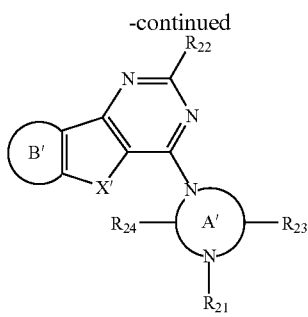

(34)

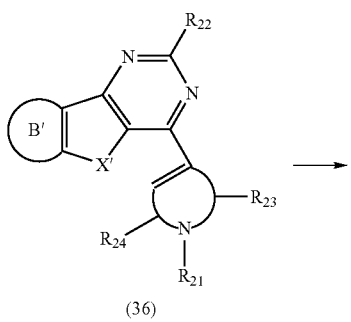

(36)

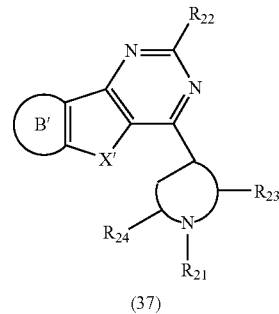

(37)

Compounds of formula (34), (36) and (37), wherein $R_{21}$, $R_{22}$, $R_{23}$, $R_{24}$, A', B' and X' are defined in formula (IV) can be made as described in Scheme 6. Compounds of formula (31) can be prepared from compounds of formula (30), wherein $R_{28}$=C(=O)$NH_2$, CN or C(=O)Oalkyl, by reaction with a suitable condensing agent. Wherein $R_{22}$=H, suitable condensing agents include formic acid, formamide and trialkyl orthoformates. Wherein $R_{22}$=alkyl or cycloalkyl, suitable condensing agents include symmetrical alkyl anhydrides, alkyl amides, alkyl esters and alkyl nitriles. Wherein $R_{22}$=aryl or heteroaryl, suitable condensing agents include aryl acid chlorides, heteroaryl acid chlorides, aryl aldehydes and heteroaryl aryl aldehydes. An additional reagent such as HCl gas or $POCl_3$ may be required in the conversion of compounds of formula (30) to compounds of (31). Compounds of formula (30) can be obtained from commercial sources or prepared by one skilled in the art. Compounds of formula (32), wherein $R_{29}$=Cl or Br, can be prepared by the reaction of compounds of formula (31) with a suitable halogenating reagent, such as $POCl_3$ or $POBr_3$. Compounds of formula (34) can be prepared by the reaction of cyclic diamines of formula (33) with compounds of formula (32) in an inert solvent, usually with heating, optionally in the presence of a base such as triethyl amine, and optionally using a palladium catalyst such as a mixture of palladium bis(trifluoroacetate) and tri(tert-butyl) phosphine. Compounds of formula (36) can be prepared by the reaction of compounds of formula (32) with a substituted alkene of formula (35), wherein $R_{30}$ is a suitable metal-containing group such as a boronate ester or a trialkyl or a triarylstannane, in the presence of a suitable palladium catalyst such as tris(dibenzylideneacetone)dipalladium. Compounds of formula (37) can be prepared by reduction of compounds of formula (36) using conditions such as catalytic hydrogenation.

Examples of compounds of formula (IV) include, but are not limited to, 8-chloro-2-methyl-4-(4-methylpiperazin-1-yl)benzofuro[3,2-d]pyrimidine; 8-chloro-4-(8-methyl-3,8-diazabicyclo[3.2.1]octan-3-yl)benzofuro[3,2-d]pyrimidine; 8-chloro-4-(1-methylpyrrolidin-3-yl)benzofuro[3,2-d]pyrimidine; 8-chloro-4-(1-methylpiperidin-4-yl)benzofuro[3,2-d]pyrimidine. Other structural classes of compounds with reported histamine $H_4$ receptor activity can be found among non-imidazole compounds (see Arienti, et al. (US2005/0070550A1); Buzard, et al. (WO2005/092066A2)), and among imidazole-containing compounds found in Anthes, et al. WO2004/066960A1; and Burns, et al. (WO2005/014579A1). Such publications related to non-imidazole and imidazole-containing compounds are herein incorporated by reference.

Also suitable for the invention are compounds of formula (V):

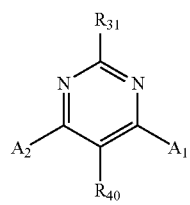

wherein:

$R_{31}$ is selected from H, —NH(alkyl), —NHOH, —NHOCH$_3$, alkyl, fluoroalkyl, cyanoalkyl, cycloalkyl, fluorocycloalkyl, hydroxyalkyl, cyano, and alkoxy;

$R_{32}$, $R_{33}$, $R_{34}$, $R_{35}$, $R_{36}$, $R_{40}$ are each independently selected from the group consisting of hydrogen, alkyl, fluoroalkyl, cyanoalkyl, cycloalkyl, fluorocycloalkyl, cycloalkoxyalkyl, alkylcycloalkyl, alkylfluorocycloalkyl, aryl, heteroaryl, heterocycle, O-aryl, O-heteroaryl, S-aryl, CONR$_{38}$R$_{39}$, NR$_{38}$COalkyl, acyl, acyloxy, alkenyl, alkoxy, alkoxyalkoxy, alkoxyalkyl, alkoxycarbonyl, alkoxyimino, alkoxysulfonyl, alkylcarbonyl, alkylsulfonyl, alkynyl, amido, carboxy, cyano, fluoroalkoxy, formyl, haloalkoxy, haloalkyl, halogen, hydroxy, hydroxyalkyl, mercapto, nitro, alkylthio, —NR$_{38}$R$_{39}$, -carbonyl(NR$_{38}$R$_{39}$), —SO$_2$(NR$_{38}$R$_{39}$), and N(R$_{38}$)SO$_2$(R$_{39}$);

$R_{37}$ is selected from the group consisting of hydrogen, alkyl, fluoroalkyl, cyanoalkyl, hydroxyalkyl, alkoxyalkyl, cycloalkyl, fluorocycloalkyl, cycloalkoxyalkyl, alkylcycloalkyl, and alkylfluorocycloalkyl;

$R_{38}$, and $R_{39}$ are each independently selected from hydrogen, alkyl, fluoroalkyl, cycloalkyl, cyanoalkyl, fluorocycloalkyl, cycloalkoxyalkyl, alkylcycloalkyl, alkylfluorocycloalkyl, aryl, arylalkyl, heteroaryl, heteroarylalkyl, heterocycle, acyl, alkoxyalkyl, alkoxycarbonyl, alkylcarbonyl, alkylsulfonyl, amido, formyl, hydroxy, and hydroxyalkyl;

$A_1$ is a group of structure

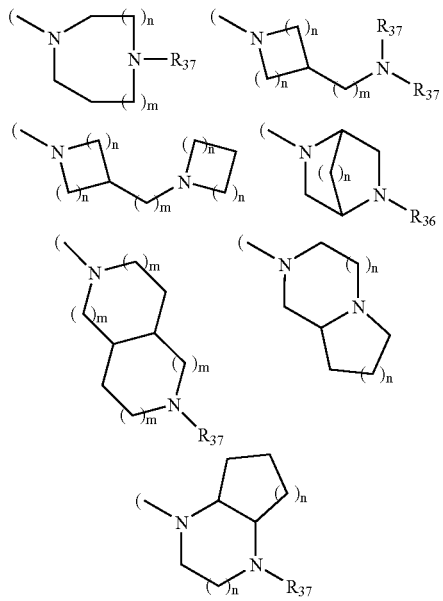

n is 1, 2, or 3;
m is 0, 1, or 2;

wherein each carbon atom of groups $A_1$ may be optionally substituted with one or more groups selected from alkyl, fluoroalkyl, cyanoalkyl, cycloalkyl, fluorocycloalkyl, cycloalkoxyalkyl, alkylcycloalkyl, alkylfluorocycloalkyl, fluorine, acyl, acyloxy, alkenyl, alkoxy, alkoxyalkoxy, alkoxyalkyl, alkoxycarbonyl, alkylcarbonyl, alkylsulfonyl, alkynyl, amido, carboxy, cyano, fluoroalkoxy, formyl, haloalkoxy, haloalkyl, halogen, hydroxy, hydroxyalkyl, mercapto, nitro, and alkylthio;

$A_2$ is a phenyl ring of structure

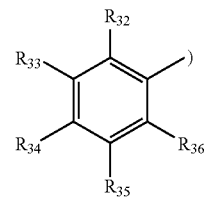

or a hydrogen, iodine, hetearomatic group, heterocycle, —NR$_{38}$R$_{39}$, alkyl group, a group of structure $A_1$, an aromatic ring, a naphthylene, wherein the carbon atoms of the group $A_2$ may be optionally substituted with one or more groups selected from alkyl, fluoroalkyl, cyanoalkyl, cycloalkyl, fluorocycloalkyl, cycloalkoxyalkyl, alkylcycloalkyl, alkylfluorocycloalkyl, aryl, heteroaryl, heterocycle, O-aryl, O-heteroaryl, S-aryl, CONR$_{38}$R$_{39}$, NR$_{38}$COalkyl, acyl, acyloxy, alkenyl, alkoxy, alkoxyalkoxy, alkoxyalkyl, alkoxycarbonyl, alkoxyimino, alkoxysulfonyl, alkylcarbonyl, alkylsulfonyl, alkynyl, amido, carboxy, cyano, fluoroalkoxy, formyl, haloalkoxy, haloalkyl, halogen, hydroxy, hydroxyalkyl, mercapto, nitro, alkylthio, —$NR_{38}R_{39}$, -carbonyl($NR_{38}R_{39}$), —$SO_2$($NR_{38}R_{39}$), and N($R_{38}$)$SO_2$($R_{39}$);

or a pharmaceutically acceptable, salt, ester, amide, or prodrug thereof.

Compounds of formula (V) can be prepared by the following synthetic methods:

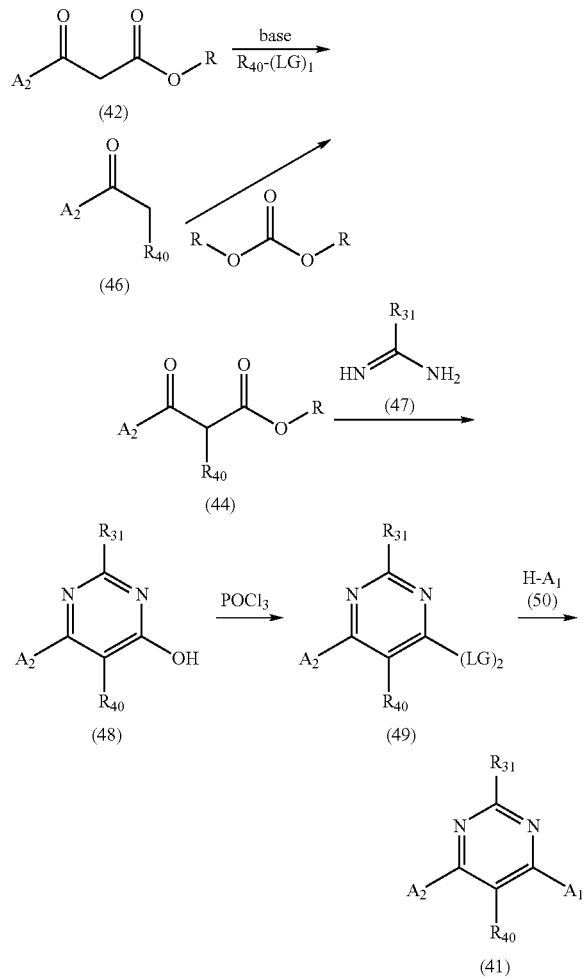

Compounds of formula (41), wherein $R_{31}$, $R_{40}$, $A_1$ and $A_2$ have been defined in formula (V) can be prepared as described in Scheme 7. Alternatively, keto-esters of formula (42) can be reacted with a compound of formula (45), wherein (LG)$_1$ is a leaving group such fluorine, chlorine, bromine, iodine, mesylate or triflate, to provide compounds of formula (44). Alternatively, ketones of formula (46) can be reacted with a carbonate such as dimethyl carbonate, or a chloroformate such as ethyl chloroformate, in the presence of a base such as sodium hydride to provide keto-esters of formula (44), wherein R=lower alkyl. Keto-esters of formula (44) can be treated with an amidate or guanidate of formula (47), such as guanidine nitrate, in the presence of a base such as potassium carbonate and heated in a solvent such as DMF to provide 4-hydroxy-pyrimidines of formula (48). 4-Hydroxy-pyrimidines of formula (48) can exist as shown in the structure in Scheme 7 or in a tautomeric form. Pyrimidines of formula (48) can be treated with a chlorinating reagent such as $POCl_3$, usually with heating, to provide pyrimidines of formula (49) wherein (LG)$_2$=Cl. A base such as $Et_3N$ or N,N-dimethylaniline in a solvent such as toluene, dioxane or chloroform may be required. Pyrimidines of formula (49) can also be treated with a sulfonating reagent such as para-toluensulfonyl chloride in the presence of a base such as triethylamine and a solvent such as pyridine or chloroform to provide 2-amino-pyrimidines of formula (49) wherein (LG)$_2$=O—$SO_2$—R', wherein R' is lower alkyl, lower fluoroalkyl or aryl. Pyrimidines of formula (49), wherein (LG)$_2$=Cl or O—$SO_2$—R', can be treated with amines of formula (50), wherein H is a hydrogen on a nitrogen atom, and heated, optionally in the presence of a base such as triethylamine or diisopropyethylamine, and optionally in the presence of a solvent such as ethanol, 2-methoxyethanol, toluene or acetonitrile, to provide compounds of formula (41). Compounds of formula (41) may contain a protecting group such as Boc that can be removed to provide compounds of formula (41).

Diamines of formula (50) may contain up to two different N—H groups. Diamines of formula (50) that contain two different N—H groups may selectively react with compounds of formula (49) to provide one isomer of formula (41), wherein only one of the two different N—H groups participated in the reaction. Alternatively, diamines of formula (50) that contain two different N—H groups may non-selectively react with compounds of formula (49) to provide two isomers of formula (41), wherein either of the two N—H groups participated in the reaction, Mixtures of isomers of compounds of formula (41) can be separated by methods known to those skilled in the art, such as chromatography and crystallization.

Compounds of formula (41) may contain an N—$R_{37}$ group on the cyclic amine of formula $A_1$ as defined in formula (V). Compounds of formula (41), wherein one or more of the $R_{37}$ groups of $A_1$ is hydrogen, can be reacted with an appropriate reagent such as $R_{37}$-(LG)$_3$, wherein (LG)$_3$ is a leaving group such as chlorine, bromine, iodine, mesylate, tosylate or triflate, to provide compounds of formula (I) wherein $R_{37}$ is not hydrogen.

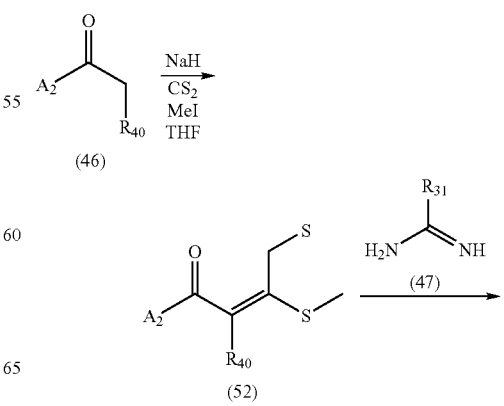

-continued

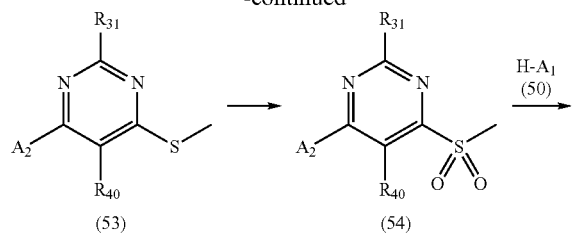

Compounds of formula (41), wherein $R_{31}$, $R_{40}$, $A_1$ and $A_2$ have been defined in formula (V) can be prepared as described in Scheme 8. Ketones of formula (46) can be reacted with carbon disulfide and iodomethane in the presence of a base such as NaH in a solvent such as THF to provide compounds of formula (52). Compounds of formula (52) can be treated with an amidate or guanidate of formula (47) to provide sulfides of formula (53). Sulfides of formula (53) can be treated with an oxidizing agent such as MCPBA or Oxone® to provide sulfones of formula (54). Sulfones of formula (54) can be treated with amines of formula (50) and heated, optionally in the presence of a base such as triethyl amine or diisopropyethylamine, and optionally in the presence of a solvent such as ethanol, 2-methoxyethanol, acetonitrile or toluene, to provide compounds of formula (41).

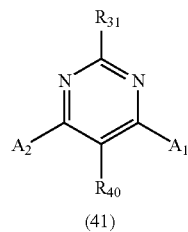

Scheme 9

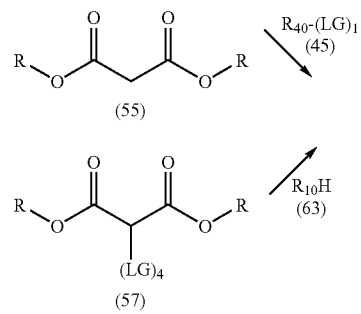

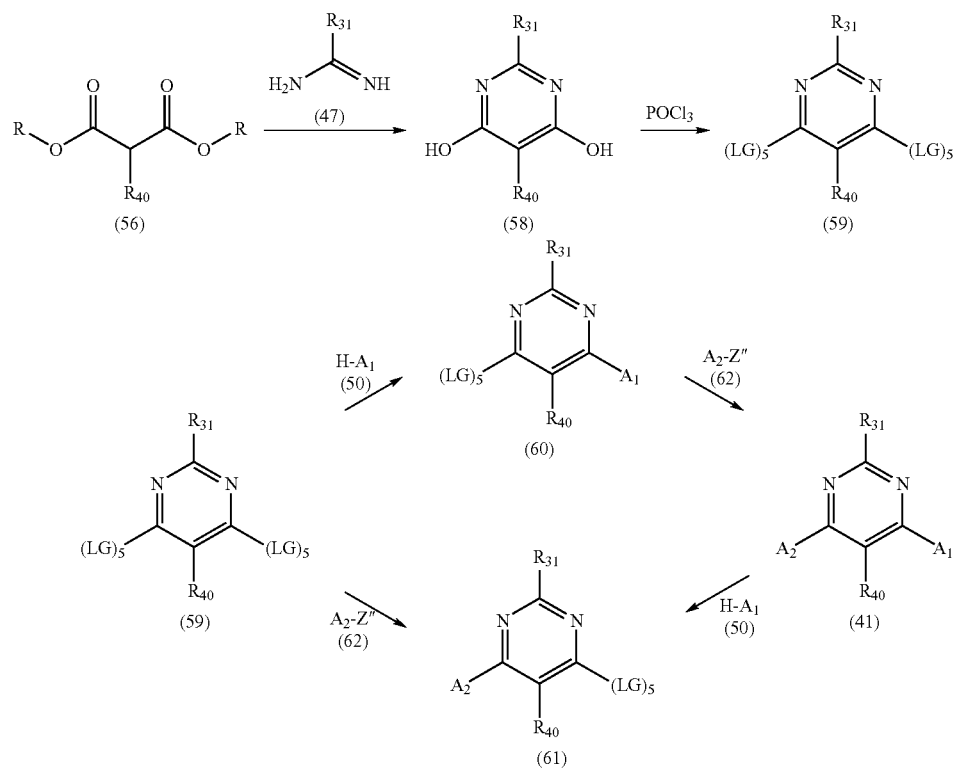

Compounds of formula (41), wherein $R_{31}$, $R_{40}$, $A_1$ and $A_2$ have been defined in formula (V) can be prepared as described in Scheme 9. Diesters of formula (55), wherein R is lower alkyl, can be alkylated or arylated with a reagent of formula (45), wherein $(LG)_1$ is a leaving group such fluorine, chlorine, bromine, iodine, mesylate or triflate, to provide diesters of formula (56). Alternatively, diesters of formula (57), wherein R is lower alkyl and $(LG)_4$ is chlorine or bromine, can be reacted with reagents of formula (63), wherein H is a hydrogen on an oxygen, sulfur or nitrogen, in the presence of a base, to provide diesters of formula (56). Diesters of formula (56) can be treated with an amidate or guanidate of formula (47), such as guanidine nitrate, in the presence of a base such as potassium carbonate and heated in a solvent such as DMF to provide 4,6-dihydroxy-pyrimidines of formula (58). Pyrimidines of formula (58) can be treated with a chlorinating reagent such as $POCl_3$ or $PCl_5$, usually with heating, to provide pyrimidines of formula (59) wherein $(LG)_5$=Cl. A base such as $Et_3N$ or dimethylaniline in a solvent such as toluene, dioxane or chloroform may be required. Pyrimidines of formula (58) can also be treated with a sulfonating reagent such as para-toluensulfonyl chloride in the presence of a base such as triethylamine and a solvent such as pyridine or chloroform to provide 2-amino-pyrimidines of formula (59) wherein $(LG)_5$=O—$SO_2$—R', wherein R' is lower alkyl, lower fluoroalkyl or aryl. Pyrimidines of formula (59), wherein $(LG)_5$=Cl or O—$SO_2$—R', can be treated with amines of formula (50), wherein H is a hydrogen on a nitrogen atom, and heated, optionally in the presence of a base such as triethylamine or diisopropyethylamine, and optionally in the presence of a solvent such as ethanol, 2-methoxyethanol, toluene or acetonitrile, to provide compounds of formula (60). Compounds of formula (60) can be treated with a reagent of general formula (62). Reagents of formula (62) include, but are not limited to organoborane reagents, wherein Z" is a borate or boronic acid, and organostannyl reagents, wherein Z" is $SnR"_3$ and wherein R" is lower alkyl. Reactions between borates and stannanes of formula (62) can be carried out under conditions of the Suzuki or Stille reaction, in the presence of a palladium catalyst such as tetrakis(triphenylphosphine)palladium and a base such as sodium carbonate and in a solvent such as 1,2-dimethoxyethane, ethanol or toluene. Reagents of formula (62) also include, but are not limited to alcohols, phenols, sulfides, amines, amides, sulfonamides and heterocycles wherein Z" is a hydrogen on an oxygen, sulfur or nitrogen atom. Reactions between amines of formula (62) wherein Z" is a hydrogen on a nitrogen can be carried out using conditions such as heating in a solvent such as 2-methoxyethane in the presence of a base such as Hunig's base at a temperature between 90 and 150° C. Reactions between hetereocycles and less reactive amines, such as anilines, of formula (62) wherein Z" is a hydrogen on a nitrogen can also be carried out using a catalyst such as copper iodide under the conditions of the Ullmann reaction in the presence of a base such as $K_2CO_3$ in a solvent such as DMF, or by using a catalyst such as tris(dibenzylideneacetone)dipalladium(0) in a solvent such as toluene using a base such as potassium tert-butoxide.

Compounds of formula (60), wherein $(LG)_5$=Cl and $R_{31}$=$NH_2$, can heated with sodium iodide in 57% hydroiodic acid to provide compounds of formula (60), wherein $(LG)_5$= iodine and $R_{31}$=$NH_2$. Compounds of formula (60), wherein $(LG)_5$=iodine, are more reactive than compounds of formula (60), wherein $(LG)_5$=Cl and can be used in the above reactions to provide compounds of formula (V).

Alternatively, compounds of formula (59) can be reacted with a reagent of formula (62) using conditions described above to provide compounds of formula (61). Compounds of formula (61) can be reacted with amines of formula (50) using conditions described above.

Examples of compounds of formula (V) include, but are not limited to, 4-tert-Butyl-6-(4-methyl-piperazin-1-yl)-pyrimidin-2-ylamine; 4-tert-Butyl-6-[4-(2-dimethylamino-ethyl)-piperazin-1-yl]-pyrimidin-2-ylamine; 4-tert-Butyl-6-[4-(3-dimethylamino-propyl)-piperazin-1-yl]-pyrimidin-2-ylamine; 4-Chloro-6-(4-methyl-piperazin-1-yl)-pyrimidin-2-ylamine; 6-tert-Butyl-N4-(2-dimethylamino-ethyl)-pyrimidine-2,4-diamine; 6-tert-Butyl-N4-(2-dimethylamino-ethyl)-N4-methyl-pyrimidine-2,4-diamine; 6-tert-Butyl-N4-(3-dimethylamino-propyl)-N4-methyl-pyrimidine-2,4-diamine; 4-tert-Butyl-6-(4-methyl-piperidin-1-yl)-pyrimidin-2-ylamine; 4-tert-Butyl-6-(4-ethyl-piperazin-1-yl)-pyrimidin-2-ylamine; 4-Methyl-6-(4-methyl-piperazin-1-yl)-pyrimidin-2-ylamine; 4-Methoxy-6-(4-methyl-piperazin-1-yl)-pyrimidin-2-ylamine; 6-(4-Methyl-piperazin-1-yl)-pyrimidine-2,4-diamine; 4,6-Bis-(4-methyl-piperazin-1-yl)-pyrimidin-2-ylamine; 4-tert-Butyl-6-(2-dimethylamino-ethoxy)-pyrimidin-2-ylamine; 4-Adamantan-1-yl-6-(4-methyl-piperazin-1-yl)-pyrimidin-2-ylamine; 4-(4-Methyl-piperazin-1-yl)-6-phenyl-pyrimidin-2-ylamine; 4-(4-Methyl-piperazin-1-yl)-pyrimidin-2-ylamine; 4-(4-Methyl-piperazin-1-yl)-6-p-tolyl-pyrimidin-2-ylamine; 4-(4-Methyl-piperazin-1-yl)-6-m-tolyl-pyrimidin-2-ylamine; 4-(4-Methyl-piperazin-1-yl)-6-o-tolyl-pyrimidin-2-ylamine; 4-(4-Methoxy-phenyl)-6-(4-methyl-piperazin-1-yl)-pyrimidin-2-ylamine; 4-(3-Methoxy-phenyl)-6-(4-methyl-piperazin-1-yl)-pyrimidin-2-ylamine; 4-(2-Methoxy-phenyl)-6-(4-methyl-piperazin-1-yl)-pyrimidin-2-ylamine; 4-(4-Chloro-phenyl)-6-(4-methyl-piperazin-1-yl)-pyrimidin-2-ylamine; 4-(3-Chloro-phenyl)-6-(4-methyl-piperazin-1-yl)-pyrimidin-2-ylamine; 4-Biphenyl-4-yl-6-(4-methyl-piperazin-1-yl)-pyrimidin-2-ylamine; 4-(4-Methyl-piperazin-1-yl)-6-naphthalen-2-yl-pyrimidin-2-ylamine; 4-(4-Methyl-piperazin-1-yl)-6-naphthalen-1-yl-pyrimidin-2-ylamine; 4-(4-Methyl-piperazin-1-yl)-6-pyridin-4-yl-pyrimidin-2-ylamine; 4-Biphenyl-3-yl-6-(4-methyl-piperazin-1-yl)-pyrimidin-2-ylamine; 4-Biphenyl-2-yl-6-(4-methyl-piperazin-1-yl)-pyrimidin-2-ylamine; 4-tert-Butyl-6-(1-methyl-1,2,3,6-tetrahydro-pyridin-4-yl)-pyrimidin-2-ylamine; 4-tert-Butyl-6-(1-methyl-piperidin-4-yl)-pyrimidin-2-ylamine; 4-tert-Butyl-6-(1,2,3,6-tetrahydro-pyridin-4-yl)-pyrimidin-2-ylamine; 2'-Methoxy-6-(4-methyl-piperazin-1-yl)-[4,5']bipyrimidinyl-2-ylamine; 5-[2-Amino-6-(4-methyl-piperazin-1-yl)-pyrimidin-4-yl]-1-methyl-1H-pyridin-2-one; 4-(6-Methoxy-pyridin-3-yl)-6-(4-methyl-piperazin-1-yl)-pyrimidin-2-ylamine; 6-(4-Methyl-piperazin-1-yl)-[4,5']bipyrimidinyl-2-ylamine; 4-(6-Fluoro-pyridin-3-yl)-6-(4-methyl-piperazin-1-yl)-pyrimidin-2-ylamine; 4-(4-Methyl-piperazin-1-yl)-6-(1-methyl-1H-pyrazol-4-yl)-pyrimidin-2-ylamine; 4-(2,6-Difluoro-pyridin-3-yl)-6-(4-methyl-piperazin-1-yl)-pyrimidin-2-ylamine; 5-[2-Amino-6-(4-methyl-piperazin-1- yl)-pyrimidin-4-yl]-nicotinonitrile; 4-(2,6-Dimethoxy-phenyl)-6-(4-methyl-piperazin-1-yl)-pyrimidin-2-ylamine; 4-(4-Methoxy-pyridin-3-yl)-6-(4-methyl-piperazin-1-yl)-pyrimidin-2-ylamine; 4-(4-Methyl-piperazin-1-yl)-6-pyrrolidin-1-yl-pyrimidin-2-ylamine; 4-Iodo-6-(4-methyl-piperazin-1-yl)-pyrimidin-2-ylamine; 4-(4-Methyl-piperazin-1-yl)-6-(4-phenyl-imidazol-1-yl)-pyrimidin-2-ylamine; 1-[2-Amino-6-(4-methyl-piperazin-1-yl)-pyrimidin-4-yl]-imidazolidin-2-one; 4-(1-Methyl-1,2,3,6-tetrahydro-pyridin-4-yl)-6-pyrrolidin-1-yl-pyrimidin-2-ylamine; 4-(1-Methyl-piperidin-4-yl)-6-pyrrolidin-1-yl-pyrimidin-2-ylamine; 4-(2,7-Diaza-spiro[3.5]non-7-yl)-pyrimidin-2-ylamine; 5-Methyl-4-(4-methyl-piperazin-1-yl)-pyrimidin-2-ylamine; 4-[2-Amino-5-methyl-6-(4-methyl-piperazin-1-yl)-pyrimidin-4-yl]-benzonitrile; 5-Methoxy-4-(4-methyl-piperazin-1-yl)-pyrimidin-2-ylamine; 4-(4-Methyl-piperazin-1-yl)-5-phenyl-pyrimidin-2-ylamine; 4-[2-Amino-5-methoxy-6-(4-methyl-piperazin-1-yl)-pyrimidin-4-yl]-benzonitrile; 4-[2-Amino-6-(4-methyl-piperazin-1-yl)-5-phenyl-pyrimidin-4-yl]-benzonitrile; 4-(4-Methyl-piperazin-1-yl)-6-(2-methylsulfanyl-phenyl)-pyrimidin-2-ylamine; 4-(4-Methyl-piperazin-1-yl)-6-(4-methylsulfanyl-phenyl)-pyrimidin-2-ylamine; 3-[2-Amino-6-(4-methyl-piperazin-1-yl)-pyrimidin-4-yl]-1,5,5-trimethyl-imidazolidine-2,4-dione; 1-[2-Amino-6-(4-methyl-piperazin-1-yl)-pyrimidin-4-yl]-3-methyl-imidazolid in-2-one; 1-[2-Amino-6-(4-methyl-piperazin-1-yl)-pyrimidin-4-yl]-3-methyl-1,3-dihydro-benzoimidazol-2-one; 1-[2-Amino-6-(4-methyl-piperazin-1-yl)-pyrimidin-4-yl]-1,3-dihydro-benzoimidazol-2-one; 6-(4-Methyl-piperazin-1-yl)-N4-phenyl-pyrimidine-2,4-diamine; N4-Methyl-6-(4-methyl-piperazin-1-yl)-N4-phenyl-pyrimidine-2,4-diamine; 4-(4-Methyl-piperazin-1-yl)-6-morpholin-4-yl-pyrimidin-2-ylamine; 4-(4-Methyl-piperazin-1-yl)-6-piperidin-1-yl-pyrimidin-2-ylamine; 4-(3-Dimethylamino-pyrrolidin-1-yl)-6-(4-methyl-piperazin-1-yl)-pyrimidin-2-ylamine; 4-(4-Methyl-piperazin-1-yl)-6-piperazin-1-yl-pyrimidin-2-ylamine; {(S)-1-[2-Amino-6-(4-methyl-piperazin-1-yl)-pyrimidin-4-yl]-pyrrolidin-2-yl}-methanol; 1-[2-Amino-6-(4-methyl-piperazin-1-yl)-pyrimidin-4-yl]-pyrrolidin-3-ol; 4-(4-Methyl-piperazin-1-yl)-6-(2-methyl-pyrrolidin-1-yl)-pyrimidin-2-ylamine; N4-Methyl-6-(4-methyl-piperazin-1-yl)-pyrimidine-2,4-diamine; N4,N4-Diethyl-6-(4-methyl-piperazin-1-yl)-pyrimidine-2,4-diamine; N4, N4-Dimethyl-6-(4-methyl-piperazin-1-yl)-pyrimidine-2,4-diamine; N4-Benzyl-N4-methyl-6-(4-methyl-piperazin-1-yl)-pyrimidine-2,4-diamine; 4-[2-Amino-6-(4-methyl-piperazin-1-yl)-pyrimidin-4-yl]-imidazole-1-sulfonic acid dimethylamide; 3-[2-Amino-6-(4-methyl-piperazin-1-yl)-pyrimidin-4-yl]-benzonitrile; 2-[2-Amino-6-(4-methyl-piperazin-1-yl)-pyrimidin-4-yl]-benzonitrile; 4-(4-Methyl-piperazin-1-yl)-6-(1H-pyrazol-4-yl)-pyrimidin-2-ylamine; 4-(1H-Imidazol-4-yl)-6-(4-methyl-piperazin-1-yl)-pyrimidin-2-ylamine; 4-(1-Methyl-1H-imidazol-4-yl)-6-(4-methyl-piperazin-1-yl)-pyrimidin-2-ylamine; 4-[2-Amino-6-((3aR,6aS)-5-methyl-hexahydro-pyrrolo[3,4-c]pyrrol-2-yl)-pyrimidin-4-yl]-benzonitrile; 4-piperazin-1-yl-6-pyridin-3-yl-pyrimidin-2-ylamine; 4-(2-Amino-6-piperazin-1-yl-pyrimidin-4-yl)-benzonitrile; 2-[2-Amino-6-(4-methyl-piperazin-1-yl)-pyrimidin-4-yl]-phenol; 4-[2-Amino-6-(4-cyclopropylmethyl-piperazin-1-yl)-pyrimidin-4-yl]-benzonitrile; [(S)-1-(2-Amino-6-piperazin-1-yl-pyrimidin-4-yl)-pyrrolidin-2-yl]-methanol; 4-(6-Methoxy-pyridin-3-yl)-6-piperazin-1-yl-pyrimidin-2-ylamine; 4-(3-Iodo-phenyl)-6-(4-methyl-piperazin-1-yl)-pyrimidin-2-ylamine; 4-(4-Iodo-phenyl)-6-(4-methyl-piperazin-1-yl)-pyrimidin-2-ylamine; 4-tert-Butyl-2-methoxy-6-(4-methyl-piperazin-1-yl)-pyrimidine; 4-tert-Butyl-6-piperidin-4-yl-pyrimidin-2-ylamine; 4-(2,6-Dimethyl-pyridin-3-yl)-6-(4-methyl-piperazin-1-yl)-pyrimidin-2-ylamine; 4-(3,5-Dimethyl-1H-pyrazol-4-yl)-6-(4-methyl-piperazin-1-yl)-pyrimidin-2-ylamine; 4-(4-Methyl-piperazin-1-yl)-6-(1,3,5-trimethyl-1H-pyrazol-4-yl)-pyrimidin-2-ylamine; 4-(2-Methoxy-pyridin-3-yl)-6-(4-methyl-piperazin-1-yl)-pyrimidin-2-ylamine; 4-Imidazol-1-yl-6-(4-methyl-piperazin-1-yl)-pyrimidin-2-ylamine; N4-Azetidin-3-yl-pyrimidine-2,4-diamine; 1-[2-Amino-6-(4-methyl-piperazin-1-yl)-pyrimidin-4-yl]-1H-pyridin-2-one; 4-(4-Chloro-imidazol-1-yl)-6-(4-methyl-piperazin-1-yl)-pyrimidin-2-ylamine; {1-[2-Amino-6-(4-methyl-piperazin-1-yl)-pyrimidin-4-yl]-1H-imidazol-4-yl}-methanol; 4-Chloro-6-(4-methyl-piperazin-1-yl)-pyrimidine-2,5-diamine; 4-Chloro-5-methyl-6-(4-methyl-piperazin-1-yl)-pyrimidin-2-ylamine; 4-(4-Methyl-piperazin-1-yl)-pyrimidine-2,5-diamine; 4-Benzoimidazol-1-yl-6-(4-methyl-piperazin-1-yl)-pyrimidin-2-ylamine; 2-[2-Amino-6-(4-methyl-piperazin-1-yl)-pyrimidin-4-yl]-2H-pyridazin-3-one; N4-Benzyl-6-(4-methyl-piperazin-1-yl)-pyrimidine-2,4-diamine; and 4-piperazin-1-yl-pyrimidin-2-ylamine.

Compounds of formula (VI) are histamine $H_4$ receptor ligands. Compounds of formula (VI)

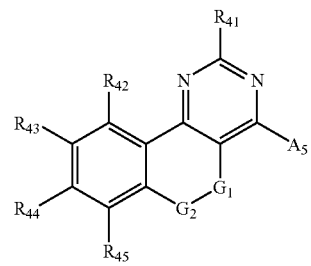

(VI)

or a pharmaceutically acceptable, salt, ester, amide, or prodrug thereof, wherein:

$G_1$ is selected from oxygen, sulfur, S(O), S(O)$_2$, NR$_{48}$ and alkylene;

$G_2$ is selected from oxygen, sulfur, S(O), S(O)$_2$, NR$_{48}$, and alkylene wherein each carbon of the alkylene and methylene groups of $G_1$ and $G_2$ may be optionally substituted with one or more groups selected from alkyl, fluoroalkyl, cyanoalkyl, cycloalkyl, fluorocycloalkyl, cycloalkoxyalkyl, alkylcycloalkyl, alkylfluorocycloalkyl, fluorine, acyl, acyloxy, alkenyl, alkoxy, alkoxyalkoxy, alkoxyalkyl, alkoxycarbonyl, alkylcarbonyl, alkylsulfonyl, alkynyl, amido, carboxy, cyano, fluoroalkoxy, formyl, haloalkoxy, haloalkyl, halogen, hydroxy, hydroxyalkyl, mercapto, nitro, alkylthio, and oxo;

provided that when $G_1$ is oxygen, sulfur, S(O), S(O)$_2$ or NR$_{48}$, $G_2$ is alkylene;

provided that when $G_2$ is oxygen, sulfur, S(O), S(O)$_2$, or NR$_{48}$, $G_1$ is alkylene;

R₁ is selected from H, NH₂, —NH(acyl), —NH(alkyl), —N(alkyl)₂, —NH(C=O)aryl, —NH-alkylene(NR₄₈R₄₉), —NH(C=O)-alkylene(NR₄₈R₄₉), —NR₄₈(C=O)NR₄₈R₄₉, —NH-alkylene-heteroaryl, —NHOH, —NHOCH₃, —O-alkylene(NR₄₈R₄₉), alkyl, piperazine, fluoroalkyl, cyanoalkyl, cycloalkyl, fluorocycloalkyl, hydroxyalkyl, cyano, alkoxycarbonyl, carboxy, —(C=O)—(NR₄₈R₄₉), —(C=O)—NH-alkylene(NR₄₈R₄₉), and alkoxy;

R₄₂, R₄₃, R₄₄, R₄₅, are each independently selected from hydrogen, alkyl, fluoroalkyl, cyanoalkyl, cycloalkyl, fluorocycloalkyl, cycloalkoxyalkyl, alkylcycloalkyl, alkylfluorocycloalkyl, aryl, heteroaryl, heterocycle, O-aryl, O-heteroaryl, S-aryl, CONR₄₈R₄₉, NR₄₈COalkyl, NR₄₈(C=O)Oalkyl, acyl, acyloxy, alkenyl, alkoxy, alkoxyalkoxy, alkoxyalkyl, alkoxycarbonyl, alkoxyimino, alkoxysulfonyl, alkylcarbonyl, alkylsulfonyl, alkynyl, amido, carboxy, cyano, fluoroalkoxy, formyl, haloalkoxy, haloalkyl, halogen, hydroxy, hydroxyalkyl, mercapto, nitro, alkylthio, —NR₄₈R₄₉, -carbonyl(NR₄₈R₄₉), —SO₂(NR₄₈R₄₉), and N(R₄₈)SO₂(R₄₉);

R₄₃ and R₄₄ taken together with the carbon atoms to which each is attached form a ring, wherein R₄₃ and R₄₄ taken together are —CH₂CH₂CH₂—, —CH₂CH₂CH₂CH₂—, or —CH₂OCH₂—;

R₄₆ is selected from hydrogen, alkyl, fluoroalkyl, cyanoalkyl, hydroxyalkyl, alkoxyalkyl, cycloalkyl, fluorocycloalkyl, cycloalkoxyalkyl, alkylcycloalkyl, and alkylfluorocycloalkyl;

R₄₇ is selected from fluoroalkyl, hydroxyalkyl, alkoxyalkyl, fluorocycloalkyl, and alkylfluorocycloalkyl;

R₄₈ and R₄₉ each are each independently selected from hydrogen, alkyl, fluoroalkyl, cycloalkyl, cyanoalkyl, fluorocycloalkyl, cycloalkoxyalkyl, alkylcycloalkyl, alkylfluorocycloalkyl, aryl, heteroaryl, heterocycle, acyl, alkoxyalkyl, alkoxycarbonyl, alkylcarbonyl, alkylsulfonyl, amido, formyl, hydroxy, and hydroxyalkyl;

A₅ is a group of structure A₇ or A₈;

wherein A₇ is selected from

A

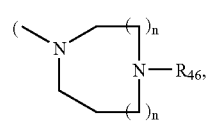

B

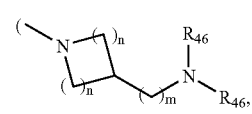

C

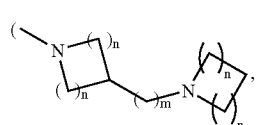

D

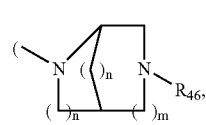

E

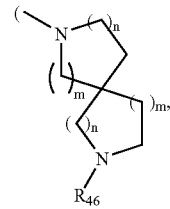

F

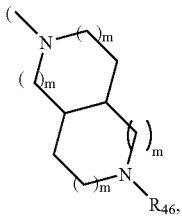

G

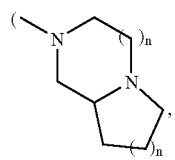

H

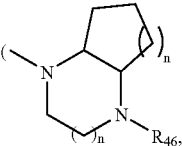

I

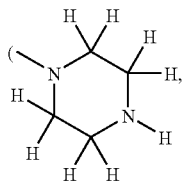

J

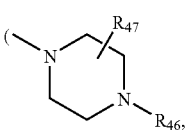

K

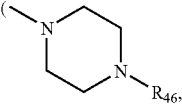

L

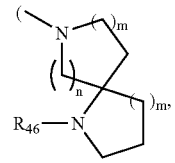

M

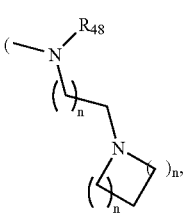

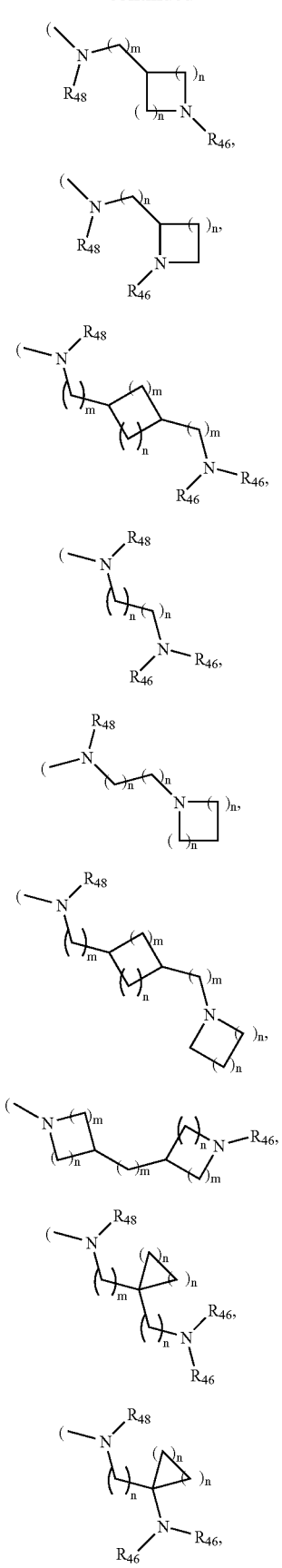
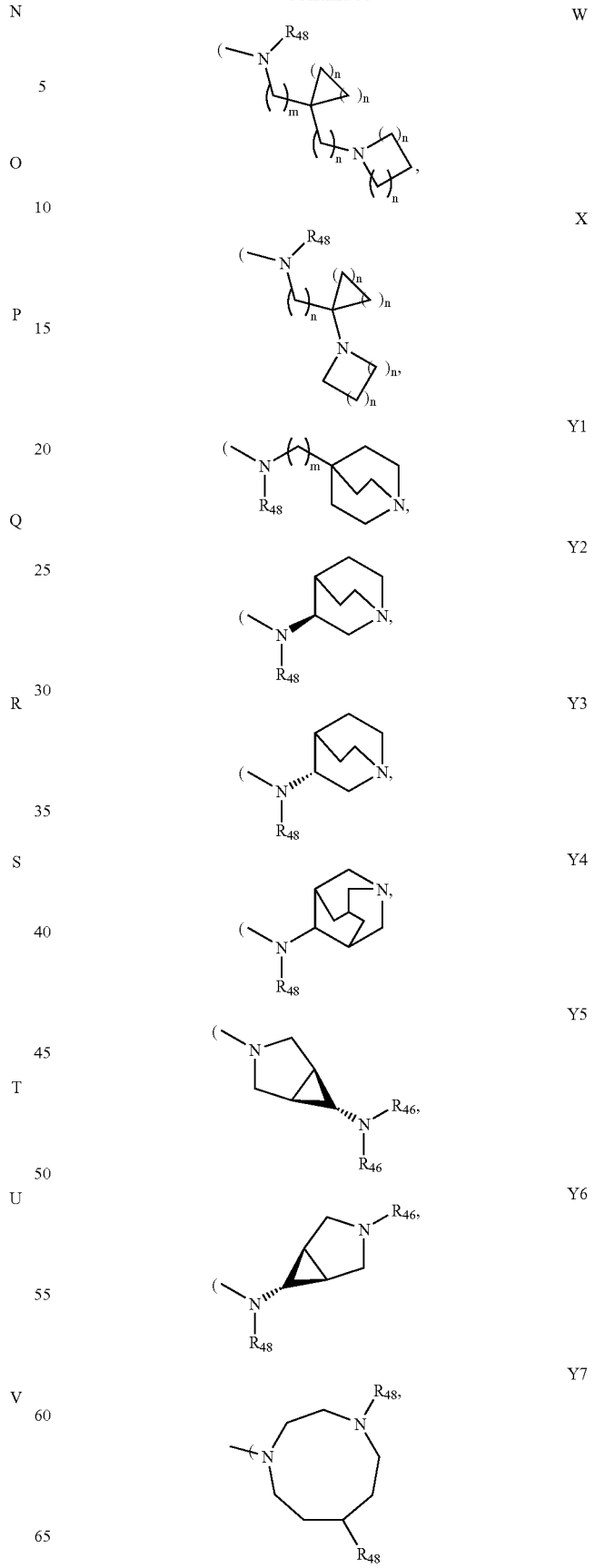

29
-continued
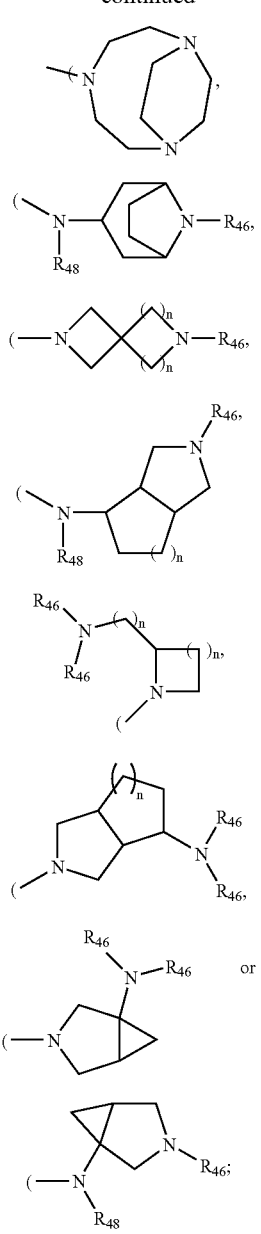
Y8
Y9
Y10
Y11
Y12
Y13
Y14
Y15
and $A_8$ is selected from
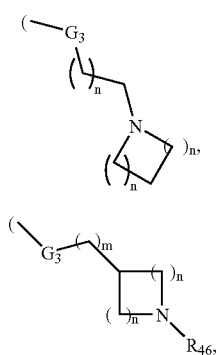
1M
1N
30
-continued
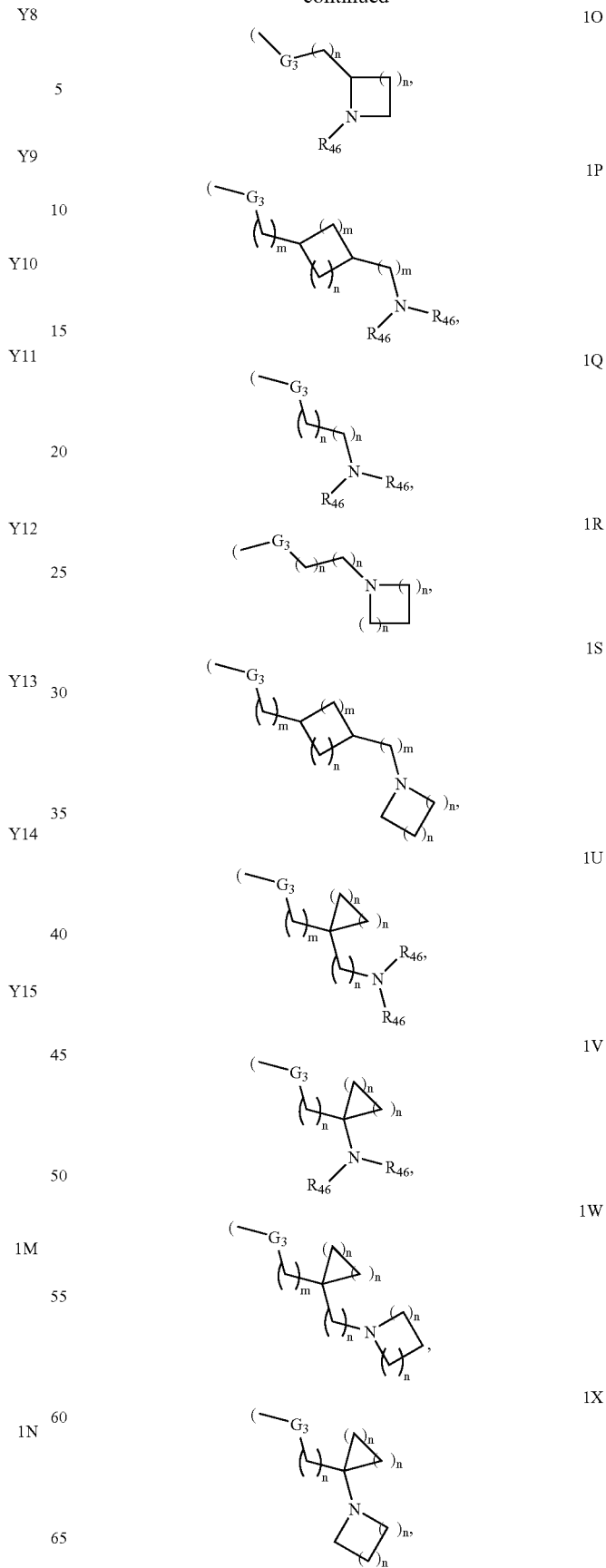
1O
1P
1Q
1R
1S
1U
1V
1W
1X

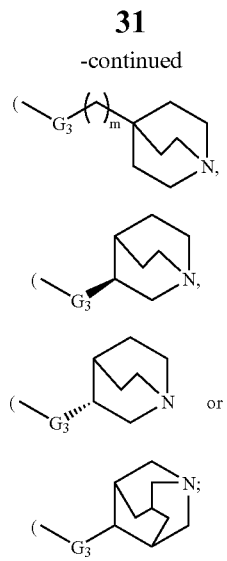

wherein $G_3$ is O, S, S(O), S(O)$_2$;

n is 1, 2, or 3;

m is 0, 1, or 2;

wherein each carbon atom of groups $A_5$ may be optionally substituted with one or more groups selected from alkyl, fluoroalkyl, cyanoalkyl, cycloalkyl, fluorocycloalkyl, cycloalkoxyalkyl, alkylcycloalkyl, alkylfluorocycloalkyl, fluorine, acyl, acyloxy, alkenyl, alkoxy, alkoxyalkoxy, alkoxyalkyl, alkoxycarbonyl, alkylcarbonyl, alkylsulfonyl, alkynyl, amido, carboxy, cyano, fluoroalkoxy, formyl, haloalkoxy, haloalkyl, halogen, hydroxy, hydroxyalkyl, mercapto, nitro, alkylthio; provided that when $G_1$ is CH$_2$ and $G_2$ is selected from CH$_2$, CH$_2$CH$_2$, oxygen or sulfur and $R_1$ is selected from NH$_2$, NHalkyl, or alkyl, then $A_5$ is not a group of structure K; and further provided that when $G_1$ is CH$_2$CH$_2$ and $G_2$ is CH$_2$ and $R_1$ is selected from NH$_2$, NHalkyl, or alkyl, then $A_5$ is not a group of structure K.

Compounds of formula (VI) can be prepared by the following synthetic methods:

Scheme 10

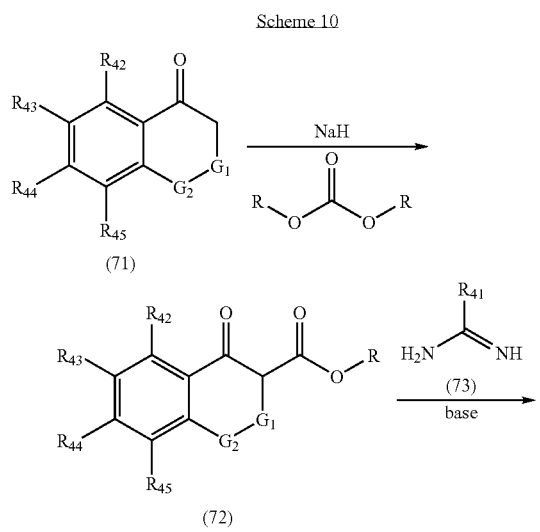

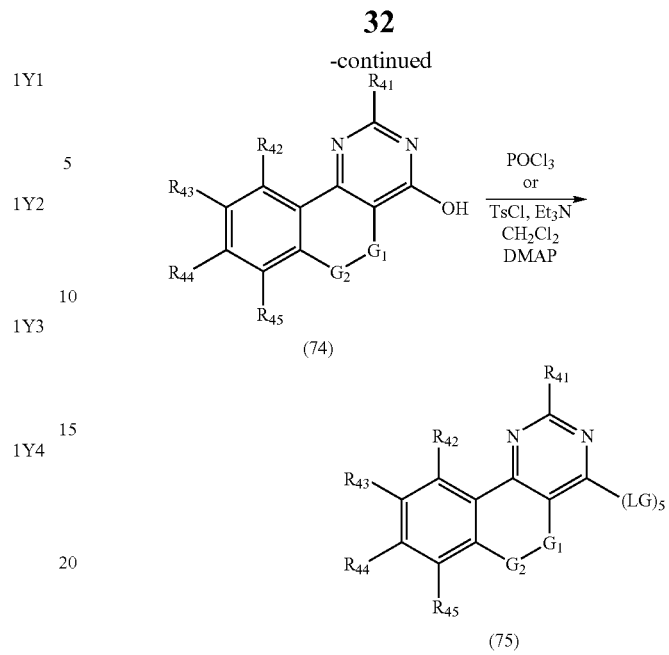

Compounds of formula (77), wherein $R_{41}$, $R_{42}$, $R_{43}$, $R_{44}$, $R_{45}$, $A_5$, $G_1$ and $G_2$ are defined in formula (VI) may be prepared as outlined in Scheme 10. Ketones of formula (71), which are obtained either from commercial sources or synthesized through the methods outlined herein, when treated with sodium hydride, followed by treatment with either a carbonate such as dimethyl carbonate, or a chloroformate such as ethyl chloroformate, will provide keto-ester containing compounds of formula (72), wherein R=lower alkyl. Compounds of formula (72) when treated with a compound of formula (73), such as guanidine nitrate, in the presence of a base such as potassium carbonate under heated conditions in a solvent such as DMF will provide compounds of formula (74). Compounds of formula (74) can exist as shown in the structure in Scheme 10 or in a tautomeric form. Compounds of formula (74) when treated with a chlorinating reagent such as, but not limited to, POCl$_3$, with or without heating as needed, will provide compounds of formula (75), wherein (LG)$_5$=Cl. Alternatively, compounds of formula (74) may also be treated with reagents such as para-toluensulfonyl chloride, methylsulfonyl chloride or trifluoromethanesulfonyl chloride in the presence of a base such as triethylamine in a solvent such as pyridine or chloroform to provide compounds of formula (75) wherein (LG)$_5$=O—SO$_2$—R', wherein R' is lower alkyl, lower fluoroalkyl or aryl. Compounds of formula (75), wherein (LG)$_5$=Cl or —O—SO$_2$—R', when treated with compounds of formula (76), wherein (76) contains a primary or secondary nitrogen atom and H is a hydrogen atom on said nitrogen atom, under heated conditions in the presence or absence of a base such as triethylamine or diisopropyethylamine, in a solvent such as ethanol, 2-methoxyethanol, toluene or acetonitrile, will provide compounds of formula (77).

Compounds of formula (77) wherein $R_{41}$=H and $R_{42}$, $R_{43}$, $R_{44}$, $R_{45}$, $G_1$ and $G_2$ are defined in formula (VI) may be prepared by treating a compound of formula (72) with thiourea with heating in the presence of a base such as sodium methoxide in a solvent such as methanol, followed by reduction of the resulting product using a reagent such as Raney nickel to provide compounds of formula (74) wherein $R_{41}$=H. Compounds of formula (74) wherein $R_{41}$=H can be treated according to the method above to provide compounds of formula (77) wherein $R_{41}$=H.

Compounds of formula (77), may be further treated according to conditions known to one skilled in the art to alter functional groups contained with in the compound, for example, the removal of a protecting group such as Boc or hydrolysis of an ester group that will generate compounds of the present invention or used within the scope of other schemes described herein.

Compounds of formula (76) that contain two different nitrogen atoms may selectively react with compounds of formula (75) to provide one isomer of formula (77). Such selectivity may be the result of substitution or protecting groups attached to one of the nitrogen atoms. Alternatively, compounds of formula (76) that contain two different N—H groups may react with compounds of formula (75) in a non-selective manner wherein a mixture of two different compounds of formula (77) are obtained from the reaction. Mixtures of compounds of formula (77) are generally separated by methods known to one skilled in the art, such as silica based column chromatography and/or selective recrystallization.

Compounds of formula (77) generated through the methods outlined in Scheme 10, may contain a Br, I or —O-Tf functional group in one of the positions represented by $R_{42}$, $R_{43}$, $R_{44}$ or $R_{45}$. These functional groups may be utilized as a site for introducing a carbon or nitrogen atom containing substituent at that position. Such reactions are known to one skilled in the art. For example, compounds of formula (77), containing a Br, I or O-Tf functional group in one of the positions represented by $R_{42}$, $R_{43}$, $R_{44}$ or $R_{45}$ when treated with an aryl or heteroaryl boronic acids or boronic esters according to the conditions known to one skilled in the art as the Suzuki reaction will provide compounds wherein the Br, I or O-Tf has been replaced by an aryl or heteroaryl group. Alternatively, using the Stille coupling reaction, compounds of formula (77) wherein one of $R_{42}$, $R_{43}$, $R_{44}$ or $R_{45}$ is Br, I or O-Tf, when treated with a vinyl, aryl or heteroaryl stannanes will provide compounds wherein the Br, I or O-Tf has been replaced by the vinyl, aryl or heteroaryl group. Alternatively, compounds of formula (77) wherein one of $R_{42}$, $R_{43}$, $R_{44}$ or $R_{45}$ is Br, I or O-Tf, when treated with amines, heterocycles or heteroaryls containing an NH group will provide compounds of wherein the Br, I or O-Tf has been replaced by the amine, heterocycle or heteroaryl group. Procedures and condition describing these transformations may be found in the following references: J. Hartwig et al., Angew. Chem. Int. Ed. 37:2046-2067 (1998); J. P. Wolfe et al., Acc. Chem. Res., 13:805-818 (1998); M. Sugahara et al., Chem. Pharm. Bull., 45:719-721 (1997); J. P. Wolfe et al., J. Org. Chem., 65:1158-1174, (2000); F. Y. Kwong et al., Org. Lett., 4:581-584, (2002); A. Klapars et al., J. Amer. Chem. Soc., 123:7727-7729 (2001); B. H. Yang et al., J. Organomet. Chem., 576:125-146 (1999); A. Kiyomori et al., Tet. Lett., 40:2657-2640 (1999); and Hartwig, J. Org. Chem., 64(15):5575-5580 (1999). Alternatively, compounds of formula (77) wherein one of $R_{42}$, $R_{43}$, $R_{44}$ or $R_{45}$ is Br, I or O-Tf, may be subjected to conditions commonly known as the Heck and Sonogashira reaction, to introduce an alkene or alkyne group at the site of the Br, I or O-Tf moiety.

Scheme 11

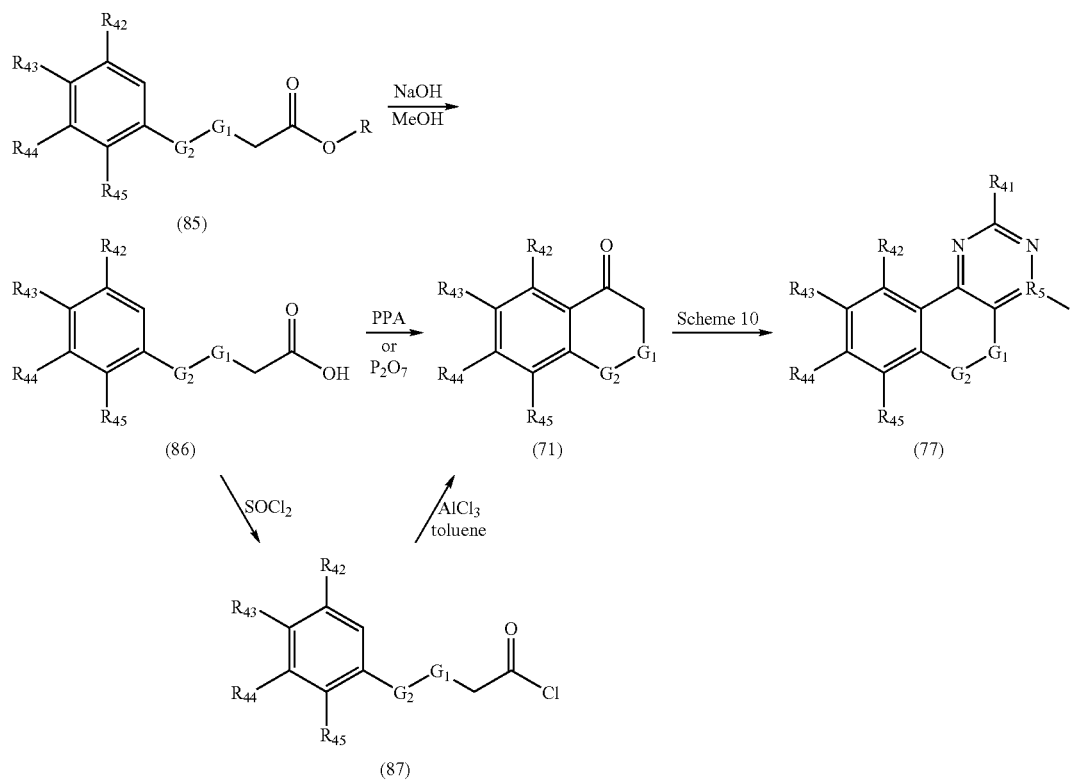

Compounds of formula (77), which are representative of compounds of general formula (VI) wherein $R_{41}$, $R_{42}$, $R_{43}$, $R_{44}$, $R_{45}$, $A_5$, $G_1$ and $G_2$ are as defined in formula (VI), may be prepared as outlined in Scheme 11. Compounds of formula (85), wherein R is lower alkyl or benzyl as obtained from commercial sources of prepared by one skilled in the art, when treated with either sodium, lithium or potassium hydroxide in a mixture of aqueous alcohol such as aqueous methanol or ethanol will provide compounds of formula (86). Compounds of formula (86) when heated in the presence of an acid such as polyphosphoric acid or heated in the presence of $P_2O_5$ (phosphorus pentoxide), will provide compounds of formula (71). Alternatively, compounds of formula (86) when treated with thionyl chloride under heated conditions will provide compounds of formula (87). Compounds of formula (87) when heated in the presence of a Lewis acid such as aluminum trichloride in a solvent such as toluene or carbon disulfide will provide compounds of formula (71). The compounds of formula (71) can be treated according to the methods outlined in Scheme 10 to provide compounds of formula (77).

Compounds of formula (77), which are representative of compounds of general formula (VI) wherein $R_{41}$, $R_{42}$, $R_{43}$, $R_{44}$, $R_{45}$ and $A_5$ are defined in formula (VI), $G_1$ is alkylene, and $G_2$=O, S, $NR_{48}$ or $NR^a$, $R^a$ is hydrogen, alkyl or a nitrogen protecting group such as Boc, alkylsulfonyl, arylsulfonyl or phosphate, may be prepared as outlined in Scheme 12. Compounds of formula (89), wherein $G_2$=O, S, $NR_{48}$ or $NR_a$, wherein $R_a$ is hydrogen, alkyl or a nitrogen protecting group such as Boc, alkylsulfonyl, arylsulfonyl or phosphate, when treated with an ester of formula (90) wherein R is lower alkyl, $G_1$ is alkylene, and wherein $(LG)_6$ is chloro, bromo, iodo or methanesulfonyl, in the presence of a base such as $K_2CO_3$, $Et_3N$ or sodium hydride, in a solvent such as acetone, $CH_2Cl_2$ or THF, will provide compounds of formula (85). Compounds of formula (85) when heated in the presence of an acid such as polyphosphoric acid or heated in the presence of $P_2O_5$, or subjected to conditions such as described in Scheme 11 can be cyclized to provide compounds of formula (71). Compounds of formula (71) when processed as outlined in Scheme 10 will provide compounds of formula (57), which are representative of compounds of general formula (VI).

Scheme 12

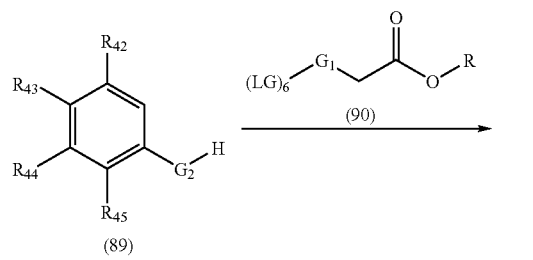

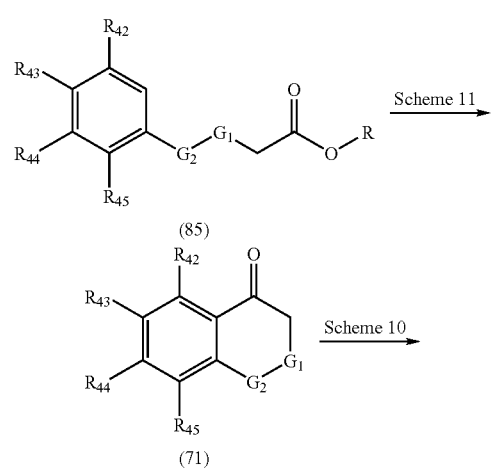

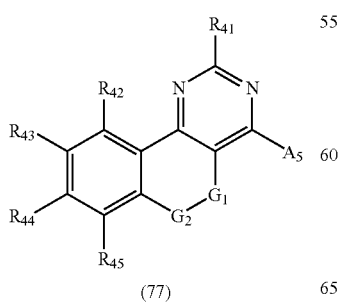

Scheme 13

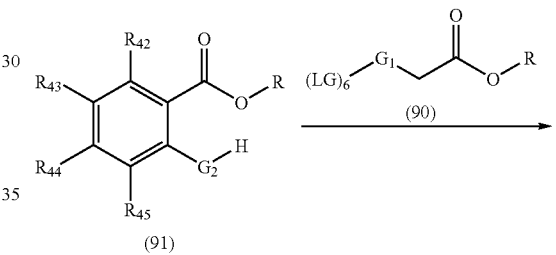

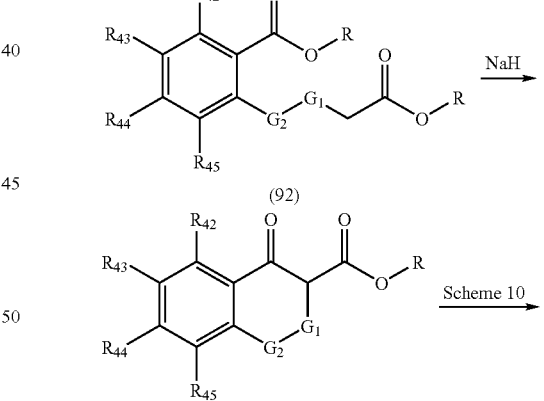

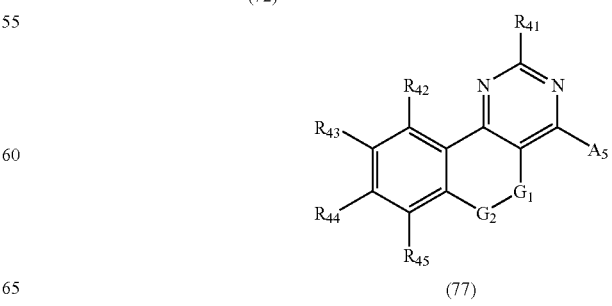

Compounds of formula (77), which are representative of compounds of the present invention wherein $R_{41}$, $R_{42}$, $R_{43}$, $R_{44}$, $R_{45}$ and $A_5$ have been defined in formula (VI), wherein $G_1$ is alkylene, and wherein $G_2$=O, S, $NR_{48}$ or $NR_a$, wherein $R_a$ is hydrogen, alkyl or a nitrogen protecting group such as Boc, alkylsulfonyl, arylsulfonyl or phosphate, may be prepared as outlined in Scheme 13. Compounds of formula (91), wherein R is lower alkyl, $G_2$=O, S, $NR_{48}$ or $NR_a$, wherein $R_a$ is hydrogen, alkyl or a nitrogen protecting group such as Boc, alkylsulfonyl, arylsulfonyl or phosphate, when treated with a compound of formula (90) wherein $G_1$ is $C_{1-5}$ alkylene, R is lower alkyl, and wherein $(LG)_6$ is a leaving group such as chloro, bromo, iodo or methanesulfonyl, in the presence of a base such as $K_2CO_3$, $Et_3N$ or sodium hydride, in a solvent such as acetone, $CH_2Cl_2$, DMF or THF, will provide compounds of formula (92). Compounds of formula (92) when treated with a base such as sodium hydride in a solvent such as THF will provide compounds of formula (72). Compounds of formula (72) when treated as outlined in Scheme 10 will provide compounds of formula (77), which are representative of compounds of formula (VI) wherein $G_1$ is alkylene and $G_2$ is O, S, $NR_{48}$ or $NR_a$.

Preferred examples of compounds of formula (VI) include, but are not limited to 6-methyl-4-[(3R)-3-methylamino-pyrrolidin-1-yl]-5,6-dihydro-benzo[h]quinazolin-2-ylamine; 6-methyl-4-(3-methylamino-azetidin-1-yl)-5,6-dihydro-benzo[h]quinazolin-2-ylamine; 4-(3-methylamino-azetidin-1-yl)-6,7-dihydro-5H-benzo[6,7]cyclohepta[1,2-d]pyrimidin-2-ylamine; 6-methyl-4-piperazin-1-yl-5,6-dihydro-benzo[h]quinazolin-2-ylamine; 4-(3-(R)-methylamino-pyrrolidin-1-yl)-6,7-dihydro-5H-benzo[6,7]cyclohepta[1,2-d]pyrimidin-2-ylamine; 4-piperazin-1-yl-6,7-dihydro-5H-benzo[6,7]cyclohepta[1,2-d]pyrimidin-2-ylamine; 1-(3-methylamino-azetidin-1-yl)-10H-9-oxa-2,4-diaza-phenanthren-3-ylamine; 1-(3-(R)-methylamino-pyrrolidin-1-yl)-10H-9-oxa-2,4-diaza-phenanthren-3-ylamine; 1-piperazin-1-yl-10H-9-oxa-2,4-diaza-phenanthren-3-ylamine; 10-fluoro-4-(3-(R)-methylamino-pyrrolidin-1-yl)-6,7-dihydro-5H-benzo[6,7]cyclohepta[1,2-d]pyrimidin-2-ylamine; 10-fluoro-4-(3-methylamino-azetidin-1-yl)-6,7-dihydro-5H-benzo[6,7]cyclohepta[1,2-d]pyrimidin-2-ylamine; 10-fluoro-4-piperazin-1-yl-6,7-dihydro-5H-benzo[6,7]cyclohepta[1,2-d]pyrimidin-2-ylamine; 4-[(3S)-3-methylamino-pyrrolidin-1-yl]-6,7-dihydro-5H-benzo[6,7]cyclohepta[1,2-d]pyrimidin-2-ylamine; 4-((3aR,6aR)-1-methyl-hexahydro-pyrrolo[3,4-b]pyrrol-5-yl)-6,7-dihydro-5H-benzo[6,7]cyclohepta[1,2-d]pyrimidin-2-ylamine; 4-((3R)-3-amino-pyrrolidin-1-yl)-6,7-dihydro-5H-benzo[6,7]cyclohepta[1,2-d]pyrimidin-2-ylamine; 4-((1S,4S)-2,5-diaza-bicyclo[2.2.1]hept-2-yl)-6,7-dihydro-5H-benzo[6,7]cyclohepta[1,2-d]pyrimidin-2-ylamine; 4-(3-piperidin-1-yl-pyrrolidin-1-yl)-6,7-dihydro-5H-benzo[6,7]cyclohepta[1,2-d]pyrimidin-2-ylamine; 4-((3aR,6aR)-hexahydro-pyrrolo[3,4-b]pyrrol-1-yl)-6,7-dihydro-5H-benzo[6,7]cyclohepta[1,2-d]pyrimidin-2-ylamine; 4-piperazin-1-yl-5,6,7,8-tetrahydro-1,3-diaza-dibenzo[a,c]cycloocten-2-ylamine; 4-piperazin-1-yl-6,7,8,9-tetrahydro-5H-1,3-diaza-dibenzo[a,c]cyclononen-2-ylamine; 4-(hexahydro-pyrrolo[3,4-c]pyrrol-2-yl)-6,7-dihydro-5H-benzo[6,7]cyclohepta[1,2-d]pyrimidin-2-ylamine; 4-(3-(R)-methylamino-pyrrolidin-1-yl)-6,7,8,9-tetrahydro-5H-1,3-diaza-dibenzo[a,c]cyclononen-2-ylamine; 4-((R)-3-amino-pyrrolidin-1-yl)-6,7,8,9-tetrahydro-5H-1,3-diaza-dibenzo[a,c]cyclononen-2-ylamine; 4-((S)-3-amino-pyrrolidin-1-yl)-6,7,8,9-tetrahydro-5H-1,3-diaza-dibenzo[a,c]cyclononen-2-ylamine; 4-(3-methylamino-azetidin-1-yl)-6,7,8,9-tetrahydro-5H-1,3-diaza-dibenzo[a,c]cyclononen-2-ylamine; 4-((3aS,6aS)-hexahydro-pyrrolo[3,4-b]pyrrol-1-yl)-6,7,8,9-tetrahydro-5H-1,3-diaza-dibenzo[a,c]cyclononen-2-ylamine; 4-((1S,4S)-2,5-diaza-bicyclo[2.2.1]hept-2-yl)-6,7,8,9-tetrahydro-5H-1,3-diaza-dibenzo[a,c]cyclononen-2-ylamine; 4-(4-methyl-piperazin-1-yl)-5,6-dihydro-7-oxa-1,3-diaza-dibenzo[a,c]cyclohepten-2-ylamine; 4-piperazin-1-yl-5,6-dihydro-7-oxa-1,3-diaza-dibenzo[a,c]cyclohepten-2-ylamine; 4-((R)-3-methylamino-pyrrolidin-1-yl)-5,6-dihydro-7-oxa-1,3-diaza-dibenzo[a,c]cyclohepten-2-ylamine; 4-(3-methylamino-azetidin-1-yl)-5,6-dihydro-7-oxa-1,3-diaza-dibenzo[a,c]cyclohepten-2-ylamine; 4-(3-methylamino-azetidin-1-yl)-5,6-dihydro-7-thia-1,3-diaza-dibenzo[a,c]cyclohepten-2-ylamine; 4-(3-(R)-methylamino-pyrrolidin-1-yl)-5,6-dihydro-7-thia-1,3-diaza-dibenzo[a,c]cyclohepten-2-ylamine; 4-(3-(R)-amino-pyrrolidin-1-yl)-5,6-dihydro-7-thia-1,3-diaza-dibenzo[a,c]cyclohepten-2-ylamine; 4-piperazin-1-yl-5,6-dihydro-7-thia-1,3-diaza-dibenzo[a,c]cyclohepten-2-ylamine; 4-(3-methylamino-azetidin-1-yl)-7-oxo-6,7-dihydro-5H-7λ4-thia-1,3-diaza-dibenzo[a,c]cyclohepten-2-ylamine; 4-(3-methylamino-azetidin-1-yl)-7,7-dioxo-6,7-dihydro-5H-7λ6-thia-1,3-diaza-dibenzo[a,c]cyclohepten-2-ylamine; 4-(3-(R)-methylamino-pyrrolidin-1-yl)-5,6-dihydro-benzo[h]quinazolin-2-ylamine; 4-(3-methylamino-azetidin-1-yl)-5,6-dihydro-benzo[h]quinazolin-2-ylamine; 4-piperazin-1-yl-5,6-dihydro-benzo[h]quinazolin-2-ylamine; 10-chloro-4-[(3R)-3-(methylamino)pyrrolidin-1-yl]-5,6-dihydro[1]benzoxepino[5,4-d]pyrimidin-2-amine; 10-methyl-4-[(3R)-3-(methylamino)pyrrolidin-1-yl]-5,6-dihydro[1]benzoxepino[5,4-d]pyrimidin-2-amine; 10-methoxy-4-[(3R)-3-(methylamino)pyrrolidin-1-yl]-5,6-dihydro[1]benzoxepino[5,4-d]pyrimidin-2-amine; 9-chloro-4-[(3R)-3-(methylamino)pyrrolidin-1-yl]-5,6-dihydro[1]benzoxepino[5,4-d]pyrimidin-2-amine; 9-methyl-4-[(3R)-3-(methylamino)pyrrolidin-1-yl]-5,6-dihydro[1]benzoxepino[5,4-d]pyrimidin-2-amine; 9-methoxy-4-[(3R)-3-(methylamino)pyrrolidin-1-yl]-5,6-dihydro[1]benzoxepino[5,4-d]pyrimidin-2-amine; 8-chloro-4-[(3R)-3-(methylamino)pyrrolidin-1-yl]-5,6-dihydro[1]benzoxepino[5,4-d]pyrimidin-2-amine; 8-methyl-4-((R)-3-methylamino-pyrrolidin-1-yl)-5,6-dihydro-7-oxa-1,3-diaza-dibenzo[a,c]cyclohepten-2-ylamine; 8-methoxy-4-[(3R)-3-(methylamino)pyrrolidin-1-yl]-5,6-dihydro[1]benzoxepino[5,4-d]pyrimidin-2-amine; 4-[(3R)-3-(methylamino)pyrrolidin-1-yl]-5,6,7,8-tetrahydrobenzo[7,8]cycloocta[1,2-d]pyrimidin-2-amine; 4-[(3R)-3-aminopyrrolidin-1-yl]-5,6,7,8-tetrahydrobenzo[7,8]cycloocta[1,2-d]pyrimidin-2-amine; 4-[(3S)-3-aminopyrrolidin-1-yl]-5,6,7,8-tetrahydrobenzo[7,8]cycloocta[1,2-d]pyrimidin-2-amine; 4-(3-aminoazetidin-1-yl)-5,6,7,8-tetrahydrobenzo[7,8]cycloocta[1,2-d]pyrimidin-2-amine; 4-[(3aR,6aR)-hexahydropyrrolo[3,4-b]pyrrol-1(2H)-yl]-5,6,7,8-tetrahydrobenzo[7,8]cycloocta[1,2-d]pyrimidin-2-amine; 4-octahydro-6H-pyrrolo[3,4-b]pyridin-6-yl-6,7-dihydro-5H-benzo[6,7]cyclohepta[1,2-d]pyrimidin-2-amine; 4-(2,8-diazaspiro[4.5]

dec-8-yl)-6,7-dihydro-5H-benzo[6,7]cyclohepta[1,2-d]pyrimidin-2-amine; 4-(1,5-diazocan-1-yl)-6,7-dihydro-5H-benzo[6,7]cyclohepta[1,2-d]pyrimidin-2-amine; 4-(4-aminopiperidin-1-yl)-6,7-dihydro-5H-benzo[6,7]cyclohepta[1,2-d]pyrimidin-2-amine; $N^4$-(2-azetidin-2-ylethyl)-6,7-dihydro-5H-benzo[6,7]cyclohepta[1,2-d]pyrimidine-2,4-diamine; N4-[(2R)-azetidin-2-ylmethyl]-6,7-dihydro-5H-benzo[6,7]cyclohepta[1,2-d]pyrimidine-2,4-diamine; $N^4$-(1-methylpiperidin-4-yl)-6,7-dihydro-5H-benzo[6,7]cyclohepta[1,2-d]pyrimidine-2,4-diamine; $N^4$-[(1R,5S)-8-methyl-8-azabicyclo[3.2.1]oct-3-yl]-6,7-dihydro-5H-benzo[6,7]cyclohepta[1,2-d]pyrimidine-2,4-diamine; 4-(5-methyl-1,4-diazepan-1-yl)-6,7-dihydro-5H-benzo[6,7]cyclohepta[1,2-d]pyrimidin-2-amine; 4-(1-methyl-piperidin-4-yloxy)-6,7-dihydro-5H-benzo[6,7]cyclohepta[1,2-d]pyrimidin-2-ylamine; 4-(1-methyl-piperidin-3-yloxy)-6,7-dihydro-5H-benzo[6,7]cyclohepta[1,2-d]pyrimidin-2-ylamine; 4-((R)-1-methyl-pyrrolidin-3-yloxy)-6,7-dihydro-5H-benzo[6,7]cyclohepta[1,2-d]pyrimidin-2-ylamine; 4-((S)-1-methyl-pyrrolidin-3-yloxy)-6,7-dihydro-5H-benzo[6,7]cyclohepta[1,2-d]pyrimidin-2-ylamine; 4-(piperidin-4-yloxy)-6,7-dihydro-5H-benzo[6,7]cyclohepta[1,2-d]pyrimidin-2-ylamine; 4-((S)-pyrrolidin-3-yloxy)-6,7-dihydro-5H-benzo[6,7]cyclohepta[1,2-d]pyrimidin-2-ylamine; 4-(2-dimethylamino-ethoxy)-6,7-dihydro-5H-benzo[6,7]cyclohepta[1,2-d]pyrimidin-2-ylamine; 4-(1,9-diaza-spiro[5.5]undec-9-yl)-6,7-dihydro-5H-benzo[6,7]cyclohepta[1,2-d]pyrimidin-2-ylamine; 4-((R)-3-dimethylamino-pyrrolidin-1-yl)-6,7-dihydro-5H-benzo[6,7]cyclohepta[1,2-d]pyrimidin-2-ylamine; 4-(2,6diaza-spiro[3.5]non-2-yl)-6,7-dihydro-5H-benzo[6,7]cyclohepta[1,2-d]pyrimidin-2-ylamine; 4-(2,5-diaza-spiro[3.5]non-2-yl)-6,7-dihydro-5H-benzo[6,7]cyclohepta[1,2-d]pyrimidin-2-ylamine; 4-(octahydro-pyrrolo[3,4-c]pyridin-2-yl)-6,7-dihydro-5H-benzo[6,7]cyclohepta[1,2-d]pyrimidin-2-ylamine; 4-(octahydro-pyrrolo[1,2-a]pyrazin-2-yl)-6,7-dihydro-5H-benzo[6,7]cyclohepta[1,2-d]pyrimidin-2-ylamine; 4-(3,6-diaza-bicyclo[3.2.1]oct-6-yl)-6,7-dihydro-5H-benzo[6,7]cyclohepta[1,2-d]pyrimidin-2-ylamine; 4-(2,6-diaza-bicyclo[3.2.1]oct-2-yl)-6,7-dihydro-5H-benzo[6,7]cyclohepta[1,2-d]pyrimidin-2-ylamine; N-(4-piperazin-1-yl-6,7-dihydro-5H-benzo[6,7]cyclohepta[1,2-d]pyrimidin-2-yl)-acetamide; N-(4-piperazin-1-yl-6,7-dihydro-5H-benzo[6,7]cyclohepta[1,2-d]pyrimidin-2-yl)-benzamide; 4-(5-methyl-octahydro-pyrrolo[3,4-c]pyridin-2-yl)-6,7-dihydro-5H-benzo[6,7]cyclohepta[1,2-d]pyrimidin-2-ylamine; 4-(3-methyl-3,6-diaza-bicyclo[3.2.1]oct-6-yl)-6,7-dihydro-5H-benzo[6,7]cyclohepta[1,2-d]pyrimidin-2-ylamine; 2-Dimethylamino-N-(4-piperazin-1-yl-6,7-dihydro-5H-benzo[6,7]cyclohepta[1,2-d]pyrimidin-2-yl)-acetamide; 2-methylamino-N-(4-piperazin-1-yl-6,7-dihydro-5H-benzo[6,7]cyclohepta[1,2-d]pyrimidin-2-yl)-acetamide; 2-Amino-N-(4-piperazin-1-yl-6,7-dihydro-5H-benzo[6,7]cyclohepta[1,2-d]pyrimidin-2-yl)-acetamide; 1-methyl-3-(4-piperazin-1-yl-6,7-dihydro-5H-benzo[6,7]cyclohepta[1,2-d]pyrimidin-2-yl)-urea; 4-Amino-N-(4-piperazin-1-yl-6,7-dihydro-5H-benzo[6,7]cyclohepta[1,2-d]pyrimidin-2-yl)-butyramide; 6-(2-pyridin-3-ylmethylamino-6,7-dihydro-5H-benzo[6,7]cyclohepta[1,2-d]pyrimidin-4-yl)octahydro-1H-pyrrolo[3,4-b]pyridine; 3-amino-N-(4-piperazin-1-yl-6,7-dihydro-5H-benzo[6,7]cyclohepta[1,2-d]pyrimidin-2-yl)-propionamide; 4-[1,4,7]triazonan-1-yl-6,7-dihydro-5H-benzo[6,7]cyclohepta[1,2-d]pyrimidin-2-ylamine; N,N-dimethyl-N'-(4-piperazin-1-yl-6,7-dihydro-5H-benzo[6,7]cyclohepta[1,2-d]pyrimidin-2-yl)-ethane-1,2-diamine; 4-(octahydro-pyrrolo[3,4-b]pyridin-6-yl)-5,6-dihydro-7-thia-1,3-diaza-dibenzo[a,c]cyclohepten-2-ylamine; 4-((R)-3-methylamino-pyrrolidin-1-yl)-6,7,9,10,11,12-hexahydro-5H-1,3-diaza-benzo[3,4]cyclohepta[1,2-b]naphthalen-2-ylamine; 4-(octahydro-pyrrolo[3,4-b]pyridin-6-yl)-6,7,9,10,11,12-hexahydro-5H-1,3-diaza-benzo[3,4]cyclohepta[1,2-b]naphthalen-2-ylamine; 4-piperazin-1-yl-6,7,9,10,11,12-hexahydro-5H-1,3-diaza-benzo[3,4]cyclohepta[1,2-b]naphthalen-2-ylamine; 9-iodo-4-((R)-3-methylamino-pyrrolidin-1-yl)-5,6-dihydro-7-oxa-1,3-diaza-dibenzo[a,c]cyclohepten-2-ylamine; 9-iodo-4-piperazin-1-yl-5,6-dihydro-7-oxa-1,3-diaza-dibenzo[a,c]cyclohepten-2-ylamine; 9-iodo-4-octahydro-pyrrolo[3,4-b]pyridin-6-yl)-5,6-dihydro-7-oxa-1,3-diaza-dibenzo[a,c]cyclohepten-2-ylamine; 2,4-d]-piperazin-1-yl-6,7-dihydro-5H-benzo[6,7]cyclohepta[1,2-d]pyrimidine; 2-amino-4-octahydro-pyrrolo[3,4-b]pyridin-6-yl-5,6-dihydro-7-oxa-1,3-diaza-dibenzo[a,c]cycloheptene-9-carbonitrile; 4-octahydro-pyrrolo[3,4-b]pyridin-6-yl-9-phenyl-5,6-dihydro-7-oxa-1,3-diaza-dibenzo[a,c]cyclohepten-2-ylamine; 4-octahydro-pyrrolo[3,4-b]pyridin-6-yl-9-pyridin-3-yl-5,6-dihydro-7-oxa-1,3-diaza-dibenzo[a,c]cyclohepten-2-ylamine; 4-((R)-3-methylamino-pyrrolidin-1-yl)-6,7-dihydro-5-thia-1,3-diaza-dibenzo[a,c]cyclohepten-2-ylamine; 2-amino-4-octahydro-pyrrolo[3,4-b]pyridin-6-yl-5,6-dihydro-7-oxa-1,3-diaza-dibenzo[a,c]cycloheptene-9-carboxylic acid methyl ester; 4-piperazin-1-yl-6,7-dihydro-5-thia-1,3-diaza-dibenzo[a,c]cyclohepten-2-ylamine; 4-(octahydro-pyrrolo[3,4-b]pyridin-6-yl)-6,7-dihydro-5-thia-1,3-diaza-dibenzo[a,c]cyclohepten-2-ylamine; 4-((R)-3-methylamino-pyrrolidin-1-yl)-5,5-dioxo-6,7-dihydro-5H-5λ6-thia-1,3-diaza-dibenzo[a,c]cyclohepten-2-ylamine; 4-((R)-3-methylamino-pyrrolidin-1-yl)-5-oxo-6,7-dihydro-5-thia-1,3-diaza-dibenzo[a,c]cyclohepten-2-ylamine; $N^4$-(3-piperidin-1-yl-propyl)-6,7-dihydro-5H-benzo[6,7]cyclohepta[1,2-d]pyrimidine-2,4-diamine; 4-(4-dimethylamino-piperidin-1-yl)-6,7-dihydro-5H-benzo[6,7]cyclohepta[1,2-d]pyrimidin-2-ylamine; 10-fluoro-4-octahydro-6H-pyrrolo[3,4-b]pyridin-6-yl-6,7-dihydro-5H-benzo[6,7]cyclohepta[1,2-d]pyrimidin-2-amine; 4-[1,4]diazepan-1-yl-6,7-dihydro-5H-benzo[6,7]cyclohepta[1,2-d]pyrimidin-2-ylamine; (1R,5S)-4-(3,6-Diaza-bicyclo[3.2.0]hept-6-yl)-6,7-dihydro-5H-benzo[6,7]cyclohepta[1,2-d]pyrimidin-2-ylamine; 4-piperazin-1-yl-6,7-dihydro-5H-benzo[6,7]cyclohepta[1,2-d]pyrimidine; (3aS,6aS)-4-(Hexahydro-pyrrolo[3,4-b]pyrrol-1-yl)-6,7-dihydro-5H-benzo[6,7]cyclohepta[1,2-d]pyrimidin-2-ylamine; (1S,5S)-4-(3,6-Diaza-bicyclo[3.2.0]hept-3-yl)-6,7-dihydro-5H-benzo[6,7]cyclohepta[1,2-d]pyrimidin-2-ylamine; $N^4$-piperidin-3-yl-6,7-dihydro-5H-benzo[6,7]cyclohepta[1,2-d]pyrimidine-2,4-diamine; $N^4$-(octahydro-isoindol-4-yl)-6,7-dihydro-5H-benzo[6,7]cyclohepta[1,2-d]pyrimidine-2,4-diamine; methyl-(4-piperazin-1-yl-6,7-dihydro-5H-benzo[6,7]cyclohepta[1,2-d]pyrimidin-2-yl)-amine; 4-(3-(R)-methylamino-pyrrolidin-1-yl)-6,7-dihydro-5H-benzo[6,7]cyclohepta[1,2-d]pyrimidine; [1-(6,7-dihydro-5H-benzo[6,7]cyclohepta[1,2-d]pyrimidin-4-yl)-azetidin-3-yl]-amine; 8,10-dimethyl-4-piperazin-1-yl-6,7-dihydro-5H-benzo[6,7]

cyclohepta[1,2-d]pyrimidin-2-ylamine; 6-(2-(1H-imidazol-4-yl)ethylamino-6,7-dihydro-5H-benzo[6,7]cyclohepta[1,2-d]pyrimidin-4-yl)octahydro-1H-pyrrolo[3,4-b]pyridine; (2-amino-4-piperazin-1-yl-6,7-dihydro-5H-benzo[6,7]cyclohepta[1,2-d]pyrimidin-10-yl)-methyl-carbamic acid methyl ester; 10-N-methyl-4-piperazin-1-yl-6,7-dihydro-5H-benzo[6,7]cyclohepta[1,2-d]pyrimidine-2,10-diamine; (2-amino-4-octahydro-pyrrolo[3,4-b]pyridin-6-yl-6,7-dihydro-5H-benzo[6,7]cyclohepta[1,2-d]pyrimidin-10-yl)-methyl-carbamic acid methyl ester; 10-N-methyl-4-[(4aR,7aR)-octahydro-6H-pyrrolo[3,4-b]pyridin-6-yl]-6,7-dihydro-5H-benzo[6,7]cyclohepta[1,2-d]pyrimidine-2,10-diamine; N-(2-amino-4-piperazin-1-yl-6,7-dihydro-5H-benzo[6,7]cyclohepta[1,2-d]pyrimidin-11-yl)-acetamide; 4-(octahydro-pyrrolo[3,4-b]pyridin-6-yl)-6,7-dihydro-5H-benzo[6,7]cyclohepta[1,2-d]pyrimidine-2-carboxylic acid methyl ester; 4-(octahydro-pyrrolo[3,4-b]pyridin-6-yl)-6,7-dihydro-5H-benzo[6,7]cyclohepta[1,2-d]pyrimidine-2-carboxylic acid.

Particularly preferred examples of compounds of formula (VI) include, but are not limited to 4-((R)-3-amino-pyrrolidin-1-yl)-6,7-dihydro-5H-benzo[6,7]cyclohepta[1,2-d]pyrimidin-2-ylamine; 4-piperazin-1-yl-6,7-dihydro-5H-benzo[6,7]cyclohepta[1,2-d]pyrimidin-2-ylamine; and 4-(3-methylamino-azetidin-1-yl)-6,7-dihydro-5H-benzo[6,7]cyclohepta[1,2-d]pyrimidin-2-ylamine.

Compounds of formula (VII) are histamine $H_4$ receptor ligands and are described in EP1767537A1, filed Sep. 21, 2005, to Dyke, et al., and in WO20071090852, filed Feb. 7, 2007, to Reid, et al., and in WO2007/090853, filed Aug. 16, 2007, to Reid, et al., and in WO2007/090854, filed Aug. 16, 2007, to Reid, et al., which publications are herein incorporated by reference.

Compounds of formula:

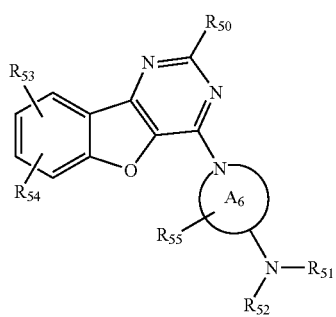

(VII)

or a pharmaceutically acceptable salt, ester, prodrug, or metabolite thereof, wherein:

$A_6$ represents heterocyclyl, preferably azetidinyl or pyrrolidinyl, having at least one nitrogen ring atom, which nitrogen is attached to the pyrimidine ring in formula (VII) and wherein $A_6$ is substituted with —$NR_{51}R_{52}$, $R_{55}$ and is optionally substituted with one or more other substituents independently selected from the group consisting of $C_{1-4}$ alkyl; F, Cl, Br, $C_{3-6}$ cycloalkyl, OH, and $OC_{1-4}$ alkyl, wherein each $C_{1-4}$ alkyl, $C_{3-6}$ cycloalkyl is optionally substituted with one or more halogen; $R_{50}$ represents H, $C_{1-4}$ alkyl, $C_{3-6}$ cycloalkyl, wherein each $C_{1-4}$ alkyl, $C_{3-6}$ cycloalkyl, is optionally substituted with one or more halogen or $R_{50}$ represents —$NR_{56}R_{57}$ wherein $R_{56}$ and $R_{57}$ are independently H, —$C(O)CH_3$, —$SO_2CH_3$, $C_{1-4}$ alkyl, $C_{3-6}$ cycloalkyl, wherein each $C_{1-4}$ alkyl, $C_{3-6}$ cycloalkyl is optionally substituted with one or more halogen;

$R_{51}$ and $R_{52}$ are independently H, $C_{1-4}$ alkyl or $C_{3-6}$ cycloalkyl; wherein each $C_{1-4}$ alkyl is optionally substituted with one or more substituents selected from the group consisting of halogen and $C_{3-6}$ cycloalkyl and wherein each $C_{3-6}$ cycloalkyl is optionally substituted with one or more halogen; Optionally $R_{51}$, $R_{52}$ jointly form together with the nitrogen to which they are attached to a heterocyclyl ring;

$R_{53}$ and $R_{54}$ are independently H, F, Cl, Br, CN, $C_{1-4}$ alkyl, OH, $OC_{1-4}$ alkyl, $C(O)OH$, $C(O)OC_{1-4}$ alkyl, $C(O)NH_2$, $C(O)NHC_{1-4}$ alkyl, $C(O)N(C_{1-4}$ alkyl$)_2$ wherein each $C_{1-4}$ alkyl is optionally substituted with one or more halogen. $R_{55}$ is selected from the group consisting of H, $C_{1-4}$ alkyl; F, Cl, Br, $C_{3-6}$ cycloalkyl, OH, and $OC_{1-4}$ alkyl, wherein each $C_{1-4}$ alkyl, $C_{3-6}$ cycloalkyl is optionally substituted with one or more halogen; or optionally $R_{55}$ form together with $R_{52}$ (—$R_{55}$-$R_{52}$-) a —$C_{1-4}$ alkyl-group.

Examples of compounds of formula (VII) include, but are not limited to N—[(R,S)-1-(8-chloro-2-methylbenzo[4,5]furo[3,2-d]-pyrimidin-4-yl)-pyrrolidin-3-yl]N-methylamine; N—[(R,S)-1-(8-chlorobenzo[4,5]furo[3,2-d]-pyrimidin-4-yl)-pyrrolidin-3-yl]N-methylamine; [(R,S)-1-(8-chloro-2-methylbenzo[4,5]furo[3,2-d]pyrimidin-4-yl) pyrrolidin-3-yl]-dimethylamine; N-[(R)-1-(8-chlorobenzo[4,5]furo[3,2-d]pyrimidin-4-yl)pyrrolidin-3-yl]N-methylamine; N-[(S)-1-(8-chlorobenzo[4,5]furo[3,2-d]pyrimidin-4-yl)pyrrolidin-3-yl)N-methylamine; N-[1-(8-chlorobenzo[4,5]furo[3,2-d]pyrimidin-4-yl)azetidin-3-yl] amine; N-[1-(8-chlorobenzo[4,5]furo[3,2-d]pyrimidin-4-yl) azetidin-3-yl]N-methylamine; N-[1-(8-chlorobenzo[4,5]furo[3,2-d]pyrimidin-4-yl)azetidin-3-yl]N,N-dimethylamine; [(R)-1-(2-amino-8-chlorobenzo[4,5]furo[3,2-d]-pyrimidin-4-yl)pyrrolidin-3-yl]N-methylamine; [(S)-1-(2-amino-8-chlorobenzo[4,5]furo[3,2-d]-pyrimidin-4-yl) pyrrolidin-3-yl]N-methylamine; [1-(2-ethylamino-8-chlorobenzo[4,5]furo[3,2-d]-pyrimidin-4-yl)azetidin-3-yl] N-ethylamine; 4-((R)-3-methylamino-pyrrolidin-1-yl)-benzo[4,5]furo[3,2-d]pyrimidin-2-ylamine; 8-methyl-4-((R)-3-methylamino-pyrrolidin-1-yl)-benzo[4,5]furo[3,2-d] pyrimidin-2-ylamine; 8-fluoro-4-((R)-3-methylamino-pyrrolidin-1-yl)-benzo[4,5]furo[3,2-d]pyrimidin-2-ylamine; 8-bromo-4-((R)-3-methylamino-pyrrolidin-1-yl)-benzo[4,5] furo[3,2-d]pyrimidin-2-ylamine; 7-chloro-4-((R)-3-methylamino-pyrrolidin-1-yl)-benzo[4,5]furo[3,2-d]pyrimidin-2-ylamine; N-[1-(2-amino-8-chlorobenzo[4,5]furo[3,2-d] pyrimidin-4-yl)azetidin-3-yl]N-methylamine; 4-(3-methylamino-azetidin-1-yl)-benzo[4,5]furo[3,2-d] pyrimidin-2-ylamine; 8-bromo-4-(3-methylamino-azetidin-1-yl)-benzo[4,5]furo[3,2-d]pyrimidin-2-ylamine; 8-methyl-4-(3-methylamino-azetidin-1-yl)-benzo[4,5]furo[3,2-d] pyrimidin-2-ylamine; 8-fluoro-4-(3-methylamino-azetidin-1-yl)-benzo[4,5]furo[3,2-d]pyrimidin-2-ylamine; 8-methoxy-4-((R)-3-methylamino-pyrrolidin-1-yl)-benzo[4,5]furo[3,2-d]pyrimidin-2-ylamine; 4-((R)-3-methylamino-pyrrolidin-1-yl)-8-trifluoromethoxy-benzo[4,5]furo[3,2-d]pyrimidin-2-ylamine; 9-fluoro-4-((R)-3-methylamino-pyrrolidin-1-yl)-benzo[4,5]furo[3,2-d] pyrimidin-2-ylamine; 9-methyl-4-((R)-3-methylaminopyrrolidin-1-yl)-benzo[4,5]furo[3,2-d]pyrimidin-2-ylamine; 9-methoxy-4-((R)-3-methylamino-pyrrolidin-1-yl)-benzo[4,5]furo[3,2-d]pyrimidin-2-ylamine; 7-methyl-4-((R)-3-methylamino-pyrrolidin-1-yl)-benzo[4,5]furo[3,2-d]pyrimidin-2-ylamine; 7-methoxy-4-((R)-3-methylamino-pyrrolidin-1-yl)-benzo[4,5]furo[3,2-d]pyrimidin-2-ylamine; 4-((R)-3-methylamino-pyrrolidin-1-yl)-7-trifluoromethyl-benzo[4,5]furo[3,2-d]pyrimidin-2-ylamine; 7-methoxy-4-((R)-3-methylamino-pyrrolidin-1-yl)-benzo[4,5]furo[3,2-d]pyrimidin-2-ylamine; 6-chloro-4-((R)-3-methylamino-pyrrolidin-1-yl)-benzo[4,5]furo[3,2-d]pyrimidin-2-ylamine; 6-methyl-4-((R)-3-methylamino-pyrrolidin-1-yl)-benzo[4,5]furo[3,2-d]pyrimidin-2-ylamine; 6-methoxy-4-((R)-3-methylamino-pyrrolidin-1-yl)-benzo[4,5]furo[3,2-d]pyrimidin-2-ylamine; 8-methoxy-4-(3-methylamino-azetidin-1-yl)-benzo[4,5]furo[3,2-d]pyrimidin-2-ylamine; 4-(3-methylamino-azetidin-1-yl)-8-trifluoromethoxy-benzo[4,5]furo[3,2-d]pyrimidin-2-ylamine; 9-fluoro-4-(3-methylamino-azetidin-1-yl)-benzo[4,5]furo[3,2-d]pyrimidin-2-ylamine; 9-methyl-4-(3-methylamino-azetidin-1-yl)-benzo[4,5]furo[3,2-d]pyrimidin-2-ylamine; 9-methoxy-4-(3-methylamino-azetidin-1-yl)-benzo[4,5]furo[3,2-d]pyrimidin-2-ylamine; 7-methyl-4-(3-methylamino-azetidin-1-yl)-benzo[4,5]furo[3,2-d]pyrimidin-2-ylamine; 7-methoxy-4-(3-methylamino-azetidin-1-yl)-benzo[4,5]furo[3,2-d]pyrimidin-2-ylamine; 4-(3-methylamino-azetidin-1-yl)-7-trifluoromethyl-benzo[4,5]furo[3,2-d]pyrimidin-2-ylamine; 6-chloro-4-(3-methylamino-azetidin-1-yl)-benzo[4,5]furo[3,2-d]pyrimidin-2-ylamine; 6-methyl-4-(3-methylamino-azetidin-1-yl)-benzo[4,5]furo[3,2-d]pyrimidin-2-ylamine; 6-methoxy-4-(3-methylamino-azetidin-1-yl)-benzo[4,5]furo[3,2-d]pyrimidin-2-ylamine; 8-chloro-4-[3-(cyclopropylmethyl-amino)-pyrrolidin-1-yl]-benzo[4,5]furo[3,2-d]pyrimidin-2-ylamine; 8-chloro-4-((R)-3-dimethylamino-pyrrolidin-1-yl)-benzo[4,5]furo[3,2-d]pyrimidin-2-ylamine; 4-((R)-3-amino-pyrrolidin-1-yl)-8-chloro-benzo[4,5]furo[3,2-d]pyrimidin-2-ylamine; 8-chloro-4-(4-methylamino-piperidin-1-yl)-benzo[4,5]furo[3,2-d]pyrimidin-2-ylamine; 4-(4-amino-piperidin-1-yl)-8-chloro-benzo[4,5]furo[3,2-d]pyrimidin-2-ylamine; 4-(3-amino-azetidin-1-yl)-8-chloro-benzo[4,5]furo[3,2-d]pyrimidin-2-ylamine; [8-chloro-4-((R)-3-methylamino-pyrrolidin-1-yl)-benzo[4,5]furo[3,2-d]pyrimidin-2-yl]-methyl-amine; [8-chloro-4-((R)-3-methylamino-pyrrolidin-1-yl)-benzo[4,5]furo[3,2-d]pyrimidin-2-yl]-dimethyl-amine; N-[8-chloro-4-((R)-3-methylamino-pyrrolidin-1-yl)-benzo[4,5]furo[3,2-d]pyrimidin-2-yl]-acetamide; N-[8-chloro-4-((R)-3-methylamino-pyrrolidin-1-yl)-benzo[4,5]furo[3,2-d]pyrimidin-2-yl]-methanesulfonamide; [8-chloro-4-((R)-3-methylamino-pyrrolidin-1-yl)-benzo[4,5]furo[3,2-d]pyrimidin-2-yl]-cyclopropyl-amine; [8-chloro-4-((R)-3-methylamino-pyrrolidin-1-yl)-benzo[4,5]furo[3,2-d]pyrimidin-2-yl]-methyl-amine; [8-chloro-4-((R)-3-methylamino-pyrrolidin-1-yl)-benzo[4,5]furo[3,2-d]pyrimidin-2-yl]-dimethyl-amine; N-[8-chloro-4-(3-methylamino-azetidin-1-yl)-benzo[4,5]furo[3,2-d]pyrimidin-2-yl]-acetamide; N-[8-chloro-4-(3-methylamino-azetidin-1-yl)-benzo[4,5]furo[3,2-d]pyrimidin-2-yl]-methanesulfonamide; [8-chloro-4-(3-methylamino-azetidin-1-yl)-benzo[4,5]furo[3,2-d]pyrimidin-2-yl]-cyclopropyl-amine; [(R)-1-(2-amino-8-chlorobenzo[4,5]furo[3,2-d]pyrimidin-4-yl)pyrrolidin-3-yl]N-methylamine; 4-((R)-3-methylamino-pyrrolidin-1-yl)-benzo[4,5]furo[3,2-d]pyrimidin-2-ylamine; 8-methyl-4-((R)-3-methylamino-pyrrolidin-1-yl)-benzo[4,5]furo[3,2-d]pyrimidin-2-ylamine; 8-fluoro-4-((R)-3-methylamino-pyrrolidin-1-yl)-benzo[4,5]furo[3,2-d]pyrimidin-2-ylamine; 8-bromo-4-((R)-3-methylamino-pyrrolidin-1-yl)-benzo[4,5]furo[3,2-d]pyrimidin-2-ylamine; 7-chloro-4-((R)-3-methylamino-pyrrolidin-1-yl)-benzo[4,5]furo[3,2-d]pyrimidin-2-ylamine; 8-methoxy-4-((R)-3-methylamino-pyrrolidin-1-yl)-benzo[4,5]furo[3,2-d]pyrimidin-2-ylamine; 8-chloro-4-[3-(cyclopropylmethyl-amino)-pyrrolidin-1-yl]-benzo[4,5]furo[3,2-d]pyrimidin-2-ylamine; 8-chloro-4-((R)-3-dimethylamino-pyrrolidin-1-yl)-benzo[4,5]furo[3,2-d]pyrimidin-2-ylamine; 4-((R)-3-amino-pyrrolidin-1-yl)-8-chloro-benzo[4,5]furo[3,2-d]pyrimidin-2-ylamine; N-[1-(2-ethylamino-8-chlorobenzo[4,5]furo[3,2-d]-pyrimidin-4-yl)azetidin-3-yl]N-methylamine; 4-(3-methylamino-azetidin-1-yl)-8-chloro-benzo[4,5]furo[3,2-d]pyrimidin-2-ylamine; [8-chloro-4-(3-methylamino-azetidin-1-yl)-benzo[4,5]furo[3,2-d]pyrimidin-2-yl]methylamine; and [8-chloro-4-(3-methylamino-azetidin-1-yl)-benzo[4,5]furo[3,2-d]pyrimidin-2-yl]dimethylamine.

Compounds of formulae (VIII) and (IX) are histamine $H_4$ receptor ligands and are described in US2005/0070550A1, filed Sep. 29, 2004, to Arienti, et al., which publication is herein incorporated by reference.

Compounds of formulae

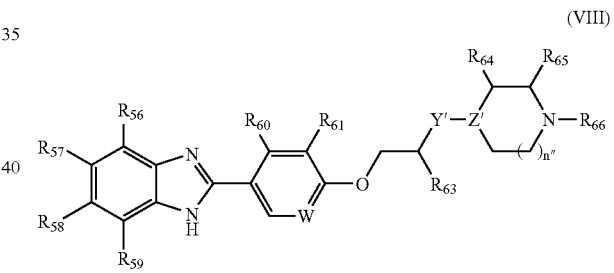

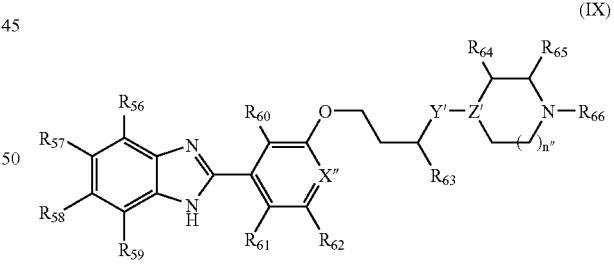

wherein:
W is N or $CR_{62}$;
X" is N or CH;
Y' is O, $NR_{67}$, or $CR_{67}R_{68}$;
Z' is N or $CR_{69}$;
n" is 0, 1, or 2;
each of $R_{69}$ is, independently from other substituent assignments, H, $C_{1-4}$alkyl, $C_{2-5}$alkenyl, $C_{2-5}$alkynyl, $C_{3-6}$cycloalkyl, —$C_{1-4}$alkoxy, —$C_{1-4}$alkylamino, —$C_{1-4}$alkylthio, —$C_{1-4}$alkylsulfonyl, —$OC_{3-6}$cycloalkyl, —$OCH_2Ph$, cyano, —$CF_3$, F, Cl, Br, I, nitro, —$OCF_3$, $SCF_3$, —$OR^c$, —$SR^c$, S(O)R$^c$, —SO$_2$R$^c$, —C(O)R$^c$, phenyl, benzyl, phenethyl, C(O)NR$^a$R$^b$, —C(O)OR$^c$, —NR$^a$R$^b$, —CH$_2$NR$^a$R$^b$ or —CH$_2$OR$^c$; wherein each of R$^a$, R$^b$ and R$^c$ is, independently from other substituent assignments, selected from H, C$_{1-4}$alkyl, C$_{3-6}$cycloalkyl, phenyl, (C$_{3-6}$cycloalkyl)C$_{1-2}$alkyl-, benzyl and phenethyl, or R$^a$ and R$^b$ taken together with the nitrogen to which they are attached, form a 4-7 membered heterocyclic ring HetCyc1, wherein said ring HetCyc1 has 0 or 1 additional heteroatoms selected from O, S, >NH and >NC$_{1-6}$alkyl, and wherein any phenyl, phenethyl, benzyl, alkyl or cycloalkyl moiety in any of said R$_{69}$, R$^a$, R$^b$, R$^c$, and said ring HetCyc1 is optionally, and independently from other substituent assignments, substituted with 1, 2 or 3 substituents selected from C$_{1-3}$alkyl, halo, hydroxy, amino, and C$_{1-3}$alkoxy;

each of R$_{60-62}$ is, independently from other substituent assignments, H, C$_{1-4}$alkyl, F, Cl, Br, I, CF$_3$, —OCF$_3$, —OR$^c$, SR$^c$, S(O)R$^c$, —SO$_2$R$^c$, C$_{1-4}$alkoxy, cyano, nitro, —C(O)NR$^a$R$^b$, —C(O)phenyl, —C(O)C$_{1-6}$alkyl, S(O)C$_{1-4}$alkyl, or SO$_2$C$_{1-4}$alkyl; or, R$_{60}$ and R$_{61}$ for a compound of formula (VIII) taken together with the carbon atoms to which they are attached form a cyclic structure Cyc1 selected from aryl, heteroaryl, 5- or 6-membered carbocycle, and 5- or 6-membered heterocycle with 1 or 2 heteroatoms, wherein said cyclic structure Cyc1 is, independently from other substituent assignments, substituted with 0, 1, or 2 substituents selected from C$_{1-3}$alkyl, halo, hydroxy, amino, and C$_{1-3}$alkoxy; or, R$_{61}$ and R$_{62}$ for a compound of formula (IX) taken together with the carbon atoms to which they are attached form a cyclic structure Cyc2 selected from aryl, heteroaryl, 5- or 6-membered carbocycle, and 5- or 6-membered heterocycle with 1 or 2 heteroatoms. wherein said cyclic structure Cyc2 is, independently from other substituent assignments, substituted with 0, 1, or 2 substituents selected from C$_{1-3}$alkyl, halo, hydroxy, amino, and C$_{1-3}$alkoxy;

R$_{63}$ is H, C$_{1-6}$alkyl, C$_{1-4}$alkoxy, or OH;

each of R$_{64}$ and R$_{65}$ is, independently from other substituent assignments, H or C$_{1-6}$alkyl, or R$_{64}$ and R$_{65}$ taken together form a 5-6 membered cyclic structure Cyc3, wherein said cyclic structure Cyc3 is a 5- or 6-membered carbocycle or a 5- or 6-membered heterocycle with 1 or 2 heteroatoms, and wherein said cyclic structure Cyc3 is, independently from other substituent assignments, substituted with 0, 1, or 2 substituents selected from C$_{1-3}$alkyl, halo, hydroxy, amino, and C$_{1-3}$alkoxy;

R$_{66}$ is H, C$_{1-4}$alkyl;

each of R$_{67}$ and R$_{68}$ is, independently from other substituent assignments, H or C$_{1-4}$alkyl; or, when Y' is CR$_{67}$R$_{68}$, R$_{67}$ and R$_{68}$ taken together with the carbon member to which they are attached form an optionally substituted cyclic structure Cyc4, wherein said cyclic structure Cyc4 is a 3- to 6-membered carbocycle or a 3- to 6-membered heterocycle with 0 or 1 additional heteroatoms, or CR$_{67}$R$_{68}$ is C=O;

R$_{69}$ is H, C$_{1-4}$alkyl, OH, or C$_{1-4}$alkoxy;

an enantiomer, diastereomer, racemate thereof, or a pharmaceutically acceptable salt, amide or ester thereof;

provided that:

when Y' is O or NR$_{67}$, then Z' is CR$_{69}$ and R$_{63}$ is not OH or C$_{1-4}$alkoxy;

when Z' is N, Y' is CR$_{67}$R$_{68}$ and neither R$_{56}$ nor R$_{59}$ is C(O)NH$_2$.

Examples of compounds of formulae (XIII) and (IX) include, but are not limited to 2-{2-chloro-4-[3-(4-methyl-piperazin-1-yl)-propoxy]-phenyl)-4,5-dimethyl-1H-benzoimidazole; 2-{2-chloro-4-[3-(1-methyl-piperidin-4-yl)-propoxy]-phenyl)-4-methyl-1H-benzoimidazole; 2-{2-chloro-4-[3-(4-methyl-piperazin-1-yl)-propoxy]-phenyl)-5-trifluoromethoxy-1H-benzoimidazole; 5-tert-butyl-2-{3-chloro-4-[3-(4-methyl-[1,4]diazepan-1-yl)-propoxy]-phenyl}-1H-benzoimidazole; 5-tert-butyl-2-{3-chloro-4-[3-(4-methyl-piperazin-1-yl)-propoxy]-phenyl}-1H-benzoimidazole; 4,5-dimethyl-2-{3-methyl-4-[3-(4-methyl-piperazin-1-yl)-propoxy]-phenyl}-1H-benzoimidazole; 5-tert-butyl-2-{3-[4-(4-methyl-piperazin-1-yl)-butoxy]-phenyl}-1H-benzoimidazole; 5-tert-butyl-2-{3-[4-(4-methyl-[1,4]diazepan-1-yl)-butoxy]-phenyl}-1H-benzoimidazole; (1-{3-[4-(5-tert-butyl-1H-benzoimidazol-2-yl)-2-chlorophenoxy]-propyl}-pyrrolidin-3-yl)-dimethylamine; 5-chloro-2-{3-chloro-4-[3-(4-methyl-[1,4]diazepan-1-yl)-propoxy]-phenyl}-6-methyl-1H-benzoimidazole; 2-{3-fluoro-4-[3-(4-methyl-piperazin-1-yl)-propoxy]-phenyl}-4-methyl-1H-benzoimidazole; 5-methyl-2-{4-[3-(4-methyl-piperazin-1-yl)-propoxy]-naphthalen-1-yl}-1H-benzoimidazole; 4-[3-(5-tert-butyl-1H-benzoimidazol-2-yl)-phenoxy]-1-(4-methyl-piperazin-1-yl)-butan-1-one; 5-chloro-2-[3-chloro-4-(3-piperazin-1-yl-propoxy)-phenyl]-6-fluoro-1H-benzoimidazole; 5-tert-butyl-2-{3-methyl-4-[3-(4-methyl-piperazin-1-yl)-propoxy]-phenyl}-1H-benzoimidazole; 2-{2-chloro-4-[3-(1-methyl-piperidin-4-yl)-propoxy]-phenyl}-4,6-dimethyl-1H-benzoimidazole; 2-{2-chloro-4-[2-methyl-3-(4-methyl-piperazin-1-yl)-propoxy]-phenyl}-4-methyl-1H-benzoimidazole; 5-chloro-2-{3-chloro-4-[3-(4-methyl-piperazin-1-yl)-propoxy]-phenyl}-6-methyl-1H-benzoimidazole; 6-chloro-2-{2-chloro-4-[3-(4-methyl-piperazin-1-yl)-propoxy]-phenyl}-4-methyl-1H-benzoimidazole; 5-tert-butyl-2-{3-chloro-4-[3-(4-methyl-piperazin-1-yl)-propoxy]-phenyl}-1H-benzoimidazole; 5-chloro-2-{3-fluoro-4-[3-(4-methyl-piperazin-1-yl)-propoxy]-phenyl)-1H-benzoimidazole; 2-{2-chloro-4-[3-(4-methyl-[1,4]diazepan-1-yl)-propoxy]-phenyl}-4,6-dimethyl-1H-benzoimidazole; 5-chloro-6-methyl-2-{3-[4-(4-methyl-piperazin-1-yl)-butoxy]-phenyl}-1H-benzoimidazole; 5-chloro-6-fluoro-2-{3-fluoro-4-[3-(4-methyl-piperazin-1-yl)-propoxy]-phenyl}-1H-benzoimidazole; 2-{3-fluoro-4-[3-(4-methyl-piperazin-1-yl)-propoxy]-phenyl}-5-methyl-1H-benzoimidazole; 5,6-difluoro-2-{3-fluoro-4-[3-(4-methyl-piperazin-1-yl)-propoxy]-phenyl}-1H-benzoimidazole; 2-{3-fluoro-4-[3-(4-methyl-piperazin-1-yl)-propoxy]-phenyl}-1H-benzoimidazole; 2-{2-chloro-4-[3-(4-methyl-[1,4]diazepan-1-yl)-propoxy]-phenyl}-4,5-dimethyl-1H-benzoimidazole; 5,6-dimethyl-2-{3-[4-(4-methyl-piperazin-1-yl)-butoxy]-phenyl}-1H-benzoimidazole; 2-{2-chloro-4-[3-(4-methyl-piperazin-1-yl)-propoxy]-phenyl}-4,6-dimethyl-1H-benzoimidazole; 2-{2-chloro-4-[3-(4-methyl-[1,4]diazepan-1-yl)-propoxy]-phenyl}-4-methyl-1H-benzoimidazole; 5-tert-butyl-2-{2-chloro-4-[3-(4-methyl-piperazin-1-yl)-propoxy]-phenyl}-1H-benzoimidazole; 2-{3-methoxy-4-[3-(4-methyl-piperazin-1-yl)-propoxy]-phenyl}-5-trifluoromethyl-1H-benzoimidazole; 5-chloro-2-{3-chloro-4-[3-(4-methyl-piperazin-1-yl)-propoxy]-phenyl}-6-fluoro-1H-benzoimidazole; 5,6-dichloro-2-{2-chloro-4-[3-(4- methyl-piperazin-1-yl)-propoxy]-phenyl}-1H-benzoimidazole; 5-chloro-2-{2-chloro-4-[3-(4-methyl-piperazin-1-yl)-propoxy]-phenyl}-1H-benzoimidazole; 5-chloro-2-{2-chloro-4-[3-(4-methyl-piperazin-1-yl)-propoxy]-phenyl}-6-fluoro-1H-benzoimidazole; 5-chloro-2-{3-methyl-4-[3-(4-methyl-piperazin-1-yl)-propoxy]-phenyl}-1H-benzoimidazole; 2-{3-chloro-4-[3-(4-methyl-piperazin-1-yl)-propoxy]-phenyl}-5-methyl-1H-benzoimidazole; 5,6-dichloro-2-{3-chloro-4-[3-(4-methyl-piperazin-1-yl)-propoxy]-phenyl}-1H-benzoimidazole; 5-chloro-6-methyl-2-{3-methyl-4-[3-(4-methyl-piperazin-1-yl)-propoxy]-phenyl}-1H-benzoimidazole; 2-{2-chloro-4-[3-(4-methyl-piperazin-1-yl)-propoxy]-phenyl}-5-methyl-1H-benzoimidazole; 5-chloro-2-{3-chloro-4-[3-(4-methyl-piperazin-1-yl)-propoxy]-phenyl}-1H-benzoimidazole; 2-{3-chloro-4-[3-(4-methyl-piperazin-1-yl)-propoxy]-phenyl}-5-trifluoromethyl-1H-benzoimidazole; 5-chloro-6-fluoro-2-{3-methyl-4-[3-(4-methyl-piperazin-1-yl)-propoxy]-phenyl}-1H-benzoimidazole; 5-methyl-2-{3-methyl-4-[3-(4-methyl-piperazin-1-yl)-propoxy]-phenyl}-1H-benzoimidazole; 2-{3-chloro-4-[3-(4-methyl-piperazin-1-yl)-propoxy]-phenyl}-1H-benzoimidazole; 2-{3-methyl-4-[3-(4-methyl-piperazin-1-yl)-propoxy]-phenyl}-1H-benzoimidazole; 2-{2-chloro-4-[3-(4-methyl-piperazin-1-yl)-propoxy]-phenyl}-1H-benzoimidazole; 5-chloro-6-fluoro-2-{3-methoxy-4-[3-(4-methyl-piperazin-1-yl)-propoxy]-phenyl}-1H-benzoimidazole; 2-{3-chloro-4-[3-(4-methyl-piperazin-1-yl)-propoxy]-phenyl}-5-methoxy-1H-benzoimidazole; 5-tert-butyl-2-{3,5-dibromo-4-[3-(methyl-piperazin-1-yl)-propoxy]-phenyl}-1H-benzoimidazole; 2-{2-methoxy-4-[3-(4-methyl-piperazin-1-yl)-propoxy]-phenyl}-1H-benzoimidazole; 2-{2-chloro-4-[3-(4-methyl-piperazin-1-yl)-propoxy]-phenyl}-5-trifluoromethyl-1H-benzoimidazole; 2-{3-[3-(4-methyl-piperazin-1-yl)-propoxy]-phenyl}-1H-benzoimidazole; (2-{3-[4-(4-methyl-piperazin-1-yl)-butoxy]-phenyl}-1H-benzoimidazol-5-yl)-phenyl-methanone; 6-chloro-2-{2-chloro-4-[3-(1-methyl-piperidin-4-yl)-propoxy]-phenyl}-4-methyl-1H-benzoimidazole; 5-tert-butyl-2-{3-chloro-4-[3-(1-methyl-piperidin-4-yl)-propoxy]-phenyl}-1H-benzoimidazole; 2-{2-chloro-4-[3-(1-methyl-piperidin-4-yl)-propoxy]-phenyl}-4,5-dimethyl-1H-benzoimidazole; 5-chloro-6-methyl-2-{4-[3-(1-methyl-piperidin-4-yl)-propoxy]-phenyl}-1H-benzoimidazole; 5-chloro-2-{4-[3-(1-methyl-piperidin-4-yl)-propoxy]-phenyl}-1H-benzoimidazole; 5-chloro-6-fluoro-{4-[3-(1-methyl-piperidin-4-yl)-propoxy]-phenyl}-1H-benzoimidazole; 5-tert-butyl-2-{4-[3-(1-methyl-piperidin-4-yl)-propoxy]-phenyl}-1H-benzoimidazole; 5-methyl-2-{4-[3-(1-methyl-piperidin-4-yl)-propoxy]-phenyl}-1H-benzoimidazole; 2-{4-[3-(1-methyl-piperidin-4-yl)-propoxy]-phenyl}-1H-benzoimidazole; 6-chloro-2-{2-fluoro-4-[3-(1-methyl-piperidin-4-yl)-propoxy]-phenyl}-1H-benzoimidazole; 5-fluoro-2-{2-methyl-4-[3-(1-methyl-piperidin-4-yl)-propoxy]-phenyl}-1H-benzoimidazole; 4-chloro-2-{2-methyl-4-[3-(1-methyl-piperidin-4-yl)-propoxy]-phenyl}-1H-benzoimidazole; 6-chloro-4-methyl-{2-methyl-4-[3-(1-methyl-piperidin-4-yl)-propoxy]-phenyl}-1H-benzoimidazole; 5-chloro-2-{2-chloro-4-[3-(1-methyl-piperidin-4-yl)-propoxy]-phenyl}-6-fluoro-1H-benzoimidazole; 2-{2-chloro-4-[3-(1-methyl-piperidin-4-yl)-propoxy]-phenyl}-3H-naphtho[1.2-d]imidazole; 4,6-dimethyl-2-{2-methyl-4-[3-(4-methyl-piperazin-1-yl)-propoxy]-phenyl}-1H-benzoimidazole; 2-{2-chloro-4-[3-(4-methyl-piperazin-1-yl)-propoxy]-phenyl}-4-methyl-1H-benzoimidazole; 2-{2-chloro-4-[3-(4-methyl-piperazin-1-yl)-propoxy]-phenyl}-5-fluoro-4-methyl-1H-benzoimidazole; 2-{2-chloro-4-[3-(4-methyl-piperazin-1-yl)-propoxy]-phenyl}-3H-naphtho[1,2-d]imidazole; 6-{2-chloro-4-[3-(4-methyl-piperazin-1-yl)-propoxy]-phenyl}-5H-[1,3]dioxolo[4',5':4,5]benzo[1,2-d]imidazole; 6-chloro-2-{2-chloro-4-[3-(4-methyl-[1,4]diazepan-1-yl)-propoxy]-phenyl}-4-methyl-1H-benzoimidazole; 2-{3-chloro-4-[3-(4-methyl-[1,4]diazepan-1-yl)-propoxy]-phenyl}-4-methyl-1H-benzoimidazole; 4,6-dimethyl-2-{3-[4-(4-methyl-[1,4]diazepan-1-yl)-butoxy]-phenyl}-1H-benzoimidazole; 5-chloro-2-{4-[3-(4-methyl-piperazin-1-yl)-propoxy]-phenyl}-1H-benzoimidazole; 2-{4-[3-(4-methyl-piperazin-1-yl)-propoxy]-phenyl}-1H-benzoimidazole; {2-(6-chloro-4-methyl-1H-benzoimidazol-2-yl)-5-[3-(1-methyl-piperidin-4-yl)-propoxy]-benzyl}-dimethylamine; {2-(5-fluoro-4-methyl-1H-benzoimidazol-2-yl)-5-[3-(1-methyl-piperidin-4-yl)-propoxy]-benzyl}-dimethylamine; 4-{3-[4-(6-chloro-4-methyl-1H-benzoimidazol-2-yl)-3-methyl-phenoxy]-propyl}-[1,4]diazepan-5-one; 4-{3-[4-(5-tert-butyl-1H-benzoimidazol-2-yl)-3-methyl-phenoxy]-propyl}-1-methyl-[1,4]diazepan-5-one; 5-tert-butyl-2-{2-methyl-4-[3-(2-methyl-piperazin-1-yl)-propoxy]-phenyl}-1H-benzoimidazole; 6-chloro-4-methyl-2-[2-methyl-4-(3-piperidin-4-yl-propoxy)-phenyl]-1H-benzoimidazole; 5-fluoro-4-methyl-2-[2-methyl-4-(3-piperidin-4-yl-propoxy)-phenyl]-1H-benzoimidazole; 6-chloro-2-{4-[3-(1-ethyl-piperidin-4-yl)-propoxy]-2-methyl-phenyl}-4-methyl-1H-benzoimidazole; {2-[3-chloro-4-(4-methyl-1H-benzoimidazol-2-yl)-phenoxy]-ethyl}-methyl-(1-methyl-piperidin-4-yl)-amine; 6-chloro-4-methyl-2-{2-methyl-4-[2-(1-methyl-piperidin-4-yloxy)-ethoxy]-phenyl}-1H-benzoimidazole; 6-chloro-4-methyl-2-{2-methyl-4-[3-(1-methyl-1,2,3,6-tetrahydro-pyridin-4-yl)-propoxy]-phenyl}-1H-benzoimidazole; 5-fluoro-4-methyl-2-{2-methyl-4-[3-(1-methyl-1,2,3,6-tetrahydro-pyridin-4-yl)-propoxy]-phenyl}-1H-benzoimidazole; 6-fluoro-7-methyl-2-{3-[4-(1-methyl-piperidin-4-yl)-butoxy]-phenyl}-1H-benzoimidazole; 7-methyl-2-{3-[4-(1-methyl-piperidin-4-yl)-butoxy]-phenyl}-1H-benzoimidazole; 6,7-dimethyl-2-{3-[4-(1-methyl-piperidin-4-yl)-butoxy]-phenyl}-1H-benzoimidazole; 5-chloro-7-methyl-2-{3-[4-(1-methyl-piperidin-4-yl)-butoxy]-phenyl}-1H-benzoimidazole; 5,7-dimethyl-2-{2-methyl-3-[4-(1-methyl-piperidin-4-yl)-butoxy]-phenyl}-1H-benzoimidazole; 5-chloro-7-methyl-2-{2-methyl-3-[4-(1-methyl-piperidin-4-yl)-butoxy]-phenyl}-1H-benzoimidazole; 6-fluoro-7-methyl-2-{2-methyl-3-[4-(1-methyl-piperidin-4-yl)-butoxy]-phenyl}-1H-benzoimidazole; 6-fluoro-7-methyl-2-{3-[3-(1-methyl-piperidin-4-yloxy)-propoxy]-phenyl}-1H-benzoimidazole; {2-(5-fluoro-4-methyl-1H-benzoimidazol-2-yl)-5-[3-(1-methyl-piperidin-4-yl)-propoxy]-phenyl}-methanol; 6-chloro-4-methyl-2-{6-[3-(4-methyl-piperazin-1-yl)-propoxy]-pyridin-3-yl}-1H-benzoimidazole; 4-methyl-2-{6-[3-(4-methyl-piperazin-1-yl)-propoxy-pyridin-3-yl}-1H-benzoimidazole; 5-fluoro-4-methyl-2-{6-[3-(4-methyl-piperazin-1-yl)-propoxy-pyridin-3-yl}-1H-benzoimidazole; 4-methyl-2-{6-[3-(3-(1-methyl-piperidin- 4-yl)-propoxy]-pyridin-3-yl}-1H-benzoimidazole; 4,5-dimethyl-2-{6-[3-(1-methyl-piperidin-4-yl)-propoxy]-pyridin-3-yl}-1H-benzoimidazole; 4-chloro-2-{6-[3-(1-methyl-piperidin-4-yl)-propoxy]-pyridin-3-yl}-1H-benzoimidazole; 6-chloro-4-methyl-2-{4-methyl-6-[3-(1-methyl-piperidin-4-yl)-propoxy]-pyridin-3-yl}-1H-benzoimidazole; 4-methyl-2-{4-methyl-6-[3-(1-methyl-piperidin-4-yl)-propoxy]-pyridin-3-yl}-1H-benzoimidazole; 5-fluoro-4-methyl-2-{4-methyl-6-[3-(1-methyl-piperidin-4-yl)-propoxy]-pyridin-3-yl}-1H-benzoimidazole; 4,5-dimethyl-2-{4-methyl-6-[3-(1-methyl-piperidin-4-yl)-propoxy]-pyridin-3-yl}-1H-benzoimidazole; 4,6-dimethyl-2-{4-methyl-6-[3-(1-methyl-piperidin-4-yl)-propoxy]-pyridin-3-yl}-1H-benzoimidazole; 4-chloro-2-{4-methyl-6-[3-(1-methyl-piperidin-4-yl)-propoxy]-pyridin-3-yl}-1H-benzoimidazole; 2-{4-chloro-6-[3-(1-methyl-piperidin-4-yl)-propoxy]-pyridin-3-yl}-5-fluoro-4-methyl-1H-benzoimidazole; 2-{4-chloro-6-[3-(1-methyl-piperidin-4-yl)-propoxy]-pyridin-3-yl}-4-methyl-1H-benzoimidazole; 6-chloro-2-{4-chloro-6-[3-(1-methyl-piperidin-4-yl)-propoxy]-pyridin-3-yl}-4-methyl-1H-benzoimidazole; 2-{4-chloro-6-[3-(1-methyl-piperidin-4-yl)-propoxy]-pyridin-3-yl}-4,6-dimethyl-1H-benzoimidazole; 2-{4-methoxy-6-[3-(1-methyl-piperidin-4-yl)-propoxy]-pyridin-3-yl}-4-methyl-1H-benzoimidazole; 5-fluoro-2-{4-methoxy-6-[3-(1-methyl-piperidin-4-yl)-propoxy]-pyridin-3-yl}-4-methyl-1H-benzoimidazole; 5-fluoro-4-methyl-2-{6-[3-(1-methyl-1,2,3,6-tetrahydro-pyridin-4-yl)-propoxy]-pyridin-3-yl}-1H-benzoimidazole; 4-methyl-2-{6-[3-(1-methyl-1,2,3,6-tetrahydro-pyridin-4-yl)-propoxy]-pyridin-3-yl}-1H-benzoimidazole; 6-chloro-4-methyl-2-{6-[3-(1-methyl-1,2,3,6-tetrahydro-pyridin-4-yl)-propoxy]-pyridin-3-yl}-1H-benzoimidazole; 4,5-dimethyl-2-{6-[3-(1-methyl-1,2,3,6-tetrahydro-pyridin-4-yl)-propoxy]-pyridin-3-yl}-1H-benzoimidazole; 4,6-dimethyl-2-{6-[3-(1-methyl-1,2,3,6-tetrahydro-pyridin-4-yl)-propoxy]-pyridin-3-yl}-1H-benzoimidazole; 5-chloro-4-methyl-2-{6-[3-(1-methyl-1,2,3,6-tetrahydropyridin-4-yl)-propoxy]-pyridin-3-yl}-1H-benzoimidazole; 5-fluoro-4-methyl-2-{6-[3-(1-methyl-piperidin-4-yl)-propoxy]-4-pyrrolidin-1-ylmethyl-pyridin-3-yl}-1H-benzoimidazole; 2-{5-bromo-2-[4-(1-methyl-piperidin-4-yl)-butoxy]-pyridin-4-yl}-4-methyl-1H-benzoimidazole; 2-{5-bromo-2-[4-(1-methyl-piperidin-4-yl)-butoxy]-pyridin-4-yl}-5-fluoro-4-methyl-1H-benzoimidazole; 2-{5-bromo-2-[4-(1-methyl-piperidin-4-yl)-butoxy]-pyridin-4-yl}-6-chloro-4-methyl-1H-benzoimidazole; 2-{5-bromo-2-[4-(1-methyl-piperidin-4-yl)-butoxy]-pyridin-4-yl}-4,6-dimethyl-1H-benzoimidazole; 2-{5-bromo-2-[4-(1-methyl-piperidin-4-yl)-butoxy]-pyridin-4-yl}-4,5-dimethyl-1H-benzoimidazole; 2-{5-bromo-2-[4-(1-methyl-piperidin-4-yl)-butoxy]-pyridin-4-yl}-5-chloro-4-methyl-1H-benzoimidazole; 2-{5-bromo-2-[4-(1-methyl-piperidin-4-yl)-butoxy]-pyridin-4-yl}-5-tert-butyl-1H-benzoimidazole; 5-tert-butyl-2-{2-[4-(1-methyl-piperidin-4-yl)-butoxy]-pyridin-4-yl}-1H-benzoimidazole; 2-{5-chloro-2-[4-(1-methyl-piperidin-4-yl)-butoxy]-pyridin-4-yl}-5-fluoro-4-methyl-1H-benzoimidazole; 2-{5-chloro-2-[4-(1-methyl-piperidin-4-yl)-butoxy]-pyridin-4-yl}-4,5-dimethyl-1H-benzoimidazole; 4,6-dimethyl-2-{2-[4-(4-methyl-piperazin-1-yl)-butoxy]-pyridin-4-yl}-1H-benzoimidazole; 4-methyl-2-{2-[4-(4-methyl-piperazin-1-yl)-butoxy]-pyridin-4-yl}-1H-benzoimidazole; 4,5-dimethyl-2-{2-[4-(4-methyl-piperazin-1-yl)-butoxy]-pyridin-4-yl}-1H-benzoimidazole; 5-fluoro-4-methyl-2-{2-[4-(4-methyl-piperazin-1-yl)-butoxy]-pyridin-4-yl}-1H-benzoimidazole; 6-chloro-4-methyl-2-{2-[4-(4-methyl-piperazin-1-yl)-butoxy]-pyridin-4-yl}-1H-benzoimidazole; 5-fluoro-4-methyl-2-{2-[4-(4-methyl-[1,4]diazepan-1-yl)-butoxy]-pyridin-4-yl}-1H-benzoimidazole; 4,5-dimethyl-2-{2-[4-(4-methyl-[1,4]diazepan-1-yl)-butoxy]-pyridin-4-yl}-1H-benzoimidazole; 4,6-dimethyl-2-{2-[4-(1-methyl-piperidin-4-yl)-butoxy]-pyridin-4-yl}-1H-benzoimidazole; 4-methyl-2-{2-[4-(1-methyl-piperidin-4-yl)-butoxy]-pyridin-4-yl}-1H-benzoimidazole; 5-fluoro-4-methyl-2-{2-[4-(1-methyl-piperidin-4-yl)-butoxy]-pyridin-4-yl}-1H-benzoimidazole; 4-chloro-2-{2-[4-(1-methyl-piperidin-4-yl)-butoxy]-pyridin-4-yl}-1H-benzoimidazole; 4,5-dimethyl-2-{2-[4-(1-methyl-piperidin-4-yl)-butoxy]-pyridin-4-yl}-1H-benzoimidazole; 6-chloro-4-methyl-2-{2-[4-(1-methyl-piperidin-4-yl)-butoxy]-pyridin-4-yl}-1H-benzoimidazole; 5-chloro-4-methyl-2-{2-[4-(1-methyl-piperidin-4-yl)-butoxy]-pyridin-4-yl}-1H-benzoimidazole; 5-tert-butyl-2-[2-(4-piperidin-4-yl-butoxy)-pyridin-4-yl]-1H-benzoimidazole; 4,6-dimethyl-2-[2-(4-piperidin-4-yl-butoxy)-pyridin-4-yl]-1H-benzoimidazole; 2-{2-[4-(1-ethyl-piperidin-4-yl)-butoxy]-pyridin-4-yl}-4,5-dimethyl-1H-benzoimidazole; 4,6-dimethyl-2-{3-methyl-2-[4-(1-methyl-piperidin-4-yl)-butoxy]-pyridin-4-yl}-1H-benzoimidazole; 4-methyl-2-{3-methyl-2-[4-(1-methyl-piperidin-4-yl)-butoxy]-pyridin-4-yl}-1H-benzoimidazole; 6-chloro-4-methyl-2-{3-methyl-2-[4-(1-methyl-piperidin-4-yl)-butoxy]-pyridin-4-yl}-1H-benzoimidazole; 2-{3-chloro-2-[4-(1-methyl-piperidin-4-yl)-butoxy]-pyridin-4-yl}-4-methyl-1H-benzoimidazole; 2-{3-chloro-2-[4-(1-methyl-piperidin-4-yl)-butoxy]-pyridin-4-yl}-4,5-dimethyl-1H-benzoimidazole; 4-chloro-2-{3-chloro-2-[4-(1-methyl-piperidin-4-yl)-butoxy]-pyridin-4-yl}-1H-benzoimidazole; 2-{3-chloro-2-[4-(1-methyl-piperidin-4-yl)-butoxy]-pyridin-4-yl}-5-fluoro-4-methyl-1H-benzoimidazole; 2-{3-chloro-2-[4-(1-methyl-piperidin-4-yl)-butoxy]-pyridin-4-yl}-4,6-dimethyl-1H-benzoimidazole; 6-chloro-2-{3-chloro-2-[4-(1-methyl-piperidin-4-yl)-butoxy]-pyridin-4-yl}-4-methyl-1H-benzoimidazole; 5-chloro-2-{3-chloro-2-[4-(1-methyl-piperidin-4-yl)-butoxy]-pyridin-4-yl}-4-methyl-1H-benzoimidazole; 5-fluoro-4-methyl-2-{5-methyl-2-[4-(1-methyl-piperidin-4-yl)-butoxy]-pyridin-4-yl}-1H-benzoimidazole; 5-chloro-6-fluoro-2-{5-methyl-2-[4-(1-methyl-piperidin-4-yl)-butoxy]-pyridin-4-yl}-1H-benzoimidazole; 5-tert-butyl-2-{5-methyl-2-[4-(1-methyl-piperidin-4-yl)-butoxy]-pyridin-4-yl}-1H-benzoimidazole; 4,5-dimethyl-2-{5-methyl-2-[4-(1-methyl-piperidin-4-yl)-butoxy]-pyridin-4-yl}-1H-benzoimidazole; 2-{5-chloro-2-[4-(1-methyl-piperidin-4-yl)-butoxy]-pyridin-4-yl}-1H-benzoimidazole; 5-chloro-2-{5-chloro-2-[4-(1-methyl-piperidin-4-yl)-butoxy]-pyridin-4-yl}-1H-benzoimidazole; 5-chloro-2-{5-chloro-2-[4-(1-methyl-piperidin-4-yl)-butoxy]-pyridin-4-yl}-6-fluoro-1H-benzoimidazole; 5-tert-butyl-2-{5-chloro-2-[4-(1-methyl-piperidin-4-yl)-butoxy]-pyridin-4-yl}-1H-benzoimidazole; 2-{5-bromo-2-[4-(1-methyl-piperidin-4-yl)-butoxy]-pyridin-4-yl}-4-chloro-1H-benzoimidazole; 2-{5-bromo-2-[4-(1-methyl-piperidin-4- yl)-butoxy]-pyridin-4-yl}-5-chloro-6-fluoro-1H-benzoimidazole; 2-{5-bromo-2-[4-(1-methyl-piperidin-4-yl)-butoxy]-pyridin-4-yl}-5-chloro-1H-benzoimidazole; and {4-(4,6-dimethyl-1H-benzoimidazol-2-yl)-6-[4-(1-methyl-piperidin-4-yl)-butoxy]-pyridin-3-yl}-methanol.

Compounds of formulae (X) and (XI) are histamine $H_4$ receptor ligands and are described in WO2005/092066A2 filed Mar. 24, 2005, to Buzard, et al., and in US2007/0149541A1, filed Feb. 8, 2007, to Buzard, et al., which publications are herein incorporated by reference.

Compounds of formulae

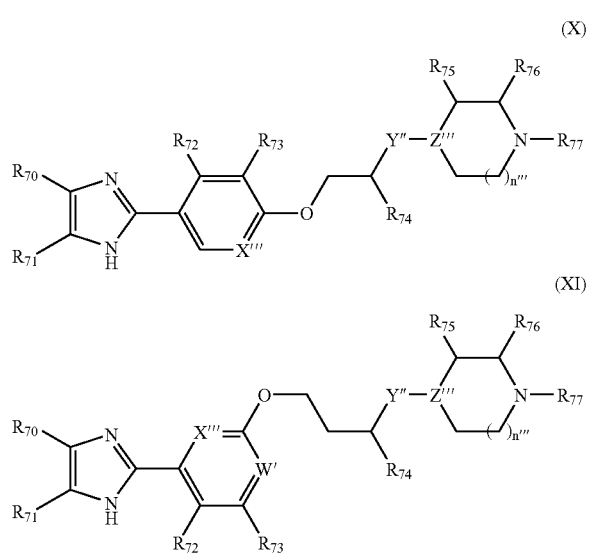

wherein:

W' is, independently from other member and substituent assignments, N or $CR_{78}$;

X''' is, independently from other member and substituent assignments, N or $CR_{78}$;

Y'' is, independently from other member and substituent assignments, O, $NR_{78}$, or $CR_{79}R_{80}$;

Z''' is, independently from other member and substituent assignments, N or $CR_{81}$;

n''' is, independently from other member and substituent assignments, 0, 1, or 2;

each of $R_{70-71}$ is, independently from other member and substituent assignments, —H, —$CF_3$, —$C_{1-6}$alkyl, —$C_{3-6}$cycloalkyl, optionally substituted aryl or optionally substituted heteroaryl; or, $R_{70}$ and $R_{71}$ taken together with the carbon atoms to which they are attached form a cyclic structure Cyc5 selected from 5- or 6-membered carbocycle, and 5- or 6-membered heterocycle with 1 heteroatom, wherein said cyclic structure Cyc5 is, independently from other substituent assignments, substituted with 0, 1, or 2 substituents selected from —$C_{1-3}$alkyl, halo, hydroxy, amino, and —$C_{1-3}$alkoxy;

each of $R_{72}$-73 and $R_{78}$ is, independently from other member and substituent assignments, —H, —$C_{1-6}$alkyl, halo, —$CF_3$, —$OCF_3$, —$OR^f$, —$SR^f$, —$S(O)R^f$, —$SO_2R^f$, $C_{1-4}$alkoxy, cyano, nitro, —$C(O)NR^dR^e$, —$C(O)$phenyl, —$C(O)C_{1-6}$alkyl, —$S(O)C_{1-4}$alkyl, or —$SO_2C_{1-4}$alkyl; or, $R_{72}$ and $R_{73}$ taken together with the carbon atoms to which they are attached form a cyclic structure Cyc6 selected from aryl, 5- or 6-membered carbocycle, and 5- or 6-membered heterocycle with 1 or 2 heteroatoms, wherein said cyclic structure Cyc6 is, independently from other substituent assignments, substituted with 0, 1, or 2 substituents selected from —$C_{1-3}$alkyl, halo, hydroxy, amino, and —$C_{1-3}$alkoxy; wherein each of $R^d$, $R^e$ and $R^f$ is, independently from other substituent assignments, selected from H, $C_{1-4}$alkyl, $C_{3-6}$cycloalkyl, phenyl, ($C_{3-6}$cycloalkyl)$C_{1-2}$alkyl, benzyl and phenethyl, or $R^d$ and $R^e$ taken together with the nitrogen to which they are attached, form a 4-7 membered heterocyclic ring HetCyc4, wherein said ring HetCyc4 has 0 or 1 additional heteroatoms selected from O, S, >NH and >$NC_{1-6}$alkyl, and wherein any phenyl, phenethyl, benzyl, alkyl or cycloalkyl moiety in any of said $R_{70-73}$, $R^d$, $R^e$, $R^f$, and said ring HetCyc4 is optionally, and independently from other substituent assignments, substituted with 1, 2 or 3 substituents selected from $C_{1-3}$alkyl, halo, hydroxy, amino, and $C_{1-3}$alkoxy;

$R_{74}$ is, independently from other member and substituent assignments, —H, —$C_{1-6}$alkyl, —$C_{1-4}$alkoxy, or hydroxy;

each of $R_{75}$ and $R_{76}$ is, independently from other member and substituent assignments, —H or —$C_{1-6}$alkyl, or $R_{75}$ and $R_{76}$ taken together form a 5-6 membered cyclic structure Cyc7, wherein said cyclic structure Cyc7 is a 5- or 6-membered carbocycle or a 5- or 6-membered heterocycle with 1 or 2 heteroatoms, and wherein said cyclic structure Cyc7 is, independently from other substituent assignments, substituted with 0, 1, or 2 substituents selected from —$C_{1-3}$alkyl, halo, hydroxy, amino, and —$C_{1-3}$alkoxy;

$R_{77}$ is, independently from other member and substituent assignments, —H or —$C_{1-4}$alkyl;

each of $R_{79}$ and $R_{80}$ is, independently from other member and substituent assignments, —H or —$C_{1-4}$alkyl; or, when Y'' is $CR_{79}R_{80}$, $R_{79}$ and $R_{80}$ taken together with the carbon member to which they are attached form an optionally substituted cyclic structure Cyc8, wherein said cyclic structure Cyc8 is a 3- to 6-membered carbocycle or a 3- to 6-membered non-aromatic heterocycle with 0 or 1 additional heteroatoms, or $CR_{79}R_{80}$ is C=O;

$R_{81}$ is independently from other member and substituent assignments, —H, —$C_{1-4}$alkyl, hydroxy, or —$C_{1-4}$alkoxy;

an enantiomer, diastereomer, racemate thereof, or a pharmaceutically acceptable salt, amide or ester thereof;

with the following provisos:
when Y'' is O or $NR_{79}$, then Z''' is $CR_{81}$ and $R_{74}$ is not hydroxy or —$C_{1-4}$alkoxy;
when Z''' is N, Y'' is $CR_{79}R_{80}$;
when $R_{70}$ and $R_{71}$ are both —H, Y'' is $CH_2$, and $R_{77}$ is methyl, then $R_{74}$ is not hydroxy.

Examples of compounds of formulae (X) and (XI) include, but are not limited to 1-(3-{4-[4,5-bis-(4-bromo-phenyl)-1H-imidazol-2-yl]-3-chloro-phenoxy}-propyl)-4-methyl-piperazine; 1-{3-[3-chloro-4-(4,5-diphenyl-1H-imidazol-2-yl]-phenoxy}-propyl)-4-methyl-piperazine; 1-(3-{4-[4,5-bis-(2-chloro-phenyl)-1H-imidazol-2-yl]-3-chloro-phenoxy}-propyl)-4-methyl-piperazine; 1-(3-{4-[4,5-bis-(4-methoxy-phenyl)-1H-imidazol-2-yl]-3-chloro-phenoxy}-propyl)-4-methyl-piperazine; 1-{3-[3-chloro-4-(4,5-di-p-tolyl-1H-imidazol-2-yl)-phenoxy]-propyl}-4-methyl-piperazine; 1-(3-{4-[4,5-bis-(4-fluoro-phenyl)-1H-imidazol-2-yl]-3-chloro-phenoxy}-propyl)-4-methyl-piperazine; 1-(3-{4-[4,5-bis-(3-methoxy-phenyl)-1H-imidazol-2-yl]-3-chloro-phenoxy}-propyl)-4-methyl-piperazine; 1-(3-{4-[4,5-bis-(3-methoxy-phenyl)-1H-imidazol-2-yl]-2-fluoro-phenoxy}-propyl)-4-methyl-piperazine; 1-(3-{4-[4,5-bis-(4-bromo-phenyl)-1H-imidazol-2-yl]-3-chloro-phenoxy}-propyl)-4-methyl-[1,4]diazepane; 1-(3-{4-[4,5-bis-(3-methoxy-phenyl)-1H-imidazol-2-yl]-3-chloro-phenoxy}-propyl)-4-methyl-[1,4]diazepane; 1-{3-[2-chloro-4-(5-methyl-4-phenyl-1H-imidazol-2-yl)-phenoxy]-propyl}-4-methyl-[1,4]diazepane; 2-{3-chloro-4-[3-(4-methyl-[1,4]diazepan-1-yl)-propoxy]-phenyl}-4,5,6,7-tetrahydro-1H-benzoimidazole; 2-{2-chloro-4-[3-(4-methyl-[1,4]diazepan-1-yl)-propoxy]-phenyl}-4,5,6,7-tetrahydro-1H-benzoimidazole; 1-methyl-4-{3-[3-methyl-4-(4-phenyl-5-trifluoromethyl-1H-imidazol-2-yl)-phenoxy]-propyl}-piperidine; 4-{3-[3-chloro-4-(4-phenyl-5-trifluoromethyl-1H-imidazol-2-yl)-phenoxy]-propyl}-piperidine; 4-(3-{3-chloro-4-[5-methyl-4-(3-trifluoromethyl-phenyl)-1H-imidazol-2-yl]-phenoxy}-propyl)-1-methyl-piperidine; 4-(3-{3-chloro-4-[4-(3,5-dichloro-phenyl)-5-methyl-1H-imidazol-2-yl]-phenoxy}-propyl)-1-methyl-piperidine; 4-(3-{4-[4-(3,5-dichloro-phenyl)-5-methyl-1H-imidazol-2-yl]-phenoxy}-propyl)-1-methyl-piperidine; 4-(3-{3-chloro-4-[4-(4-chloro-phenyl)-5-methyl-1H-imidazol-2-yl]-phenoxy}-propyl)-1-methyl-piperidine; 4-(3-{4-[4,5-bis-(4-fluoro-phenyl)-1H-imidazol-2-yl]-3-chloro-phenoxy}-propyl)-1-methyl-piperidine; 4-(3-{4-[4,5-bis-(3-methoxy-phenyl)-1H-imidazol-2-yl]-3-chloro-phenoxy}-propyl)-1-methyl-piperidine; 4-(3-{3-chloro-[4-(4-chloro-phenyl)-5-p-tolyl-1H-imidazol-2-yl]-phenoxy}-propyl)-1-methyl-piperidine; 2-{2-chloro-4-[3-(1-methyl-piperidin-4-yl)-propoxy]-phenyl-4,5,6,7-tetrahydro-1H-benzoimidazole; 4-{3-[3-chloro-4-(4-methyl-5-propyl-1H-imidazol-2-yl)-phenoxy]-propyl}-1-methyl-piperidine; 4-{3-[3-chloro-4-(5-ethyl-4-methyl-1H-imidazol-2-yl)-phenoxy]-propyl}-1-methylpiperidine; 1-methyl-4-(2-{3-methyl-4-[5-methyl-4-(3-trifluoromethyl-phenyl)-1H-imidazol-2-yl]-phenoxy)-ethoxy)-piperidine; 5-[4-(3,5-dichloro-phenyl)-5-methyl-1H-imidazol-2-yl]-2-[3-(1-methyl-piperidin-4-yl)-propoxy]-pyridine; 5-[4-(4-chloro-phenyl)-5-methyl-1H-imidazol-2-yl]-2-[3-(1-methyl-piperidin-4-yl)-propoxy]-pyridine; 2-[3-(1-methyl-piperidin-4-yl)-propoxy]-5-[5-methyl-4-(3-trifluoromethyl-phenyl)-1H-imidazol-2-yl]-pyridine; 2-[3-(1-methyl-piperidin-4-yl)-propoxy]-5-[5-methyl-4-(4-trifluoromethyl-phenyl)-1H-imidazol-2-yl]-pyridine; 2-[3-(1-methyl-piperidin-4-yl)-propoxy]-5-(4-phenyl-5-trifluoromethyl-1H-imidazol-2-yl)-pyridine; 1-methyl-4-(3-{5-[5-methyl-4-(4-trifluoromethyl-phenyl)-1H-imidazol-2-yl]-pyridin-2-yloxy}-propyl)-piperazine; 1-methyl-4-(3-{5-[5-methyl-4-(3-trifluoromethyl-phenyl)-1H-imidazol-2-yl]-pyridin-2-yloxy}-propyl)-piperazine; 4-(4-{3-[4-(4-chloro-phenyl)-5-methyl-1H-imidazol-2-yl]-phenoxy)-butyl)-1-methyl-piperidine; 1-methyl-4-{4-[3-(4-phenyl-5-trifluoromethyl-1H-imidazol-2-yl)-phenoxy]-butyl}-piperidine; 2-[4-(1-methyl-piperidin-4-yl)-butoxy]-4-(4-phenyl-5-trifluoromethyl-1H-imidazol-2-yl)-pyridine; 2-[4-(1-methyl-piperidin-4-yl)-butoxy]-4-[5-methyl-4-(3-trifluoromethyl-phenyl)-1H-imidazol-2-yl]-pyridine; 4-{3-[4-(5-isobutyl-4-methyl-1H-imidazol-2-yl)-3-methyl-phenoxy]-propyl}-1-methyl-piperidine; 4-[4-(4-chloro-phenyl)-5-methyl-1H-imidazol-2-yl]-2-[4-(1-methyl-piperidin-4-yl)-butoxy]-pyridine; 4-(3-[3-chloro-4-(5-isobutyl-4-methyl-1H-imidazol-2-yl)-phenoxy]-propyl}-1-methyl-piperidine; 1-methyl-4-(4-{3-[5-methyl-4-(4-trifluoromethyl-phenyl)-1H-imidazol-2-yl]-phenoxy}-butyl)-piperidine; 1-{3-[2-chloro-4-(1H-imidazol-2-yl)-phenoxy]-propyl}-4-methyl-piperazine; 1-{3-[3-chloro-4-(4,5-dimethyl-1H-imidazol-2-yl)-phenoxy]-propyl}-4-methyl-piperazine; 1-{3-[3-chloro-4-(4-phenyl-5-trifluoromethyl-1H-imidazol-2-yl)-phenoxy]-propyl}-4-methyl-piperazine; 1-{3-[2-chloro-4-(4-phenyl-5-trifluoromethyl-1H-imidazol-2-yl)-phenoxy]-propyl}-4-methyl-[1,4]diazepane; 1-methyl-4-(3-{3-methyl-4-[5-methyl-4-(3-trifluoromethyl-phenyl)-1H-imidazol-2-yl]-phenoxy}-propyl)-piperidine; 4-(3-{4-[4-(4-chloro-phenyl)-5-methyl-1H-imidazol-2-yl]-3-methyl-phenoxy}-propyl)-1-methyl-piperidine; 4-(2-{4-[4-(4-chloro-phenyl)-5-methyl-1H-imidazol-2-yl]-3-methyl-phenoxy}-ethoxy)-1-methyl-piperidine; 1-(3-{4-[4-(4-chloro-phenyl)-5-methyl-1H-imidazol-2-yl]-3-methyl-phenoxy}-2-methyl-propyl)-4-methyl-piperazine; 2-[4-(4-chloro-phenyl)-5-methyl-1H-imidazol-2-yl]-6-[4-(1-methyl-piperidin-4-yl)-butoxy]-pyridine; 4-methyl-2-[3-(1-methyl-piperidin-4-yl)-propoxy]-5-[5-methyl-4-(3-trifluoromethyl-phenyl)-1H-imidazol-2-yl]-pyridine; 5-bromo-4-[4-(4-chloro-phenyl)-5-methyl-1H-imidazol-2-yl]-2-[4-(1-methyl-piperidin-4-yl)-butoxy]-pyridine; 2,4-dimethyl-1-{3-[4-(4-phenyl)-5-trifluoromethyl-1H-imidazol-2-yl)-phenoxy]-propyl}-piperazine; 1,2-dimethyl-4-{3-[4-(4-phenyl-5-trifluoromethyl-1H-imidazol-2-yl)-phenoxy]-propyl}-piperazine; 3-chloro-2-[4-(1-methyl-piperidin-4-yl)-butoxy]-4-(4-phenyl-5-trifluoromethyl-1H-imidazol-2-yl)-pyridine; 1-methyl-4-(4-{4-[5-methyl-4-(3-trifluoromethyl-phenyl)-1H-imidazol-2-yl]-pyridin-2-yloxy}-butyl-[1,4]diazepane; 5-bromo-2-[4-(1-methyl-piperidin-4-yl)-butoxy]-4-[5-methyl-4-(3-trifluoromethyl-phenyl)-1H-imidazol-2-yl]-pyridine; 4-[4-(4-chloro-phenyl)-5-trifluoromethyl-1H-imidazol-2-yl]-2-[4-(1-methyl-piperidin-4-yl)-butoxy]-pyrimidine; 4-(3-{4-[5-cyclopropylmethyl-4-(3-trifluoromethyl-phenyl)-1H-imidazol-2-yl]-3-methyl-phenoxy}-propyl)-1-methyl-piperidine; 1-{4-[4-(4-chloro-phenyl)-5-methyl-1H-imidazol-2-yl]-3-methyl-phenoxy}-3-(4-methyl-piperazin-1-yl)-propan-2-ol; 4-(3-{3-chloro-4-[4-(4-chloro-phenyl)-5-methyl-1H-imidazol-2-yl]-phenoxy}-propyl)-piperidine; 4-(3-{3-chloro-4-[4-(4-chloro-phenyl)-5-methyl-1H-imidazol-2-yl]-phenoxy}-propyl)-1-ethyl-piperidine; 4-(3-{3-chloro-4-[4-(4-chloro-phenyl)-5-methyl-1H-imidazol-2-yl]-phenoxy}-propyl)-1-isopropyl-piperidine; 1-methyl-4-{3-[4-(4-phenyl-5-trifluoromethyl-1H-imidazol-2-yl)-naphthalen-1-yloxy]-propyl}-piperidine; 1-(4-methyl-piperazin-1-yl)-3-{5-[5-methyl-4-(4-trifluoromethyl-phenyl)-1H-imidazol-2-yl]-pyridin-2-yloxy}-propan-1-one; 6-[4-(4-chloro-phenyl)-5-methyl-1H-imidazol-2-yl]-3-fluoro-2-[4-(1-methyl-piperidin-4-yl)-butoxy]-pyridine; 1-methyl-4-(4-{3-methyl-6-[5-methyl-4-(3-trifluoromethyl-phenyl)-1H-imidazol-2-yl]-pyridin-2-yloxy}-butyl)-piperazine; 1-methyl-4-{3-[4-(5-methyl-4-thiophen-2-yl-1H-imidazol-2-yl)-phenoxy]propyl}-piperidine; and 2-{3-[4-(1-methyl-piperidin-4-yl)-butoxy]-phenyl}-3H-imidazo[4,5-b]pyridine.

DEFINITION OF TERMS

Certain terms as used in the specification are intended to refer to the following definitions, as detailed below.

The term "acyl" as used herein means an alkyl group, as defined herein, appended to the parent molecular moiety through a carbonyl group, as defined herein. Representative examples of acyl include, but are not limited to, acetyl, 1-oxopropyl, 2,2-dimethyl-1-oxopropyl, 1-oxobutyl, and 1-oxopentyl.

The term "acyloxy" as used herein means an acyl group, as defined herein, appended to the parent molecular moiety through an oxygen atom. Representative examples of acyloxy include, but are not limited to, acetyloxy, propionyloxy, and isobutyryloxy.

The term "alkenyl" as used herein means a straight or branched chain hydrocarbon containing from 2 to 10 carbons, and preferably 2, 3, 4, 5, or 6 carbons, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkyl" as used herein means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" as used herein means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxyimino" as used herein means an alkoxy group, as defined herein, appended to the parent molecular moiety through a —C(=NH)— group, which also is defined as an imino group. Representative examples of alkoxyimino include, but are not limited to, imino(methoxy)methyl, ethoxy(imino)methyl and tert-butoxy(imino)methyl.

The term "alkoxysulfonyl" as used herein means an alkoxy group, as defined herein, appended to the parent molecular moiety through a sulfonyl group, as defined herein. Representative examples of alkoxysulfonyl include, but are not limited to, methoxysulfonyl, ethoxysulfonyl, and propoxysulfonyl.

The term "alkyl" as used herein means a straight or branched chain hydrocarbon containing from 1 to 10 carbon atoms, and preferably 1, 2, 3, 4, 5, or 6 carbons. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" means a divalent group derived from a straight or branched chain hydrocarbon of from 1 to 10 carbon atoms. Representative examples of alkylene include, but are not limited to, —CH$_2$—, —CH(CH$_3$)—, —C(CH$_3$)$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkylamino" as used herein means an alkyl group, as defined herein, appended to the parent molecular moiety through a NH group. Representative examples of alkylamino include, but are not limited to, methylamino, ethylamino, isopropylamino, and butylamino.

The term "alkylcarbonyl" as used herein means an alkyl group, as defined herein, appended to the parent molecular moiety through a carbonyl group, as defined herein. Representative examples of alkylcarbonyl include, but are not limited to, methylcarbonyl, ethylcarbonyl, isopropylcarbonyl, n-propylcarbonyl, and the like.

The term "alkylcycloalkyl" as used herein means a cycloalkyl group as defined herein, attached to an alkylene moiety, attached to the parent molecular moiety through the alkylene group. Representative examples of alkylcycloalkyl include, but are not limited to, cyclopropylmethyl, cyclohexylethyl and the like.

The term "alkylfluorocycloalkyl" as used herein means a fluorocycloalkyl group as defined herein, attached to an alkylene moiety, attached to the parent molecular moiety through the alkylene group. Representative examples of alkylfluorocycloalkyl include, but are not limited to, (4-fluorocyclohexyl)methyl, (2,2-difluorocyclobutyl)methyl and the like.

The term "alkylsulfonyl" as used herein means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylthio" as used herein, means an alkyl group, as defined herein, appended to the parent molecular moiety through a sulfur atom. Representative examples of alkylthio include, but are not limited, methylthio, ethylthio, tert-butylthio, and hexylthio.

The term "alkynyl" as used herein means a straight or branched chain hydrocarbon group containing from 2 to 10 carbon atoms, and preferably 2, 3, 4, or 5 carbons, and containing at least one carbon-carbon triple bond. Representative examples of alkynyl include, but are not limited to, acetylenyl, 1-propynyl, 2-propynyl, 3-butynyl, 2-pentynyl, and 1-butynyl.

The term "amido" as used herein means an amino, alkylamino, or dialkylamino group appended to the parent molecular moiety through a carbonyl group, as defined herein. Representative examples of amido include, but are not limited to, aminocarbonyl, methylaminocarbonyl, dimethylaminocarbonyl, and ethylmethylaminocarbonyl.

The term "amino" as used herein means an —NH$_2$ group.

The term "aryl," as used herein, means phenyl, a bicyclic aryl, or a tricyclic aryl. The bicyclic aryl is naphthyl, a phenyl fused to a cycloalkyl, or a phenyl fused to a cycloalkenyl. The bicyclic aryl of the invention must be attached to the parent molecular moiety through any available carbon atom contained within the phenyl ring. Representative examples of the bicyclic aryl include, but are not limited to, dihydroindenyl, indenyl, naphthyl, dihydronaphthalenyl, and tetrahydronaphthalenyl. The tricyclic aryl is anthracene or phenanthrene, a bicyclic aryl fused to a cycloalkyl, a bicyclic aryl fused to a cycloalkenyl, or a bicyclic aryl fused to a phenyl. The tricyclic aryl is attached to the parent molecular moiety through any carbon atom contained within a phenyl ring. Representative examples of tricyclic aryl ring include, but are not limited to, azulenyl, dihydroanthracenyl, fluorenyl, and tetrahydrophenanthrenyl.

The carbon atoms of the aryl groups of this invention are substituted with hydrogen or are optionally substituted with substituents independently selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amido, carboxy, cyano, cycloalkyl, fluoroalkoxy, formyl, haloalkoxy, haloalkyl, halogen, hydroxy, hydroxyalkyl, mercapto, nitro, alkylthio, —$NR_8R_9$, ($NR_8R_9$) carbonyl, —$SO_2NR_8R_9$, and $N(R_8)SO_2(R_9)$. Where the aryl group is a phenyl group, the number of substituents is 0, 1, 2, 3, 4, or 5. Where the aryl group is a bicyclic aryl, the number of substituents is 0, 1, 2, 3, 4, 5, 6, or 7. Where the aryl group is a tricyclic aryl, the number of substituents is 0, 1, 2, 3, 4, 5, 6, 7, 8, or 9.

The term "arylalkyl" as used herein means an aryl group, as defined herein, appended to the parent molecular moiety through an alkyl group, as defined herein. Representative examples of arylalkyl include, but are not limited to, benzyl, 2-phenylethyl and 3-phenylpropyl.

The term "carbonyl" as used herein means a —C(═O)— group.

The term "carboxy" as used herein means a —$CO_2H$ group.

The term "cyano" as used herein means a —CN group, attached to the parent molecular moiety through the carbon.

The term "cyanoalkyl" as used herein means a —CN group attached to an alkylene, appended to the parent molecular moiety through the alkylene group. Representative examples of "cyanoalkyl" include, but are not limited to, 3-cyanopropyl, and 4-cyanobutyl.

The term "cyanophenyl" as used herein means a —CN group appended to the parent molecular moiety through a phenyl group, including, but not limited to, 4-cyanophenyl, 3-cyanophenyl, and 2-cyanophenyl.

The term "cycloalkyl" as used herein means a saturated cyclic hydrocarbon group containing from 3 to 10 carbons. Examples of cycloalkyl include cyclopropyl, cyclobutyl, cyclopentyl, cyclohexyl, cycloheptyl, and cyclooctyl. $C_3$-$C_5$ cycloalkyl in particular refers to a saturated cyclic hydrocarbon group containing from 3 to 5 carbons, for example, cyclopropyl, cyclobutyl, and cyclopentyl.

The term "cycloalkenyl" as used herein means a cyclic hydrocarbon group containing from 3 to 10 carbons, containing 1 or 2 carbon-carbon double bonds. Examples of cycloalkenyl include cyclopropenyl, cyclobutenyl, cyclopentenyl, cyclohexenyl, cycloheptenyl, and cyclooctenyl.

Each of the carbon atoms of the cycloalkyl or cycloalkenyl groups of the invention is substituted with 0, 1, or 2 substituents selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amido, carboxy, cyano, fluoroalkoxy, formyl, haloalkoxy, haloalkyl, halogen, hydroxy, hydroxyalkyl, mercapto, oxo, nitro, alkylthio, —$NR_8R_9$, ($NR_8R_9$)carbonyl, —$SO_2N(R_8)(R_9)$, and —$N(R_8)SO_2(R_9)$, wherein $R_8$ and $R_9$ are defined herein.

The term "cycloalkoxyalkyl" as used herein means a cycloalkyl group, as defined herein, appended to the parent molecular moiety through an —O-alkyl-group, wherein alkyl is as defined herein. Representative examples of cycloalkoxylalkyl include, but are not limited to, cyclobutoxymethyl, cyclopentyloxymethyl, 2-(cyclopentyloxy)ethyl and cyclohexyloxymethyl.

The term "cycloalkylcarbonyl" as used herein means a cycloalkyl group, as defined herein, appended to the parent molecular moiety through a carbonyl group, as defined herein. Representative examples of cycloalkylcarbonyl include, but are not limited to, cyclopropylcarbonyl, cyclopentylcarbonyl, cyclohexylcarbonyl, and cycloheptylcarbonyl.

The term "cycloalkylalkyl" as used herein means a cycloalkyl group, as defined herein, appended to the parent molecular moiety through an alkyl group, as defined herein. Representative examples of cycloalkylalkyl include, but are not limited to, cyclopropylmethyl, cyclopentylmethyl, cyclohexylmethyl, and cycloheptylmethyl. ($C_3$-$C_5$ cycloalkyl)alkyl in particular refers to a saturated cyclic hydrocarbon group containing from 3 to 5 carbons, for example, cyclopropyl, cyclobutyl, and cyclopentyl, appended to the parent molecular moiety through a alkyl group.

The term "dialkylamino" as used herein means two independent alkyl groups, as defined herein, appended to the parent molecular moiety through a nitrogen atom. Representative examples of dialkylamino include, but are not limited to, dimethylamino, diethylamino, ethylmethylamino, and butylmethylamino.

The term "fluoro" as used herein means —F.

The term "fluoroalkyl" as used herein means at least one fluoro group, appended to the parent molecular moiety through an alkyl group, as defined herein. Representative examples of fluoroalkyl include, but are not limited to, fluoromethyl, difluoromethyl, trifluoromethyl, pentafluoroethyl, and 2,2,2-trifluoroethyl.

The term "fluoroalkoxy" as used herein means at least one fluoro group, appended to the parent molecular moiety through an alkoxy group, as defined herein. Representative examples of fluoroalkoxy include, but are not limited to, fluoromethoxy, difluoromethoxy, trifluoromethoxy, pentafluoroethoxy, and 2,2,2-trifluoroethoxy.

The term "formyl" as used herein means a —C(O)H group.

The term "halo" or "halogen" as used herein means Cl, Br, I, or F.

The term "haloalkoxy" as used herein means at least one halogen, as defined herein, appended to the parent molecular moiety through an alkoxy, as defined herein. Representative examples of haloalkoxy include, but are not limited to, 2-fluoroethoxy, trifluoromethoxy, and pentafluoroethoxy.

The term "haloalkyl" as used herein means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heterocycle", as used herein, refers to non-aromatic cyclic groups that contain at least one heteroatom. Non-aromatic heterocycles are non-aromatic cyclic groups that contain at least one heteroatom; examples of non-aromatic heterocyclic groups or non-aromatic heterocycles are further defined below. Heterocyclic rings are connected to the parent molecular moiety through a carbon atom, or alternatively in the case of heterocyclic rings that contain a bivalent nitrogen atom having a free site for attachment, the heterocyclic ring may be connected to the parent molecular moiety though a nitrogen atom. Additionally, the heterocycles may be present as tautomers.

The term "heteroaryl", as used herein, refers to an aromatic ring containing one or more heteroatoms independently selected from nitrogen, oxygen, and sulfur. Such rings can be monocyclic or bicyclic as further described herein.

The terms "monocyclic heteroaryl" or "5- or 6-membered heteroaryl ring", as used herein, refer to 5- or 6-membered aromatic rings containing at least one heteroatom independently selected from nitrogen, oxygen, and sulfur. The 5-membered ring contains two double bonds; such a ring may contain one, two, three or four nitrogen atoms, or may contain one or two nitrogen atoms and one oxygen atom, or may contain one or two nitrogen atoms and one sulfur atom, or may contain one oxygen atom, or may contain one sulfur atom. The 6-membered ring contains three double bonds, or alternatively, the 6-membered ring may contains 2 double bonds within the ring when the ring is substituted with an oxo group. Furthermore, the 6-membered ring may contain one, two, three or four nitrogen atoms, or may contain one or two nitrogen atoms and one oxygen atom, or may contain one or two nitrogen atoms and one sulfur atom, or may contain one or two nitrogen atoms and one sulfur atom, or may contain one or two nitrogen atoms and or one oxygen atom. The 5- or 6-membered heteroaryl is connected to the parent molecular moiety through any carbon atom or any nitrogen atom contained within the monocyclic heteroaryl ring. Representative examples of 5- to 6-membered heteroaryl rings include, but are not limited to, furyl, imidazolyl, isoxazolyl, isothiazolyl, oxazolyl, pyrazinyl, pyrazolyl, pyridazinyl, pyridinyl, pyrimidinyl, pyrrolyl, tetrazolyl, thiadiazolyl, thiadiazolonyl, thiadiazinonyl, oxadiazolyl, oxadiazolonyl, oxadiazinonyl, thiazolyl, thienyl, triazinyl, triazolyl, triazolyl, pyridazinonyl, pyridonyl, and pyrimidinonyl.

The term "bicyclic heteroaryl" or "8- to 12-membered bicyclic heteroaryl ring", as used herein, refers to an 8-, 9-, 10-, 11-, or 12-membered bicyclic aromatic ring wherein one or more of the atoms of the ring has been replaced with at least one heteroatom selected from oxygen, sulfur, and nitrogen. The bicyclic heteroaryl of the invention maybe attached to the parent molecular moiety through any available carbon atom or nitrogen atom contained within the heteroaryl ring. Representative examples of bicyclic heteroaryl rings include indolyl, benzothienyl, benzofuranyl, indazolyl, benzimidazolyl, benzothiazolyl, benzoxazolyl, benzoisothiazolyl, benzoisoxazolyl, quinolinyl, isoquinolinyl, quinazolinyl, quinoxalinyl, phthalazinyl, pteridinyl, purinyl, naphthyridinyl, cinnolinyl, thieno[2,3-d]imidazole, 1,5-dihydro-benzo[b][1,4]diazepin-2-on-yl, and pyrrolopyrimidinyl.

Heteroaryl groups of the invention, whether monocyclic or bicyclic, are substituted with hydrogen, or optionally substituted with substituents independently selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkylthio, alkynyl, amido, carboxy, cyano, cycloalkyl, fluoroalkoxy, formyl, haloalkoxy, haloalkyl, halogen, hydroxy, hydroxyalkyl, mercapto, nitro, oxo, —NR$^8$R$^9$, (NR$^8$R$^9$)carbonyl, —SO$_2$N(R$^8$)(R$^9$), and —N(R$^8$)SO$_2$(R$^9$). Monocyclic heteroaryl or 5- or 6-membered heteroaryl rings are substituted with 0, 1, 2, 3, 4, or 5 substituents. Bicyclic heteroaryl or 8- to 12-membered bicyclic heteroaryl rings are substituted with 0, 1, 2, 3, 4, 5, 6, 7, 8, or 9 substituents. Heteroaryl groups of the invention may be present as tautomers.

The term "heterocycle" or "heterocyclic" as used herein, means a monocyclic heterocycle or a bicyclic heterocycle. The monocyclic heterocycle is a 3, 4, 5, 6 or 7 membered ring containing at least one heteroatom independently selected from the group consisting of O, N, and S. The 3- or 4-membered ring contains 1 heteroatom selected from the group consisting of O, N and S. The 5-membered ring contains zero or one double bond and one, two or three heteroatoms selected from the group consisting of O, N and S. The 6- or 7-membered ring may contain zero, one, or two double bonds provided that the ring, when taken together with a substituent, does not tautomerize with a substituent to form an aromatic ring. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, a monocyclic heterocycle fused to a cycloalkyl, a monocyclic heterocycle fused to a cycloalkenyl, or a monocyclic heterocycle fused to a monocyclic heterocycle. The bicyclic heterocycle is connected to the parent molecular moiety through any carbon atom or any nitrogen atom contained within the monocyclic heterocycle. Representative examples of bicyclic heterocycle include, but are not limited to, 1,3-benzodioxolyl, 1,3-benzodithiolyl, 2,3-dihydro-1,4-benzodioxinyl, 2,3-dihydro-1-benzofuranyl, 2,3-dihydro-1-benzothienyl, 2,3-dihydro-1H-indolyl, and 1,2,3,4-tetrahydroquinolinyl.

The non-aromatic heterocycles of the invention substituted with hydrogen, or optionally substituted with 0, 1, 2, 3, 4, 5, 6, 7, 8, or 9 substituents independently selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amido, carboxy, cyano, cycloalkyl, fluoroalkoxy, formyl, haloalkoxy, haloalkyl, halogen, hydroxy, hydroxyalkyl, mercapto, nitro, alkylthio, —$NR_8R_9$, ($NR_8R_9$)carbonyl, —$SO_2N(R_8)(R_9)$, and —$N(R_8)SO_2(R_9)$.

The term "hydroxy" as used herein means an —OH group.

The term "hydroxyalkyl" as used herein means at least one hydroxy group, as defined herein, appended to the parent molecular moiety through an alkyl group, as defined herein. Representative examples of hydroxyalkyl include, but are not limited to, hydroxymethyl, 2-hydroxyethyl, 2-methyl-2-hydroxyethyl, 3-hydroxypropyl, 2,3-dihydroxypentyl, and 2-ethyl-4-hydroxyheptyl.

The term "hydroxy-protecting group" means a substituent which protects hydroxyl groups against undesirable reactions during synthetic procedures. Examples of hydroxy-protecting groups include, but are not limited to, methoxymethyl, benzyloxymethyl, 2-methoxyethoxymethyl, 2-(trimethylsilyl)ethoxymethyl, benzyl, triphenylmethyl, 2,2,2-trichloroethyl, t-butyl, trimethylsilyl, t-butyldimethylsilyl, t-butyldiphenylsilyl, methylene acetal, acetonide benzylidene acetal, cyclic ortho esters, methoxymethylene, cyclic carbonates, and cyclic boronates. Hydroxy-protecting groups are appended onto hydroxy groups by reaction of the compound that contains the hydroxy group with a base, such as triethylamine, and a reagent selected from an alkyl halide, alkyl triflate, trialkylsilyl halide, trialkylsilyl triflate, aryldialkylsilyltriflate, or an alkylchloroformate, $CH_2I_2$, or a dihaloboronate ester, for example with methyliodide, benzyl iodide, triethylsilyltriflate, acetyl chloride, benzylchloride, or dimethylcarbonate. A protecting group also may be appended onto a hydroxy group by reaction of the compound that contains the hydroxy group with acid and an alkyl acetal.

The term "imino" as defined herein means a —C(=NH)— group.

The term "mercapto" as used herein means a —SH group.

The term "($NR_8R_9$)" as used herein means both an $R_8$ and $R_9$ group, as defined herein, are appended to the parent molecular moiety through a nitrogen atom. The "($NR_8R_9$)" is appended to the parent molecular moiety through the nitrogen.

The term "($NR_8R_9$)alkyl" as used herein means an —$NR_8R_9$ group, as defined herein, appended to the parent molecular moiety through an alkylene group, as defined herein. Representative examples of ($NR_8R_9$)alkyl include, but are not limited to, 2-(methylamino)ethyl, 2-(dimethylamino)ethyl, 2-(amino)ethyl, 2-(ethylmethylamino)ethyl, and the like.

The term "($NR_8R_9$)carbonyl" as used herein means an —$NR_8R_9$ group, as defined herein, appended to the parent molecular moiety through a carbonyl group, as defined herein. Representative examples of ($NR_8R_9$)carbonyl include, but are not limited to, aminocarbonyl, (methylamino)carbonyl, (dimethylamino)carbonyl, (ethylmethylamino)carbonyl, and the like.

The term "($NR_8R_9$)sulfonyl" as used herein means a —$NR_8R_9$ group, as defined herein, appended to the parent molecular moiety through a sulfonyl group, as defined herein. Representative examples of ($NR_8R_9$)sulfonyl include, but are not limited to, aminosulfonyl, (methylamino)sulfonyl, (dimethylamino)sulfonyl and (ethylmethylamino)sulfonyl.

The term "—$N(R_8)SO_2(R_9)$" as used herein means an amino group attached to the parent moiety to which is further appended with a $R_8$ group as defined herein, and a $SO_2$ group to which is appended an ($R_9$) group as defined herein. Representative examples of —$N(R_8)SO_2(R_9)$ include, but are not limited to, N-methylmethanesulfonamide.

The term "—$SO_2(NR_8R_9)$" as used herein means a $NR_8R_9$ group attached to a $SO_2$ group, appended to the parent moiety through the sulfonyl group. Representative examples of —$SO_2(NR_8R_9)$ include, but are not limited to (dimethylamino)sulfonyl and N-cyclohexyl-N-methylsulfonyl.

The term "($NR_{38}R_{39}$)" as used herein means both an $R_{38}$ and $R_{39}$ group, as defined herein, are appended to the parent molecular moiety through a nitrogen atom. The "($NR_{38}R_{39}$)" is appended to the parent molecular moiety through the nitrogen.

The term "($NR_{38}R_{39}$)alkyl" as used herein means an —$NR_{38}R_{39}$ group, as defined herein, appended to the parent molecular moiety through an alkylene group, as defined herein. Representative examples of ($NR_{38}R_{39}$)alkyl include, but are not limited to, 2-(methylamino)ethyl, 2-(dimethylamino)ethyl, 2-(amino)ethyl, 2-(ethylmethylamino)ethyl, and the like.

The term "($NR_{38}R_{39}$)carbonyl" as used herein means an —$NR_{38}R_{39}$ group, as defined herein, appended to the parent molecular moiety through a carbonyl group, as defined herein. Representative examples of ($NR_{38}R_{39}$)carbonyl include, but are not limited to, aminocarbonyl, (methylamino)carbonyl, (dimethylamino)carbonyl, (ethylmethylamino)carbonyl, and the like.

The term "($NR_{38}R_{39}$)sulfonyl" as used herein means a —$NR_{38}R_{39}$ group, as defined herein, appended to the parent molecular moiety through a sulfonyl group, as defined herein. Representative examples of ($NR_{38}R_{39}$)sulfonyl include, but are not limited to, aminosulfonyl, (methylamino)sulfonyl, (dimethylamino)sulfonyl and (ethylmethylamino)sulfonyl.

The term "—$N(R_{38})SO_2(R_{39})$" as used herein means an amino group attached to the parent moiety to which is further appended with a $R_{38}$ group as defined herein, and a $SO_2$ group to which is appended an ($R_{39}$) group as defined herein. Representative examples of —$N(R_{38})SO_2(R_{39})$ include, but are not limited to, N-methylmethanesulfonamide.

The term "—$SO_2(NR_{38}R_{39})$" as used herein means a $NR_{38}R_{39}$ group attached to a $SO_2$ group, appended to the parent moiety through the sulfonyl group. Representative examples of —$SO_2(NR_{38}R_{39})$ include, but are not limited to (dimethylamino)sulfonyl and N-cyclohexyl-N-methylsulfonyl.

The term "($NR_{48}R_{49}$)" as used herein means both an $R_{48}$ and $R_{49}$ group, as defined herein, are appended to the parent molecular moiety through a nitrogen atom. The "($NR_{48}R_{49}$)" is appended to the parent molecular moiety through the nitrogen.

The term "($NR_{48}R_{49}$)alkyl" as used herein means an —$NR_{48}R_{49}$ group, as defined herein, appended to the parent molecular moiety through an alkylene group, as defined herein. Representative examples of ($NR_{48}R_{49}$)alkyl include, but are not limited to, 2-(methylamino)ethyl, 2-(dimethylamino)ethyl, 2-(amino)ethyl, 2-(ethylmethylamino)ethyl, and the like.

The term "($NR_{48}R_{49}$)carbonyl" as used herein means an —$NR_{48}R_{49}$ group, as defined herein, appended to the parent molecular moiety through a carbonyl group, as defined herein. Representative examples of $(NR_{48}R_{49})$carbonyl include, but are not limited to, aminocarbonyl, (methylamino)carbonyl, (dimethylamino)carbonyl, (ethylmethylamino) carbonyl, and the like.

The term "$(NR_{48}R_{49})$sulfonyl" as used herein means a —$NR_{48}R_{49}$ group, as defined herein, appended to the parent molecular moiety through a sulfonyl group, as defined herein. Representative examples of $(NR_{48}R_{49})$sulfonyl include, but are not limited to, aminosulfonyl, (methylamino)sulfonyl, (dimethylamino)sulfonyl and (ethylmethylamino)sulfonyl.

The term "—$N(R_{48})SO_2(R_{49})$" as used herein means an amino group attached to the parent moiety to which is further appended with a $R_{48}$ group as defined herein, and a $SO_2$ group to which is appended an $(R_{49})$ group as defined herein. Representative examples of —$N(R_{48})SO_2(R_{49})$ include, but are not limited to, N-methylmethanesulfonamide.

The term "—$SO_2 (NR_{48}R_{49})$" as used herein means a $NR_{48}R_{49}$ group attached to a $SO_2$ group, appended to the parent moiety through the sulfonyl group. Representative examples of —$SO_2 (NR_{48}R_{49})$ include, but are not limited to (dimethylamino)sulfonyl and N-cyclohexyl-N-methylsulfonyl.

The term "nitro" as used herein means a —$NO_2$ group.

The term "nitrogen protecting group" as used herein means those groups intended to protect a nitrogen atom against undesirable reactions during synthetic procedures. Nitrogen protecting groups comprise carbamates, amides, N-benzyl derivatives, and imine derivatives. Preferred nitrogen protecting groups are acetyl, benzoyl, benzyl, benzyloxycarbonyl (Cbz), formyl, phenylsulfonyl, pivaloyl, tert-butoxycarbonyl (Boc), tert-butylacetyl, trifluoroacetyl, and triphenylmethyl (trityl). Nitrogen-protecting groups are appended onto primary or secondary amino groups by reacting the compound that contains the amine group with base, such as triethylamine, and a reagent selected from an alkyl halide, an alkyl triflate, a dialkyl anhydride, for example as represented by an alkyl anhydride (alkyl-OC=O)$_2$O, a diaryl anhydride, for example as represented by (aryl-OC=O)$_2$O, an acyl halide, an alkylchloroformate, or an alkylsulfonylhalide, an arylsulfonylhalide, or halo-CON(alkyl)$_2$, for example acetylchloride, benzoylchloride, benzylbromide, benzyloxycarbonylchloride, formylfluoride, phenylsulfonylchloride, pivaloylchloride, (tert-butyl-O—C=O)$_2$O, trifluoroacetic anhydride, and triphenylmethylchloride.

The term "oxo" as used herein means (=O).

The term "sulfonyl" as used herein means a —$S(O)_2$— group.

There also exist a pharmaceutical composition comprising a compound of formula (I)-(XI) and a pharmaceutically acceptable carrier.

The histamine $H_4$ receptor ligands may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The invention contemplates various stereoisomers and mixtures thereof and these are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by resolution well known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Histamine $H_4$ receptor ligands useful for the method may exist as cis or trans isomers, wherein substituents on a ring may attached in such a manner that they are on the same side of the ring (cis) relative to each other, or on opposite sides of the ring relative to each other (trans). Such methods are well known to those of ordinary skill in the art, and may include separation of isomers by recrystallization or chromatography. It should be understood that the compounds of the invention may possess tautomeric forms, as well as geometric isomers, and that these also constitute an aspect of the invention.

Compositions comprising a therapeutically effective amount of a compound of formulae (I)-(XI) in combination with a pharmaceutically acceptable carrier also are suitable for the method. The compositions comprise a histamine $H_4$ receptor ligand of the invention formulated together with one or more non-toxic pharmaceutically acceptable carriers. The pharmaceutical compositions can be formulated for oral administration in solid or liquid form, for parenteral intravenous, subcutaneous, intramuscular, intraperitoneal, intra-arterial, or intradermal injection, for or for vaginal, nasal, topical, or rectal administration.

The term "pharmaceutically acceptable carrier", as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

Compositions comprising a therapeutically effective amount of a compound of formulae (I)-(XI) in combination with a pharmaceutically acceptable carrier also are suitable for the method. The compositions comprise a histamine H₄ receptor ligand of the invention formulated together with one or more non-toxic pharmaceutically acceptable carriers. The pharmaceutical compositions can be formulated for oral administration in solid or liquid form, for parenteral intravenous, subcutaneous, intramuscular, intraperitoneal, intra-arterial, or intradermal injection, for or for vaginal, nasal, topical, or rectal administration.

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Suspensions, in addition to the active compounds, may contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of materials which can be useful for delaying release of the active agent can include polymeric substances and waxes.

Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds of the invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants, which can be required. Opthalmic formulations, eye ointments, powders and solutions are contemplated as being within the scope of this invention. Aqueous liquid compositions comprising compounds of the invention also are contemplated.

The compounds of the invention can be used in the form of pharmaceutically acceptable salts, esters, or amides derived from inorganic or organic acids. The term "pharmaceutically acceptable salts, esters and amides", as used herein, refer to carboxylate salts, amino acid addition salts, zwitterions, esters and amides of compounds of formulae (I)-(XI) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds of the invention or separately by reacting a free base function with a suitable organic acid.

Representative acids suitable for formation of addition salts by combination with the compounds of the invention include, but are not limited to, ascorbic acid, (D)-tartaric acid, (L)-tartaric acid, maleic acid, phosphoric acid, citric acid, hydrochloric acid, sulfuric acid and trifluoroacetic acid. Other acids include acetic, adipic, aspartic, glutamic, benzoic, benzenesulfonic, 4-methylbenzenesulfonic, camphorsulfonic, proprionic, hydrobromic, glucuronic, methanesulfonic, ethanesulfonic, naphthylene sulfonic, lactic, fumaric, oxalic, and succinic acid.

Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylamine, dimethylamine, trimethylamine, triethylamine, diethylamine, ethylamine and the such as. Other representative organic amines useful for the formation of base addition salts include ethylenediamine, ethanolamine, diethanolamine, piperidine, and piperazine.

The term "pharmaceutically acceptable ester", as used herein, refers to esters of compounds of the invention which hydrolyze in vivo and include those that break down readily in the human body to leave the parent compound or a salt thereof. Examples of pharmaceutically acceptable, non-toxic esters of the invention include $C_1$-to-$C_6$ alkyl esters and $C_5$-to-$C_7$ cycloalkyl esters, although $C_1$-to-$C_4$ alkyl esters are preferred. Esters of the compounds of formula (I) may be prepared according to conventional methods. For example, such esters may be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, alkyl triflate, for example with methyliodide, benzyl iodide, cyclopentyl iodide. They also may be prepared by reaction of the compound with an acid such as hydrochloric acid and an alcohol such as ethanol or methanol.

The term "pharmaceutically acceptable amide", as used herein, refers to non-toxic amides of the invention derived from ammonia, primary $C_1$-to-$C_6$ alkyl amines and secondary $C_1$-to-$C_6$ dialkyl amines. In the case of secondary amines, the amine may also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formulae (I)-(XI) may be prepared according to conventional methods. Pharmaceutically acceptable amides are prepared from compounds containing primary or secondary amine groups by reaction of the compound that contains the amino group with an alkyl anhydride, aryl anhydride, acyl halide, or aryl acid chloride. In the case of compounds containing carboxylic acid groups, the pharmaceutically acceptable esters are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, piperidine. They also may be prepared by reaction of the compound with an acid such as sulfuric acid and an alkylcarboxylic acid such as acetic acid, or with acid and an arylcarboxylic acid such as benzoic acid under dehydrating conditions as with molecular sieves added. The composition can contain a compound of the invention in the form of a pharmaceutically acceptable prodrug.

A prodrug of a suitable histamine $H_4$ receptor ligand also may be incorporated into a desired composition. The term "prodrug" or "pharmaceutically acceptable prodrug", as used herein, represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention may be rapidly transformed in vivo to a parent compound of formula (I), for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987), hereby incorporated by reference.

The invention contemplates pharmaceutically active compounds either chemically synthesized or formed by in vivo biotransformation to a suitable histamine $H_4$ receptor ligand.

Methods of the Invention

Histamine $H_4$ receptor ligands modulate the activity of histamine $H_4$ receptors, particularly by histamine $H_4$ receptor antagonism, agonism, partial agonism, or inverse agonism. In particular, the compounds and compositions of the invention can be used for treating and preventing pain disorders modulated by histamine $H_4$ receptor. Typically, such disorders can be ameliorated by modulating histamine $H_4$ receptors in a mammal, preferably by administering a compound or composition of the invention, either alone or in combination with another active agent, for example, as part of a therapeutic regimen.

The pharmaceutical compositions of this invention can be administered to humans and other mammals oral administration, by injection, including by intravenous, subcutaneous, intramuscular, intraperitoneal, intra-arterial, and intradermal injection. The pharmaceutical compositions of this invention can be administered to humans and other mammals topically (as by powders, lotions, ointments or drops applied to the skin), bucally, or inhaled, as an oral or nasal spray. The pharmaceutical compositions of this invention can be administered to humans and other mammals intrarectally, intravaginally. The term "parenterally," as used herein, refers to modes of administration which include intravenous, intramuscular, intraperitoneal, intrasternal, subcutaneous and intraarticular.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the invention can be employed in pure form or, where such forms exist, in pharmaceutically acceptable salt, ester, amide or prodrug form. Alternatively, the compound can be administered as a pharmaceutical composition containing the compound of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

Administering the histamine $H_4$ receptor ligand, or composition comprising the ligand, provides a method of treating a condition or disorder of pain. Examples of such pain conditions and disorders include, but are not limited to, inflammatory pain, hyperalgesia, inflammatory hyperalgesia, migraine, cancer pain, osteoarthritis pain, post-surgical pain, non-inflammatory pain, neuropathic pain, sub-categories of neuropathic pain including peripheral neuropathic pain syndromes, chemotherapy-induced neuropathy, complex regional pain syndrome, HIV sensory neuropathy, neuropathy secondary to tumor infiltration, painful diabetic neuropathy, phantom limb pain, postherpetic neuralgia, postmastectomy pain, trigeminal neuralgia, central neuropathic pain syndromes, central poststroke pain, multiple sclerosis pain, Parkinson disease pain, and spinal cord injury pain. More particularly, the method is useful for treating inflammatory pain, osteoarthritis pain, post surgical pain, and neuropathic pain.

The method more particularly is useful for treating or preventing conditions and disorders related to neuropathic pain. Neuropathic pain comprises various sub-types of neuropathic pain including, but not limited to, for example, peripheral neuropathic pain syndromes, chemotherapy-induced neuropathy, complex regional pain syndrome, HIV sensory neuropathy, neuropathy secondary to tumor infiltration, painful diabetic neuropathy, phantom limb pain, postherpetic neuralgia, postmastectomy pain, trigeminal neuralgia, central neuropathic pain syndromes, central poststroke pain, multiple sclerosis pain, Parkinson disease pain, and spinal cord injury pain.

Histamine $H_4$ receptor ligands and compositions comprising the same can be administered in accordance with a method of the invention, typically as part of a therapeutic regimen for treatment or prevention of conditions and disorders related to pain and modulated by histamine $H_4$ receptor activity. This aspect of the invention relates to the treatment of pain by the method of the use of the histamine $H_4$ ligands in combination with one or more therapeutic agents selected from histamine $H_3$ antagonists (such as ABT-239), NSAIDS (such as ibuprofen) including, COX-2 inhibitors (such as celecoxib), anti-nociceptive opiate agonists (such as morphine), anti-nociceptive alpha adrenergic agonists (such as dexmedetomidine), TRPV1 antagonists, nicotinic agonists such as nicotinic agonists such as ABT-418 or (1S,5S)-3-(5,6-dichloro-3-pyridinyl)-3,6-diazobicyclo[3.2.0]heptane, CB-1 agonists, CB-2 agonists, P2X7 antagonists, metabotropic glutamate receptor antagonists, anticonvulsants such as gabapentin or pregabilin, and tricyclic antidepressants such as amitriptyline.

For treatment or prevention of disease, the total daily dose of the compounds of this invention administered to a human or lower animal may range from about 5 to about 500 micromoles/kg of body weight. For purposes of oral administration, more preferable doses can be in the range of from about 30 to about 500 micromoles/kg body weight. If desired, the effective daily dose can be divided into multiple doses for purposes of administration; consequently, single dose compositions may contain such amounts or submultiples thereof to make up the daily dose. Particularly preferred compounds for the method include, but are not limited to, 4-[2-amino-6-(4-methyl-piperazin-1-yl)-pyrimidin-4-yl]-benzonitrile; 4-(4-methyl-piperazin-1-yl)-6-pyridin-3-yl-pyrimidin-2-ylamine; 5-chloro-1H-indol-2-yl)-(4-methyl-piperazin-1-yl)-methanone; 4-((R)-3-amino-pyrrolidin-1-yl)-6,7-dihydro-5H-benzo[6,7]cyclohepta[1,2-d]pyrimidin-2-ylamine; 4-piperazin-1-yl-6,7-dihydro-5H-benzo[6,7]cyclohepta[1,2-d]pyrimidin-2-ylamine; and 4-(3-methylamino-azetidin-1-yl)-6,7-dihydro-5H-benzo[6,7]cyclohepta[1,2-d]pyrimidin-2-ylamine; 4-tert-Butyl-6-(4-methyl-piperazin-1-yl)-pyrimidin-2-ylamine; 4-tert-Butyl-6-[4-(2-dimethylamino-ethyl)-piperazin-1-yl]-pyrimidin-2-ylamine; 4-tert-Butyl-6-[4-(3-dimethylamino-propyl)-piperazin-1-yl]-pyrimidin-2-ylamine; 4-Chloro-6-(4-methyl-piperazin-1-yl)-pyrimidin-2-ylamine; 6-tert-Butyl-N4-(2-dimethylamino-ethyl)-pyrimidine-2,4-diamine; 6-tert-Butyl-N4-(2-dimethylamino-ethyl)-N4-methyl-pyrimidine-2,4-diamine; 6-tert-Butyl-N4-(3-dimethylamino-propyl)-N4-methyl-pyrimidine-2,4-diamine; 4-tert-Butyl-6-(4-methyl-piperidin-1-yl)-pyrimidin-2-ylamine; 4-tert-Butyl-6-(4-ethyl-piperazin-1-yl)-pyrimidin-2-ylamine; 4-Methyl-6-(4-methyl-piperazin-1-yl)-pyrimidin-2-ylamine; 4-Methoxy-6-(4-methyl-piperazin-1-yl)-pyrimidin-2-ylamine; 6-(4-Methyl-piperazin-1-yl)-pyrimidine-2,4-diamine; 4,6-Bis-(4-methyl-piperazin-1-yl)-pyrimidin-2-ylamine; 4-tert-Butyl-6-(2-dimethylamino-ethoxy)-pyrimidin-2-ylamine; 4-Adamantan-1-yl-6-(4-methyl-piperazin-1-yl)-pyrimidin-2-ylamine; 4-(4-Methyl-piperazin-1-yl)-6-phenyl-pyrimidin-2-ylamine; 4-(4-Methyl-piperazin-1-yl)-pyrimidin-2-ylamine; 4-(4-Methyl-piperazin-1-yl)-6-p-tolyl-pyrimidin-2-ylamine; 4-(4-Methyl-piperazin-1-yl)-6-m-tolyl-pyrimidin-2-ylamine; 4-(4-Methyl-piperazin-1-yl)-6-o-tolyl-pyrimidin-2-ylamine; 4-(4-Methoxy-phenyl)-6-(4-methyl-piperazin-1-yl)-pyrimidin-2-ylamine; 4-(3-Methoxy-phenyl)-6-(4-methyl-piperazin-1-yl)-pyrimidin-2-ylamine; 4-(2-Methoxy-phenyl)-6-(4-methyl-piperazin-1-yl)-pyrimidin-2-ylamine; 4-(4-Chloro-phenyl)-6-(4-methyl-piperazin-1-yl)-pyrimidin-2-ylamine; 4-(3-Chloro-phenyl)-6-(4-methyl-piperazin-1-yl)-pyrimidin-2-ylamine; 4-Biphenyl-4-yl-6-(4-methyl-piperazin-1-yl)-pyrimidin-2-ylamine; 4-(4-Methyl-piperazin-1-yl)-6-naphthalen-2-yl-pyrimidin-2-ylamine; 4-(4-Methyl-piperazin-1-yl)-6-naphthalen-1-yl-pyrimidin-2-ylamine; 4-(4-Methyl-piperazin-1-yl)-6-pyridin-4-yl-pyrimidin-2-ylamine; 4-Biphenyl-3-yl-6-(4-methyl-piperazin-1-yl)-pyrimidin-2-ylamine; 4-Biphenyl-2-yl-6-(4-methyl-piperazin-1-yl)-pyrimidin-2-ylamine; 4-tert-Butyl-6-(1-methyl-1,2,3,6-tetrahydro-pyridin-4-yl)-pyrimidin-2-ylamine; 4-tert-Butyl-6-(1-methyl-piperidin-4-yl)-pyrimidin-2-ylamine; 4-tert-Butyl-6-(1,2,3,6-tetrahydro-pyridin-4-yl)-pyrimidin-2-ylamine; 2'-Methoxy-6-(4-methyl-piperazin-1-yl)-[4,5']bipyrimidinyl-2-ylamine; 5-[2-Amino-6-(4-methyl-piperazin-1-yl)-pyrimidin-4-yl]-[1-methyl-1H-pyridin-2-one; 4-(6-Methoxy-pyridin-3-yl)-6-(4-methyl-piperazin-1-yl)-pyrimidin-2-ylamine; 6-(4-Methyl-piperazin-1-yl)-[4,5']bipyrimidinyl-2-ylamine; 4-(6-

Fluoro-pyridin-3-yl)-6-(4-methyl-piperazin-1-yl)-pyrimidin-2-ylamine; 4-(4-Methyl-piperazin-1-yl)-6-(1-methyl-1H-pyrazol-4-yl)-pyrimidin-2-ylamine; 4-(2,6-Difluoro-pyridin-3-yl)-6-(4-methyl-piperazin-1-yl)-pyrimidin-2-ylamine; 5-[2-Amino-6-(4-methyl-piperazin-1-yl)-pyrimidin-4-yl]-nicotinonitrile; 4-(2,6-Dimethoxy-phenyl)-6-(4-methyl-piperazin-1-yl)-pyrimidin-2-ylamine; 4-(4-Methoxy-pyridin-3-yl)-6-(4-methyl-piperazin-1-yl)-pyrimidin-2-ylamine; 4-(4-Methyl-piperazin-1-yl)-6-pyrrolidin-1-yl-pyrimidin-2-ylamine; 4-Iodo-6-(4-methyl-piperazin-1-yl)-pyrimidin-2-ylamine; 4-(4-Methyl-piperazin-1-yl)-6-(4-phenyl-imidazol-1-yl)-pyrimidin-2-ylamine; 1-[2-Amino-6-(4-methyl-piperazin-1-yl)-pyrimidin-4-yl]-imidazolidin-2-one; 4-(1-Methyl-1,2,3,6-tetrahydro-pyridin-4-yl)-6-pyrrolidin-1-yl-pyrimidin-2-ylamine; 4-(1-Methyl-piperidin-4-yl)-6-pyrrolidin-1-yl-pyrimidin-2-ylamine; 4-(2,7-Diaza-spiro[3.5]non-7-yl)-pyrimidin-2-ylamine; 5-Methyl-4-(4-methyl-piperazin-1-yl)-pyrimidin-2-ylamine; 4-[2-Amino-5-methyl-6-(4-methyl-piperazin-1-yl)-pyrimidin-4-yl]-benzonitrile; 5-Methoxy-4-(4-methyl-piperazin-1-yl)-pyrimidin-2-ylamine; 4-(4-Methyl-piperazin-1-yl)-5-phenyl-pyrimidin-2-ylamine; 4-[2-Amino-5-methoxy-6-(4-methyl-piperazin-1-yl)-pyrimidin-4-yl]-benzonitrile; 4-[2-Amino-6-(4-methyl-piperazin-1-yl)-5-phenyl-pyrimidin-4-yl]-benzonitrile; 4-(4-Methyl-piperazin-1-yl)-6-(2-methylsulfanyl-phenyl)-pyrimidin-2-ylamine; 4-(4-Methyl-piperazin-1-yl)-6-(4-methylsulfanyl-phenyl)-pyrimidin-2-ylamine; 3-[2-Amino-6-(4-methyl-piperazin-1-yl)-pyrimidin-4-yl]-1,5,5-trimethyl-imidazolidine-2,4-dione; 1-[2-Amino-6-(4-methyl-piperazin-1-yl)-pyrimidin-4-yl]-3-methyl-imidazolidin-2-one; 1-[2-Amino-6-(4-methyl-piperazin-1-yl)-pyrimidin-4-yl]-3-methyl-1,3-dihydro-benzoimidazol-2-one; 1-[2-Amino-6-(4-methyl-piperazin-1-yl)-pyrimidin-4-yl]-1,3-dihydro-benzoimidazol-2-one; 6-(4-Methyl-piperazin-1-yl)-N4-phenyl-pyrimidine-2,4-diamine; N4-Methyl-6-(4-methyl-piperazin-1-yl)-N4-phenyl-pyrimidine-2,4-diamine; 4-(4-Methyl-piperazin-1-yl)-6-morpholin-4-yl-pyrimidin-2-ylamine; 4-(4-Methyl-piperazin-1-yl)-6-piperidin-1-yl-pyrimidin-2-ylamine; 4-(3-Dimethylamino-pyrrolidin-1-yl)-6-(4-methyl-piperazin-1-yl)-pyrimidin-2-ylamine; 4-(4-Methyl-piperazin-1-yl)-6-piperazin-1-yl-pyrimidin-2-ylamine; {(S)-1-[2-Amino-6-(4-methyl-piperazin-1-yl)-pyrimidin-4-yl]-pyrrolidin-2-yl}-methanol; 1-[2-Amino-6-(4-methyl-piperazin-1-yl)-pyrimidin-4-yl]-pyrrolidin-3-ol; 4-(4-Methyl-piperazin-1-yl)-6-(2-methyl-pyrrolidin-1-yl)-pyrimidin-2-ylamine; N4-Methyl-6-(4-methyl-piperazin-1-yl)-pyrimidine-2,4-diamine; N4,N4-Diethyl-6-(4-methyl-piperazin-1-yl)-pyrimidine-2,4-diamine; N4, N4-Dimethyl-6-(4-methyl-piperazin-1-yl)-pyrimidine-2,4-diamine; N4-Benzyl-N4-methyl-6-(4-methyl-piperazin-1-yl)-pyrimidine-2,4-diamine; 4-[2-Amino-6-(4-methyl-piperazin-1-yl)-pyrimidin-4-yl]-imidazole-1-sulfonic acid dimethylamide; 3-[2-Amino-6-(4-methyl-piperazin-1-yl)-pyrimidin-4-yl]-benzonitrile; 2-[2-Amino-6-(4-methyl-piperazin-1-yl)-pyrimidin-4-yl]-benzonitrile; 4-(4-Methyl-piperazin-1-yl)-6-(1H-pyrazol-4-yl)-pyrimidin-2-ylamine; 4-(1H-Imidazol-4-yl)-6-(4-methyl-piperazin-1-yl)-pyrimidin-2-ylamine; 4-(1-Methyl-1H-imidazol-4-yl)-6-(4-methyl-piperazin-1-yl)-pyrimidin-2-ylamine; 4-[2-Amino-6-((3aR,6aS)-5-methyl-hexahydro-pyrrolo[3,4-c]pyrrol-2-yl)-pyrimidin-4-yl]-benzonitrile; 4-piperazin-1-yl-6-pyridin-3-yl-pyrimidin-2-ylamine; 4-(2-Amino-6-piperazin-1-yl-pyrimidin-4-yl)-benzonitrile; 2-[2-Amino-6-(4-methyl-piperazin-1-yl)-pyrimidin-4-yl]-phenol; 4-[2-Amino-6-(4-cyclopropylmethyl-piperazin-1-yl)-pyrimidin-4-yl]-benzonitrile; [(S)-1-(2-Amino-6-piperazin-1-yl-pyrimidin-4-yl)-pyrrolidin-2-yl]-methanol; 4-(6-Methoxy-pyridin-3-yl)-6-piperazin-1-yl-pyrimidin-2-ylamine; 4-(3-Iodo-phenyl)-6-(4-methyl-piperazin-1-yl)-pyrimidin-2-ylamine; 4-(4-Iodo-phenyl)-6-(4-methyl-piperazin-1-yl)-pyrimidin-2-ylamine; 4-tert-Butyl-2-methoxy-6-(4-methyl-piperazin-1-yl)-pyrimidine; 4-tert-Butyl-6-piperidin-4-yl-pyrimidin-2-ylamine; 4-(2,6-Dimethyl-pyridin-3-yl)-6-(4-methyl-piperazin-1-yl)-pyrimidin-2-ylamine; 4-(3,5-Dimethyl-1H-pyrazol-4-yl)-6-(4-methyl-piperazin-1-yl)-pyrimidin-2-ylamine; 4-(4-Methyl-piperazin-1-yl)-6-(1,3,5-trimethyl-1H-pyrazol-4-yl)-pyrimidin-2-ylamine; 4-(2-Methoxy-pyridin-3-yl)-6-(4-methyl-piperazin-1-yl)-pyrimidin-2-ylamine; 4-Imidazol-1-yl-6-(4-methyl-piperazin-1-yl)-pyrimidin-2-ylamine; N4-Azetidin-3-yl-pyrimidine-2,4-diamine; 1-[2-Amino-6-(4-methyl-piperazin-1-yl)-pyrimidin-4-yl]-1H-pyridin-2-one; 4-(4-Chloro-imidazol-1-yl)-6-(4-methyl-piperazin-1-yl)-pyrimidin-2-ylamine; {1-[2-Amino-6-(4-methyl-piperazin-1-yl)-pyrimidin-4-yl]-1H-imidazol-4-yl}-methanol; 4-Chloro-6-(4-methyl-piperazin-1-yl)-pyrimidine-2,5-diamine; 4-Chloro-5-methyl-6-(4-methyl-piperazin-1-yl)-pyrimidin-2-ylamine; 4-(4-Methyl-piperazin-1-yl)-pyrimidine-2,5-diamine; 4-Benzoimidazol-1-yl-6-(4-methyl-piperazin-1-yl)-pyrimidin-2-ylamine; 2-[2-Amino-6-(4-methyl-piperazin-1-yl)-pyrimidin-4-yl]-2H-pyridazin-3-one; N4-Benzyl-6-(4-methyl-piperazin-1-yl)-pyrimidine-2,4-diamine; and 4-piperazin-1-yl-pyrimidin-2-ylamine.

More particularly preferred compounds include, but are not limited to, 4-[2-amino-6-(4-methyl-piperazin-1-yl)-pyrimidin-4-yl]-benzonitrile; 4-(4-Methyl-piperazin-1-yl)-6-pyridin-3-yl-pyrimidin-2-ylamine; 5-chloro-1H-indol-2-yl)-(4-methyl-piperazin-1-yl)-methanone; 4-((R)-3-amino-pyrrolidin-1-yl)-6,7-dihydro-5H-benzo[6,7]cyclohepta[1,2-d]pyrimidin-2-ylamine; 4-piperazin-1-yl-6,7-dihydro-5H-benzo[6,7]cyclohepta[1,2-d]pyrimidin-2-ylamine; and 4-(3-methylamino-azetidin-1-yl)-6,7-dihydro-5H-benzo[6,7]cyclohepta[1,2-d]pyrimidin-2-ylamine.

Methods for Preparing Assayed Compounds

Compounds within the scope of suitable histamine $H_4$ receptor ligands as described above were prepared and assayed to evaluate the activity of such compounds. The preparation of these compounds can be better understood in connection with the previous synthetic Schemes and Examples which illustrate a means by which the compounds can be prepared.

Abbreviations which have been used in the descriptions of the schemes and the examples that follow are: Boc for butyloxycarbonyl; DMF for N,N-dimethylformamide; EtOAc for ethyl acetate; EtOH for ethanol; MeOH for methanol; MeI for iodomethane; MCPBA for 3-chloroperoxybenzoic acid; Ms for methanesulfonyl; Pd for palladium; tBu for tert-butyl; TEA for triethylamine; Tf for trifluoromethanesulfonyl; TFA for trifluoroacetic acid; THF for tetrahydrofuran; Ts for para-

EXAMPLES

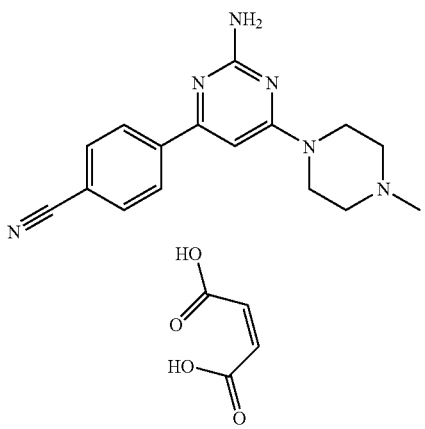

Example 1

4-(2-Amino-6-(4-methylpiperazin-1-yl)pyrimidin-4-yl)benzonitrile, maleate

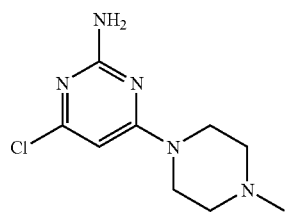

Example 1A

4-Chloro-6-(4-methylpiperazin-1-yl)pyrimidin-2-amine

2-Amino-4,6-dichloropyrimidine (15 g, 91 mmol) was treated with 1-methylpiperazine (10.1 g, 100 mmol), treated with Et$_3$N (90 mL, 0.64 mol), treated with EtOH (185 mL), heated to 80° C. over night, cooled, concentrated and partitioned between CH$_2$Cl$_2$ (100 mL) and 1 M NaOH (125 mL). The layers were separated and the aqueous layer was extracted with CH$_2$Cl$_2$ (4×100 mL). The combined CH$_2$Cl$_2$ layers were dried (MgSO$_4$), filtered, concentrated and crystallized from EtOAc to provide 14.9 g (71%) of the title compound. $^1$H NMR (CDCl$_3$) δ 2.34 (s, 3H), 2.45 (m, 4H), 3.60 (m, 4H), 4.82 (s, 2H), 5.96 (s, 1H); MS (DCl—NH$_3$) m/z 228 (M+H)$^+$ Example 1B 4-(2-Amino-6-(4-methylpiperazin-1-yl)pyrimidin-4-yl)benzonitrile maleate Example 1A (11.2 g, 49 mmol) was treated with 4-cyanophenylboronic acid (10.8 g, 74 mmol), treated with 1,2-dimethoxyethane (150 mL), treated with 2 M Na$_2$CO$_3$ (54 mL, 108 mmol) and the atmosphere of the reaction was purged with nitrogen. The mixture was treated with tetrakis (triphenylphosphine)palladium(0) (4.5 g, 3.9 mmol), heated to 90° C. over night under nitrogen, cooled to ambient temperature, treated with 1 M NaOH (125 mL) and extracted with CH$_2$Cl$_2$ (250 mL and then 3×100 mL). The combined CH$_2$Cl$_2$ layers were dried (MgSO$_4$), filtered, concentrated and chromatographed on silica gel eluting with a gradient of 2 and 3.5% (9:1 MeOH:saturated aqueous NH$_4$OH) in CH$_2$Cl$_2$ to provide 12.7 g (88%) of the title compound as a free base. This free base (12.7 g, 43 mmol) was suspended in acetone (100 mL), treated with a solution of maleic acid (5.0 g, 43 mmol) in acetone and the salt started to fall out of solution. This mixture was heated to reflux for 10 minutes with mixing and allowed to stand at ambient temperature over night. The solid was collected by filtration, washed with acetone and dried over night under vacuum to provide 15.6 g of the title compound.

$^1$H NMR (DMSO-d6) δ 2.79 (s, 3H) 3.20 (bs, 4H) 3.31 (bs, 4H) 6.04 (s, 2H) 6.39 (s, 2H) 6.83 (s, 1H) 7.95 (d, J=8.48 Hz, 2H) 8.24 (d, J=8.82 Hz, 2H);
MS (DCl—NH$_3$) m/z 258 (M+H)$^+$
mp 187-190° C. (dec.)

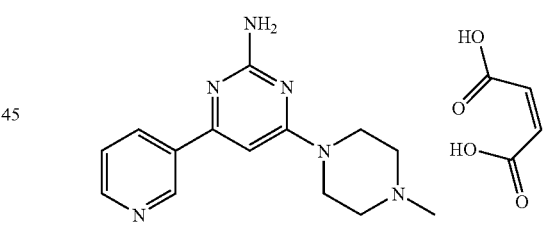

Example 2

4-(4-Methylpiperazin-1-yl)-6-(pyridin-3-yl)pyrimidin-2-amine, maleate

The title compound was prepared using the procedure outlined in Example 1B substituting 3-pyridineboronic acid for 4-cyanophenylboronic acid.

$^1$H NMR (DMSO-d6) δ 2.78 (s, 3H), 3.19 (bs, 4H), 3.32 (bs, 4H), 6.04 (s, 2H), 6.38 (s, 2H), 6.81 (s, 1H), 7.50 (ddd, J=7.88, 4.83, 0.85 Hz, 1H), 8.37 (dt, J=8.14, 2.03 Hz, 1H), 8.65 (dd, J=4.75, 1.70 Hz, 1H), 9.22 (dd, J=2.37, 0.68 Hz, 1H);
MS (DCl—NH$_3$) m/z 271 (M+H)$^+$
mp 175-178° C. (dec.)

Example 3

5-Chloro-1H-indol-2-yl)-(4-methyl-piperazin-1-yl)-methanone

5-Chloro-1H-indol-2-yl)-(4-methyl-piperazin-1-yl)-methanone is a compound of generic structure (II) with reported histamine $H_4$ receptor antagonist activity (see Jablonowski, et al., Journal of Medicinal Chemistry (2003) v. 46, pp. 3957-3960, and Thurmond, et al. Journal of Pharmacology and Experimental Therapeutics (2004), vol. 309, pp. 404-413. This compound, also known as JNJ-7777120, is commercially available from Sigma as catalog F J3770, Chemical Abstracts number 459168-41-3.

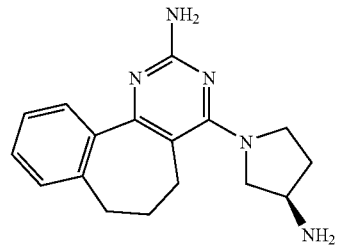

Example 4

4-((3R)-3-Amino-pyrrolidin-1-yl)-6,7-dihydro-5H-benzo[6,7]cyclohepta[1,2-d]pyrimidin-2-ylamine

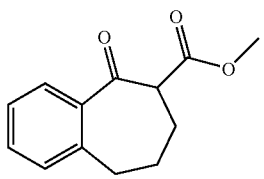

Example 4A

Methyl 5-oxo-6,7,8,9-tetrahydro-5H-benzo[7]annulene-6-carboxylate

A solution of dimethyl carbonate (20 mL) was treated with NaH (3 g, 60% dispersed in oil, 75 mmol) and heated to 85° C. To the mixture was dropwise added a solution of bezosuberone (3 g, 18.75 mmol) in dimethyl carbonate (10 mL). The resulting mixture was refluxed for 3 hours, cooled to 0° C., quenched with HCl (1N) (100 mL) and extracted with ether. The organic layer was washed with NaHCO₃ and brine, dried (MgSO₄) and concentrated to provide the title compound as a brownish oil.

$^1$H NMR (CDCl₃) δ 2.06-2.13 (m, 4H), 2.64 (t, J=6 Hz, 2H), 3.83 (s, 3H), 7.20-7.23 (m, 1H), 7.32-7.35 (m, 2H), 7.61-7.64 (m, 1H), 12.6 (s, 1H);

MS (M+H)$^+$ m/z 219

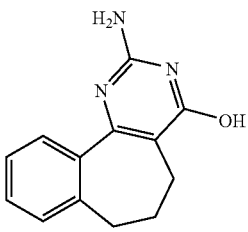

Example 4B

2-Amino-6,7-dihydro-5H-benzo[6,7]cyclohepta[1,2-d]pyrimidin-4-ol

A solution of the product from Example 4A (4.2 g, est. 18 mmol), guanidine chloride (7.1 g, 72.8 mmol), and K₂CO₃ (10.8 g, 78 mmol) in DMF (30 mL) was heated to 125° C. for 3 hours. The mixture was cooled and the solids were removed by filtration. The solids were washed with EtOAc. The combined filtrates were concentrated under reduced pressure and the residue was passed through silica gel pad eluting with EtOAc:hexanes (8:2) and then with MeOH:EtOAc:CH₂Cl₂ (10:45:45) to provide the title compound as a white solid (2.8 g).

$^1$H NMR (CD₃OD) δ 2.08-2.17 (m, 2H), 2.27 (t, J=6 Hz, 2H), 2.59 (t, J=6 Hz, 2H), 7.25-7.28 (m, 1H), 7.33-7.36 (m, 2H), 7.56-7.59 (m, 1H).

MS (M+H)$^+$ m/z 228.

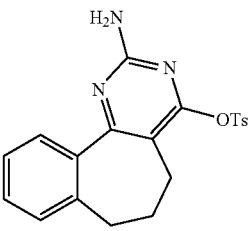

Example 4C

2-Amino-6,7-dihydro-5H-benzo[6,7]cyclohepta[1,2-d]pyrimidin-4-yl 4-methylbenzenesulfonate The product from Example 4B (2.8 g, 12.3 mmol) was suspended in CH₂Cl₂ (100 mL), treated with TsCl (4.7 g, 24.6 mmol), 4-dimethylaminopyridine (46 mg, 1.2 mmol), and triethylamine (4.3 mL. 31 mmol). The mixture was stirred at room temperature for 16 hours, diluted with CH₂Cl₂, washed with H₂O, dried (MgSO₄), concentrated and chromatographed on silica gel eluting with EtOAc:Hexanes:CH₂Cl₂ (15:45:45) to provide the title product (3 g) as a white solid.

$^1$H NMR (CD₃OD) δ 2.08 (p, J=6 Hz, 2H), 2.32 (t, J=6 Hz, 2H), 2.47 (s, 3H), 2.52 (t, J=6 Hz, 2H), 7.25-7.28 (m, 1H), 7.33-7.43 (m, 2H), 7.46 (d, J=9 Hz, 2H), 7.57-7.6 (m, 1H), 7.98 (d, J=9 Hz, 2H).

MS (M+H)$^+$ m/z 382.

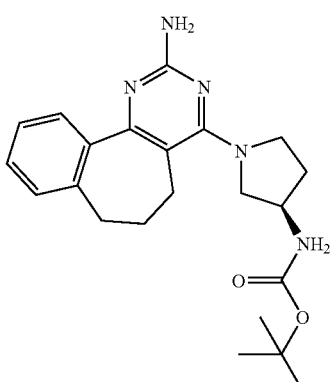

Example 4D

4-((3R)-3-(t-Butoxycarbonyl)Amino-pyrrolidin-1-yl)-6,7-dihydro-5H-benzo[6,7]cyclohepta[1,2-d]pyrimidin-2-ylamine A solution of the product from Example 4C (1.5 g, 3.93 mmol), (R)-tert-butyl pyrrolidin-3-ylcarbamate (CAS #: 122536-77-0) (1.1 g, 5.9 mmol) and triethylamine (0.9 mL, 5.9 mmol) in acetonitrile (35 mL) was heated to 80° C. for 16 hours. The mixture was cooled to room temperature, diluted with EtOAc, washed with H$_2$O and brine, dried (MgSO$_4$), concentrated and chromatographed on silica gel eluting with ethyl acetate to provide the title compound.

$^1$H NMR (CDCl$_3$) δ 1.46 (s, 9H), 1.85-1.96 (m, 1H), 2.27-2.41 (m, 2H), 2.64 (t, J=6 Hz, 2H), 3.46-3.51 (m, 1H), 3.62-3.78 (m, 2H), 3.84-3.9 (m, 1H), 4.27 (bs, 1H), 4.65 (bs, 2H), 7.19-7.22 (m, 1H), 7.3-7.38 (m, 2H), 7.74-7.77 (m, 1H).
MS (M+H)$^+$ m/z 396.

Example 4E

4-((R)-3-Amino-pyrrolidin-1-yl)-6,7-dihydro-5H-benzo[6,7]cyclohepta[1,2-d]pyrimidin-2-ylamine A solution of the product from Example 4D (68 mg, 0.17 mmol) in CH$_2$Cl$_2$ (3 mL) was treated with trifluoroacetic acid (0.2 mL) and stirred for 16 hours. The mixture was diluted with CH$_2$Cl$_2$, washed H$_2$O, dried, concentrated and chromatographed on silica gel eluting with eluting with NH$_4$OH/MeOH/CH$_2$Cl$_2$ (0.8/8/92) to provide the title compound.

$^1$H NMR (CD$_3$OD) δ 1.79 (m, 1H), 2.10-2.25 (m, 3H), 2.35 (t, J=6.95 Hz, 2H), 2.65 (t, J=6.78 Hz, 2H), 3.42 (dd, J=10.51, 5.42 Hz, 1H), 3.56 (m, 1H), 3.69 (m, 1H), 3.82 (m, 2H), 7.25 (m, 1H), 7.34 (m, 2H), 7.63 (m, 1H). MS (M+H)$^+$ m/z 296.

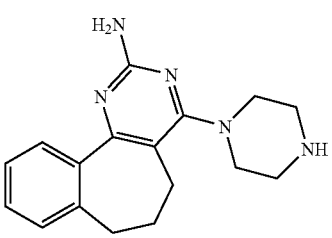

Example 5

4-piperazin-1-yl-6,7-dihydro-5H-benzo[6,7]cyclohepta[1,2-d]pyrimidin-2-ylamine The title compound was prepared using the procedures described in the Examples 4D and 4E substituting piperazine for (R)-tert-butyl pyrrolidin-3-ylcarbamate.

$^1$H NMR (CD$_3$OD) δ 2.17-2.35 (m, 4H), 2.65 (t, J=6.61 Hz, 2H), 2.94 (m, 4H), 3.39 (m, 4H), 7.26 (m, 1H), 7.35 (m, 2H), 7.62 (m, 1H)
MS (M+H)$^+$ m/z 296.

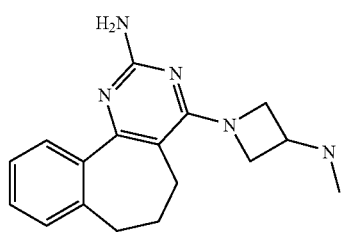

Example 6

4-(3-Methylamino-azetidin-1-yl)-6,7-dihydro-5H-benzo[6,7]cyclohepta[1,2-d]pyrimidin-2-ylamine The title compound was prepared using the procedures described in the Example 4D and 4E substituting tert-butyl azetidin-3-yl(methyl)carbamate (CAS #: 577777-20-9) for (R)-tert-butyl pyrrolidin-3-ylcarbamate.

$^1$H NMR (CD$_3$OD) δ 2.06-2.27 (m, 4H), 2.36 (s, 3H), 2.60 (t, J=6.78 Hz, 2H), 3.63 (m, 1H), 3.99 (dd, J=9.32, 4.92 Hz, 2H), 4.42 (dd, J=8.99, 7.63 Hz, 2H), 7.25 (m, 1H), 7.34 (m, 2H), 7.59 (m, 1H). MS (M+H)$^+$ m/z 296.

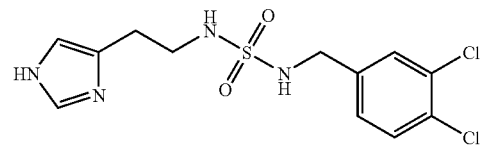

Example 7

Sulfamide, N-[(3,4-dichlorophenyl)methyl]-N'-[2-(1H-imidazol-4-yl)ethyl]-2-Chloroethanol (0.6 g, 7.4 mmol) was added dropwise solution of chlorosulfonyl isocyanate (1.05 g, 7.4 mmol; Chemical Abstracts number 1189-71-5) in CH$_2$Cl$_2$ at 0° C. The reaction mixture was stirred at room temperature for 3 hours, then 2-(1-trityl-1H-imidazol-4-yl)-ethylamine (2.9 g, 7.4 mmol) and triethylamine (4 mL) were added dropwise, keeping the reaction temperature below 5° C. The reaction mixture was stirred at room temperature overnight, then was quenched with 1-Normal aqueous HCl and extracted with CH$_2$Cl$_2$. The organic layer was dried over anhydrous MgSO$_4$, and concentrated to yield the crude title product that was used in the next step.

To a suspension of the product from the previous step (2.0 g, 4.0 mmol) and triethylamine (0.5 mL) in acetonitrile was added 3,4-dichlorobenzylamine (0.7 g, 4 mmol; Chemical abstracts number 102-49-8) and the reaction mixture was heated at reflux for 4 hours. The reaction mixture was concentrated and partitioned between water and dichloromethane. The organic layer was dried over $MgSO_4$ and purified by chromatography, eluting with gradient of 0-5% methane in dichloromethane. The tritylated product obtained (1.5 g) was dissolved in THF and treated with 2-Normal aqueous HCl, and heated at reflux for 3 hours. The reaction mixture was then concentrated and partitioned in $H_2O$/EtOAc. The organic layer was discarded, and the aqueous layer was then basified with NaOH solution and extracted with DCM containing 1% MeOH to yield the title product.

$^1$H NMR (DMSO-$D_6$) δ 2.65 (t, J=7.54 Hz, 2H), 3.03 (m, 2H), 3.99 (d, J=6.35 Hz, 2H), 6.80 (s, 1H), 7.05 (t, J=5.55 Hz, 1H), 7.32 (dd, J=8.33, 1.98 Hz, 1H), 7.49 (t, 1H), 7.52 (s, 1H) 7.57 (m, 2H). Mass spectrum MS (M+H) at m/z=349.

Additional compounds that are histamine $H_4$ receptor ligands are, for example:

4-tert-Butyl-6-(4-methyl-piperazin-1-yl)-pyrimidin-2-ylamine;
4-tert-Butyl-6-[4-(2-dimethylamino-ethyl)-piperazin-1-yl]-pyrimidin-2-ylamine;
6-tert-Butyl-$N^4$-(2-dimethylamino-ethyl)-pyrimidine-2,4-diamine;
4-tert-Butyl-6-(4-ethyl-piperazin-1-yl)-pyrimidin-2-ylamine;
4-Methyl-6-(4-methyl-piperazin-1-yl)-pyrimidin-2-ylamine
6-(4-Methyl-piperazin-1-yl)-pyrimidine-2,4-diamine;
4,6-Bis-(4-methyl-piperazin-1-yl)-pyrimidin-2-ylamine;
4-tert-Butyl-6-(2-dimethylamino-ethoxy)-pyrimidin-2-ylamine;
4-Adamantan-1-yl-6-(4-methyl-piperazin-1-yl)-pyrimidin-2-ylamine
4-(4-Methyl-piperazin-1-yl)-6-phenyl-pyrimidin-2-ylamine; 4-(4-Methyl-piperazin-1-yl)-pyrimidin-2-ylamine;
4-(4-Methyl-piperazin-1-yl)-6-p-tolyl-pyrimidin-2-ylamine;
4-(4-Methyl-piperazin-1-yl)-6-m-tolyl-pyrimidin-2-ylamine;
4-(4-Methyl-piperazin-1-yl)-6-o-tolyl-pyrimidin-2-ylamine;
4-(4-Methoxy-phenyl)-6-(4-methyl-piperazin-1-yl)-pyrimidin-2-ylamine;
4-(3-Methoxy-phenyl)-6-(4-methyl-piperazin-1-yl)-pyrimidin-2-ylamine;
4-(2-Methoxy-phenyl)-6-(4-methyl-piperazin-1-yl)-pyrimidin-2-ylamine;
4-(4-Chloro-phenyl)-6-(4-methyl-piperazin-1-yl)-pyrimidin-2-ylamine;
4-(3-Chloro-phenyl)-6-(4-methyl-piperazin-1-yl)-pyrimidin-2-ylamine;
4-Biphenyl-4-yl-6-(4-methyl-piperazin-1-yl)-pyrimidin-2-ylamine;
4-(4-Methyl-piperazin-1-yl)-6-naphthalen-2-yl-pyrimidin-2-ylamine;
4-(4-Methyl-piperazin-1-yl)-6-naphthalen-1-yl-pyrimidin-2-ylamine;
4-(4-Methyl-piperazin-1-yl)-6-pyridin-4-yl-pyrimidin-2-ylamine;
4-Biphenyl-3-yl-6-(4-methyl-piperazin-1-yl)-pyrimidin-2-ylamine;
4-Biphenyl-2-yl-6-(4-methyl-piperazin-1-yl)-pyrimidin-2-ylamine;
5-[2-Amino-6-(4-methyl-piperazin-1-yl)-pyrimidin-4-yl]-1-methyl-1H-pyridin-2-one;
4-(6-Methoxy-pyridin-3-yl)-6-(4-methyl-piperazin-1-yl)-pyrimidin-2-ylamine;
4-(6-Fluoro-pyridin-3-yl)-6-(4-methyl-piperazin-1-yl)-pyrimidin-2-ylamine;
4-(4-Methyl-piperazin-1-yl)-6-(1-methyl-1H-pyrazol-4-yl)-pyrimidin-2-ylamine; 4-(2,6-Difluoro-pyridin-3-yl)-6-(4-methyl-piperazin-1-yl)-pyrimidin-2-ylamine; 5-[2-Amino-6-(4-methyl-piperazin-1-yl)-pyrimidin-4-yl]-nicotinonitrile;
4-(2,6-Dimethoxy-phenyl)-6-(4-methyl-piperazin-1-yl)-pyrimidin-2-ylamine;
4-(4-Methoxy-pyridin-3-yl)-6-(4-methyl-piperazin-1-yl)-pyrimidin-2-ylamine;
4-(4-Methyl-piperazin-1-yl)-6-pyrrolidin-1-yl-pyrimidin-2-ylamine;
4-Iodo-6-(4-methyl-piperazin-1-yl)-pyrimidin-2-ylamine;
5-Methyl-4-(4-methyl-piperazin-1-yl)-pyrimidin-2-ylamine;
4-[2-Amino-5-methyl-6-(4-methyl-piperazin-1-yl)-pyrimidin-4-yl]-benzonitrile; 5-Methoxy-4-(4-methyl-piperazin-1-yl)-pyrimidin-2-ylamine;
4-[2-Amino-5-methoxy-6-(4-methyl-piperazin-1-yl)-pyrimidin-4-yl]-benzonitrile;
4-(4-Methyl-piperazin-1-yl)-6-(2-methylsulfanyl-phenyl)-pyrimidin-2-ylamine; 4-(4-Methyl-piperazin-1-yl)-6-(4-methylsulfanyl-phenyl)-pyrimidin-2-ylamine; 6-(4-Methyl-piperazin-1-yl)-$N^4$-phenyl-pyrimidine-2,4-diamine; $N^4$-Methyl-6-(4-methyl-piperazin-1-yl)-$N^4$-phenyl-pyrimidine-2,4-diamine;
4-(4-Methyl-piperazin-1-yl)-6-morpholin-4-yl-pyrimidin-2-ylamine;
4-(4-Methyl-piperazin-1-yl)-6-piperidin-1-yl-pyrimidin-2-ylamine;
{(S)-1-[2-Amino-6-(4-methyl-piperazin-1-yl)-pyrimidin-4-yl]-pyrrolidin-2-yl}-methanol;
1-[2-Amino-6-(4-methyl-piperazin-1-yl)-pyrimidin-4-yl]-pyrrolidin-3-ol;
4-(4-Methyl-piperazin-1-yl)-6-(2-methyl-pyrrolidin-1-yl)-pyrimidin-2-ylamine; $N^4$-Methyl-6-(4-methyl-piperazin-1-yl)-pyrimidine-2,4-diamine;
$N^4$,$N^4$-Diethyl-6-(4-methyl-piperazin-1-yl)-pyrimidine-2,4-diamine;
$N^4$, $N^4$-Dimethyl-6-(4-methyl-piperazin-1-yl)-pyrimidine-2,4-diamine;
$N^4$-Benzyl-$N^4$-methyl-6-(4-methyl-piperazin-1-yl)-pyrimidine-2,4-diamine;
4-[2-Amino-6-(4-methyl-piperazin-1-yl)-pyrimidin-4-yl]-imidazole-1-sulfonic acid dimethylamide;
3-[2-Amino-6-(4-methyl-piperazin-1-yl)-pyrimidin-4-yl]-benzonitrile;
2-[2-Amino-6-(4-methyl-piperazin-1-yl)-pyrimidin-4-yl]-benzonitrile;
4-(4-Methyl-piperazin-1-yl)-6-(1H-pyrazol-4-yl)-pyrimidin-2-ylamine;

4-(1H-Imidazol-4-yl)-6-(4-methyl-piperazin-1-yl)-pyrimidin-2-ylamine;

4-(1-Methyl-1H-imidazol-4-yl)-6-(4-methyl-piperazin-1-yl)-pyrimidin-2-ylamine;

4-piperazin-1-yl-6-pyridin-3-yl-pyrimidin-2-ylamine;

4-(2-Amino-6-piperazin-1-yl-pyrimidin-4-yl)-benzonitrile;

2-[2-Amino-6-(4-methyl-piperazin-1-yl)-pyrimidin-4-yl]-phenol;

[(S)-1-(2-Amino-6-piperazin-1-yl-pyrimidin-4-yl)-pyrrolidin-2-yl]-methanol;

4-(6-Methoxy-pyridin-3-yl)-6-piperazin-1-yl-pyrimidin-2-ylamine;

4-(3-Iodo-phenyl)-6-(4-methyl-piperazin-1-yl)-pyrimidin-2-ylamine;

4-(4-Iodo-phenyl)-6-(4-methyl-piperazin-1-yl)-pyrimidin-2-ylamine;

4-((R)-3-amino-pyrrolidin-1-yl)-6,7-dihydro-5H-benzo[6,7]cyclohepta[1,2-d]pyrimidin-2-ylamine;

4-piperazin-1-yl-6,7-dihydro-5H-benzo[6,7]cyclohepta[1,2-d]pyrimidin-2-ylamine; and 4-(3-methylamino-azetidin-1-yl)-6,7-dihydro-5H-benzo[6,7]cyclohepta[1,2-d]pyrimidin-2-ylamine.

Unless otherwise described, reactions were carried out under ambient conditions (ranging 17-27° C.), under nitrogen. Unless otherwise described, column chromatography means flash chromatography carried out using silica gel, a technique well known to those of ordinary skill in the art of organic synthesis.

Determination of Biological Activity

There are many methods available to show the effectiveness of compounds as histamine $H_4$ receptor ligands. Histamine $H_4$ receptors from mammalian species have been cloned. Methods to clone, express, and assess the potency and functional activity of such cloned genes are well known to those skilled in the art of molecular biology. Examples of methods of cloning and expressing histamine $H_4$ receptors, and of assessing the potency and functional activity are described in Nguyen, et al. Molecular Pharmacology (2001) vol. 59 pp. 427-433; Zhu, et al. Molecular Pharmacology (2001) vol. 59 pp. 434-441; Coge, et al., Biochemical and Biophysical Research Communications (2001) vol. 284, pp. 301-309; Liu, et al. Molecular Pharmacology (2001) vol. 59 pp. 420-426; Liu, et al. Journal of Pharmacology and Experimental Therapeutics (2001) v. 299, pp. 121-130; and Thurmond, et al. Journal of Pharmacology and Experimental Therapeutics (2004) v. 309, pp. 404-413. In the present case, to determine the potency and effectiveness of representative compounds of this invention as histamine-$H_4$ receptor ligands ($H_4$ receptor ligands), the following tests were conducted according to previously described methods (see Esbenshade, et al., Biochemical Pharmacology (2004), vol. 68, pp. 933-945, and in Krueger, et al., Journal of Pharmacology and Experimental Therapeutics (2005) v. 314, pp. 271-281): histamine $H_4$ receptors were cloned and stably expressed in HEK-293 (human embryonic kidney) cells coexpressing a G$\alpha$qi5. Before testing, cells are loaded with a Ca$^{+2}$ sensitive fluorescent dye, in this case Fluo-4. In the case of partial agonist or agonist ligands, addition of compound to the cells leads to the increase in intracellular Ca$^{+2}$ which is detected by FLIPR (Fluorescence Imaging Plate Reader; Molecular Devices, Sunnyvale, Calif.) technology. In a similar manner, compounds that are antagonists, inverse agonists, block the increase in fluorescence induced by the full histamine $H_4$ agonist histamine, and partial agonists reduce the amount of fluorescence induced by the full histamine $H_4$ agonist histamine. The fluorescence intensities measured before addition of the test compound are subtracted from the fluorescence intensities at later time points. Peak response values determined at each concentration of ligand are expressed as a percentage of the response obtained with the full agonist histamine. Concentration versus response data are analyzed to obtain compound potency as Kb values for antagonists and inverse agonists and as $EC_{50}$ values for partial agonists.

Histamine $H_4$ ligands of the invention block the ability of histamine to increase Ca$^{+2}$ concentrations in cells, and have potencies between 4 and 1000 nM.

The following table of representative histamine $H_4$ receptor ligands is provided, along with potency values:

| Compound Name (Example number) | Potency in the FLIPR assay (nM) |
|---|---|
| 4-(2-amino-6-(4-methylpiperazin-1-yl)pyrimidin-4-yl)benzonitrile, maleate (Example 1) | 58 |
| 4-(4-methylpiperazin-1-yl)-6-(pyridin-3-yl)pyrimidin-2-amine, maleate (Example 2) | 200 |
| 5-Chloro-1H-indol-2-yl)-(4-methyl-piperazin-1-yl)-methanone (Example 3) | 3 |
| 4-((3R)-3-Amino-pyrrolidin-1-yl)-6,7-dihydro-5H-benzo[6,7]cyclohepta[1,2-d]pyrimidin-2-ylamine (Example 4) | 10 |
| 4-Piperazin-1-yl-6,7-dihydro-5H-benzo[6,7]cyclohepta[1,2-d]pyrimidin-2-ylamine (Example 5) | 15 |
| 4-(3-Methylamino-azetidin-1-yl)-6,7-dihydro-5H-benzo[6,7]cyclohepta[1,2-d]pyrimidin-2-ylamine (Example 6) | 9 |
| Sulfamide, N-[(3,4-dichlorophenyl)methyl]-N'-[2-(1H-imidazol-4-yl)ethyl]- (Example 7) | 34 |

The potency of compounds of the invention in displacing $^3$H-histamine in competition binding assays is assessed by methods described in Esbenshade, et al., Biochemical Pharmacology (2004), vol. 68, pp. 933-945. In this assay, membranes were prepared from HEK-293 cells transiently transfected with the pCINeo expression vector harboring the histamine $H_4$ receptor by homogenization of the cells on ice in TE buffer (50 mM Tris-HCl buffer, pH 7.4, containing 5 mM EDTA), 1 mM benzamidine, 2 µg/ml aprotinin, 1 µg/ml leupeptin, and 1 µg/ml pepstatin. The homogenate was centrifuged at 40,000 g for 20 minutes at 4° C. This step was repeated, and the resulting pellet was resuspended in TE buffer. Aliquots were frozen at −70° C. until needed. On the day of assay, membranes were thawed and diluted with TE buffer. Competition radioligand binding assays were performed with increasing concentrations of test compound in the presence of [$^3$H]-histamine incubated at 25° C. for 1 h in a total volume of 0.5 ml of 50 mM Tris, 5 mM EDTA, pH 7.4. All binding reactions were terminated by filtration under vacuum onto polyethylenimine (0.3%) presoaked Unifilters (PerkinElmer Life Sciences) or Whatman GF/B filters (Whatman, Clifton, N.J.) followed by three brief washes with 4 ml of ice-cold TE buffer. Bound radiolabel was determined by liquid scintillation counting. For all of the radioligand competition binding assays, $IC_{50}$ values and Hill slopes were determined by Hill transformation of the data and $K_i$ values were determined by the Cheng-Prusoff equation.

Histamine $H_4$ ligands of the invention displace $^3$H-histamine, with potencies in competition binding assays with potencies between 0.002 and 6 micromolar.

Generally, representative compounds of the invention demonstrated potencies in the above FLIPR assay from about 4 nM to about 38000 nM. Preferred compounds of the invention have potencies at histamine-$H_4$ receptors from about 4 nM to about 200 nM. More preferred compounds of the invention have potencies at histamine $H_4$ receptors from about 4 nM to about 40 nM.

The following table of representative histamine $H_4$ receptor ligands is provided, along with potency values:

| Compound Name (Example number) | Potency in Competition Binding Assay (nM) |
|---|---|
| 4-(2-amino-6-(4-methylpiperazin-1-yl)pyrimidin-4-yl)benzonitrile, maleate (Example 1) | 35 |
| 4-(4-methylpiperazin-1-yl)-6-(pyridin-3-yl)pyrimidin-2-amine,maleate (Example 2) | 178 |
| 5-Chloro-1H-indol-2-yl)-(4-methyl-piperazin-1-yl)-methanone (Example 3) | 12 |
| 4-((3R)-3-Amino-pyrrolidin-1-yl)-6,7-dihydro-5H-benzo[6,7]cyclohepta[1,2-d]pyrimidin-2-ylamine (Example 4) | 5 |
| 4-Piperazin-1-yl-6,7-dihydro-5H-benzo[6,7]cyclohepta[1,2-d]pyrimidin-2-ylamine (Example 5) | 80 |
| 4-(3-Methylamino-azetidin-1-yl)-6,7-dihydro-5H-benzo[6,7]cyclohepta[1,2-d]pyrimidin-2-ylamine (Example 6) | 11 |
| Sulfamide, N-[(3,4-dichlorophenyl)methyl]-N'-[2-(1H-imidazol-4-yl)ethyl]- (Example 7) | 33 |

In addition to the utility of in vitro methods for characterizing the potency of compounds at the $H_4$ receptor, there are animal disease models available which demonstrate the utility of compounds. There are a number of methods to test the activity of compounds in different pain models that are well known to those skilled in the art. Pain states are exhibited by humans and other animals, and there are numerous animal models of pain; a review of animal models of pain is found in Joshi and Honore, Expert Opinion in Drug Discovery (2004) 1, pp. 323-334. A description of the formalin test in rats, neuropathic pain models in rats, general descriptions of methods of testing and descriptions of pain models are found in the book 'Drug Discovery and Evaluation, $2^{nd}$ edition' (H. Gerhard Vogel, editor; Springer-Verlag, New York, 2002; pp. 702-706).

One example of human disease which may be treated relates to a novel utility for $H_4$ antagonists, the treatment of pain. The utility of histamine $H_4$ receptor ligands to treat pain has not been reported, whether inflammatory pain, non-inflammatory pain, or neuropathic pain. This invention discloses the novel utility of the compounds of the invention to treat pain, including multiple types of pain, including inflammatory pain, non-inflammatory pain, and neuropathic pain.

Neuropathic pain is distinct from other types of pain (e.g. inflammatory pain), and can develop in response to previous or ongoing tissue injury, nerve injury, or diabetes, but persists long after signs of the original injury or damage have disappeared. Neuropathic pain is not well treated currently and therefore there is a strong need for methods to treat this particular type of pain. The topic of neuropathic pain has been reviewed in the scientific literature, for example, Smith, et al. Drug Development Research (2001) vol. 54(3), pp. 140-153; Collins and Chessell Expert Opinion on Emerging Drugs (2005) vol. 10(1), pp. 95-108; Vinik and Mehrabyan Medical Clinics of North America (2004), vol. 88(4), pp. 947-999; Dray, Urban, and Dickenson Trends in Pharmacological Sciences (1994) vol. 15(6) pp. 190-7; Dworkin Clinical Journal of Pain (2002) vol. 18(6) pp. 343-9. There do exist a number of animal models of neuropathic pain that can be used to assess the ability of the compounds of the invention to treat neuropathic pain, as discussed inter alia.

Animal models of neuropathic pain are predictive of efficacy of treatment of neuropathic pain in humans. These models are used to assess the efficacy of compounds of the invention in treating neuropathic pain. Example models well known to those skilled in the art include the Chung model (Kim and Chung, Pain (1992) vol. 50 pp. 355-363) and the Bennett model (Bennett and Xie, Pain (1988) vol. 30 pp. 87-107).

Activity of histamine H4 receptor ligands in Non-inflammatory Pain Models

Determination of Analgesic Effect Against Neuropathic Pain

Animals were prepared for testing, by use of a surgical procedure that induces neuropathic pain in one paw. Male Sprague Dawley rats were purchased from Charles River (Portage, Mich.). Prior to surgery, animals were housed in groups and maintained in a temperature-regulated environment. Following nerve ligation surgery, animals were housed in groups, and had access to food and water ad libitum.

The L5 and L6 spinal nerves of anesthetized rats were tightly ligated in a manner described previously (see Kim and Chung, Pain (1992) vol. 50 pp. 355-363). An incision was made on the dorsal portion of the hip and the muscle was blunt-dissected to reveal the spinal processes. The L6 transverse process was removed, and the left side L5 and L6 spinal nerves were tightly ligated with 5.0 braided silk suture. The wound was cleaned, the membrane sewn with 4.0 dissolvable Vicryl suture and the skin closed with wound clips. The paw affected by the surgical procedure (the left paw) develops an allodynic response, a hypersensitivity to mechanical and other stimuli; neuropathic pain is assessed as an increased sensitivity in the surgically affected (left) allodynic paw compared to the control paw on the right side, and measured by comparing the response of the (left side) allodynic paw to the response of the unaffected right side control paw.

For the assessment of neuropathic pain, mechanical allodynia in the affected paw of animals that had undergone spinal nerve ligation was evaluated using testing with von Frey filaments. As described previously by S. R. Chaplan, et al ("Quantitative assessment of tactile allodynia in the rat paw" J. Neurosci. Meth. (1994) vol. 53 pp. 55-63), two weeks following surgery rats were acclimated to a testing box constructed of plexiglass with a wire mesh floor which allowed access to the plantar surface of the animal's hindpaws. Using an Up-Down method (Dixon, Annual Rev. Pharmacol. Toxicol. (1980) vol. 20, pp. 441-462; Chaplan et al. "Quantitative assessment of tactile allodynia in the rat paw" J. Neuroscience Methods (1994) vol. 53 pp. 55-63), von Frey filaments of increasing stiffness were applied to the plantar surface of the hindpaws and the withdrawal response of the animals was observed; for the surgically affected paw with neuropathic pain (the left side paw) the baseline level of allodynia has a withdrawal threshold of ≦4 g of pressure. By comparison, for the control paw without allodynia (in this case the right side paw), the typical withdrawal pressure is around 15 g. Representative compounds of the invention, administered intraperitoneally 30 minutes before testing, are able to reduce the symptoms of neuropathic pain and induce a dose-dependent increase in the withdrawal threshold for allodynic (left side) limb, up to a maximum effect of 15 g. The efficacy of the compound in reducing neuropathic pain at different doses is determined by comparing response in the surgery-affected paw versus the response in the control paw. This is expressed as the MPE (maximum percent effect), or 100 times the withdrawal threshold of the allodynic (left side) divided by the withdrawal threshold of the control (right side).

The following table of representative histamine $H_4$ receptor ligands is provided, along with potency values:

| Compound Name (Example number) | Dose injected, micromole/kg, i.p. (intraperitoneally) | MPE (%) |
| --- | --- | --- |
| 4-(2-amino-6-(4-methylpiperazin-1-yl)pyrimidin-4-yl)benzonitrile, maleate (Example 1) | 30 | 14 |
| 4-(2-amino-6-(4-methylpiperazin-1-yl)pyrimidin-4-yl)benzonitrile, maleate (Example 1) | 100 | 44 |
| 4-(2-amino-6-(4-methylpiperazin-1-yl)pyrimidin-4-yl)benzonitrile, maleate (Example 1) | 300 | 77 |
| 4-(2-amino-6-(4-methylpiperazin-1-yl)pyrimidin-4-yl)benzonitrile, maleate (Example 1) | 500 | 97 |
| 5-Chloro-1H-indol-2-yl)-(4-methyl-piperazin-1-yl)-methanone (Example 3) | 100 | 16 |
| 5-Chloro-1H-indol-2-yl)-(4-methyl-piperazin-1-yl)-methanone (Example 3) | 250 | 50 |
| 5-Chloro-1H-indol-2-yl)-(4-methyl-piperazin-1-yl)-methanone (Example 3) | 500 | 94 |
| 4-((3R)-3-Amino-pyrrolidin-1-yl)-6,7-dihydro-5H-benzo[6,7]cyclohepta[1,2-d]pyrimidin-2-ylamine (Example 4) | 100 | 47 |
| 4-Piperazin-1-yl-6,7-dihydro-5H-benzo[6,7]cyclohepta[1,2-d]pyrimidin-2-ylamine (Example 5) | 100 | 28 |
| 4-(3-Methylamino-azetidin-1-yl)-6,7-dihydro-5H-benzo[6,7]cyclohepta[1,2-d]pyrimidin-2-ylamine (Example 6) | 100 | 36 |
| 4-(3-Methylamino-azetidin-1-yl)-6,7-dihydro-5H-benzo[6,7]cyclohepta[1,2-d]pyrimidin-2-ylamine (Example 6) | 300 | 78 |

Representative compounds are active in this model, with preferred compounds of the invention active in the model at doses of ranging about 30-500 micromoles/kg of body weight.

Determination of Analgesic Effect Against Neuropathic Pain

The compounds demonstrate efficacy in a chronic constriction injury model of neuropathic pain, the so-called Bennett model (Bennett and Xie, Pain (1988) vol. 30 pp. 87-107) in rats. To prepare animals for the model, an incision of about 1.5 cm was made about 0.5 cm below the rat pelvis. The biceps femoris and the gluteous superficialis (right side) were separated and the sciatic nerve exposed, isolated, and four loose ligatures (5-0 chromic catgut) with 1 mm spacing were placed around it. The rats were allowed to recover and then placed in a cage with soft bedding for 10 days before assessment of pain response to mechanical stimulus by the method described above for the Chung model.

The following table of representative histamine $H_4$ receptor ligands is provided, along with potency values:

| Compound Name (Example number) | Dose injected, micromole/kg, i.p. | MPE (%) |
| --- | --- | --- |
| 4-(2-amino-6-(4-methylpiperazin-1-yl)pyrimidin-4-yl)benzonitrile, maleate (Example 1) | 100 | 18 |
| 4-(2-amino-6-(4-methylpiperazin-1-yl)pyrimidin-4-yl)benzonitrile, maleate (Example 1) | 300 | 63 |
| 5-Chloro-1H-indol-2-yl)-(4-methyl-piperazin-1-yl)-methanone (Example 3) | 250 | 32 |
| 5-Chloro-1H-indol-2-yl)-(4-methyl-piperazin-1-yl)-methanone (Example 3) | 500 | 73 |

Representative compounds are active in this model, with preferred compounds of the invention active in the model at doses of ranging about 100-500 micromoles/kg of body weight.

Skin-Incision Model

This is a surgical skin incision model (Joshi, et al. Pain 123 (2006) 75-82). Animals (rats) were prepared for testing by subjecting them to a surgical procedure carried out under sterile conditions, where the plantaris muscle was elevated and incised longitudinally with the origin and insertion of the muscle remaining intact. The skin was then closed with two mattress sutures (e.g. 5-0 nylon sutures). After surgery, animals were allowed to recover on a warming plate and housed individually in cages with soft bedding. After this surgery, the animals develop a hypersensitivity called allodynia; allodynia is pain due to a stimulus that does not normally provoke pain. Animals were tested for mechanical allodynia using von Frey hair mechanical stimulation 2, 24, and 48 h after surgery as described for the Chung model.

The following table of representative histamine $H_4$ receptor ligands is provided, along with potency values:

| Compound Name (Example number) | Dose injected, micromole/kg, i.p. (intraperitoneally) | MPE (%) |
| --- | --- | --- |
| 4-(2-amino-6-(4-methylpiperazin-1-yl)pyrimidin-4-yl)benzonitrile, maleate (Example 1) | 30 | 31 |
| 4-(2-amino-6-(4-methylpiperazin-1-yl)pyrimidin-4-yl)benzonitrile, maleate (Example 1) | 100 | 65 |
| 5-Chloro-1H-indol-2-yl)-(4-methyl-piperazin-1-yl)-methanone (Example 3) | 250 | 46 |
| 5-Chloro-1H-indol-2-yl)-(4-methyl-piperazin-1-yl)-methanone (Example 3) | 500 | 79 |
| 4-(3-Methylamino-azetidin-1-yl)-6,7-dihydro-5H-benzo[6,7]cyclohepta[1,2-d]pyrimidin-2-ylamine (Example 6) | 30 | 21 |
| 4-(3-Methylamino-azetidin-1-yl)-6,7-dihydro-5H-benzo[6,7]cyclohepta[1,2-d]pyrimidin-2-ylamine (Example 6) | 100 | 69 |
| Sulfamide, N-[(3,4-dichlorophenyl)methyl]-N'-[2-(1H-imidazol-4-yl)ethyl]- (Example 7) | 3 | 33 |
| Sulfamide, N-[(3,4-dichlorophenyl)methyl]-N'-[2-(1H-imidazol-4-yl)ethyl]- (Example 7) | 10 | 50 |

Representative compounds are active in this model, with preferred compounds of the invention active in the model at doses of ranging about 30-500 micromoles/kg of body weight.

Activity in an Osteoarthritis Model

Unilateral knee joint osteoarthritis was induced in rats by a single intra-articular (i.a.) injection of sodium monoiodoacetate (MIA) (Sigma-Aldrich, St. Louis, Mo.) (3 mg in 50 ul sterile isotonic saline) into the right knee joint cavity under light (1-3%) isoflurane anesthesia.

Pain behavior was assessed by measurement of hind limb grip force (GF) in adult osteoarthritic rats. Following the unilateral injection of MIA (male Sprague Dawley, 325-350 g, tested at 20 days following MIA injection), a behavioral measure of activity-induced pain was carried out. Measurements of the peak hind limb grip force were conducted by recording the maximum compressive force ($CF_{max}$), in grams of force, exerted on a hind limb strain gauge setup, in a commercially available grip force measurement system (Columbus Instruments, Columbus, Ohio).

During testing, each rat was gently restrained by grasping it around its rib cage and then allowed to grasp the wire mesh frame attached to the strain gauge. The experimenter then moved the animal in a rostral-to-caudal direction until the grip was broken. Each rat was sequentially tested twice at approximately 2-3 min interval to obtain a raw mean grip force ($CF_{max}$). This raw mean grip force data was in turn converted to a maximum hindlimb cumulative compressive force ($CF_{max}$), as the grams of force/kg of body weight, for each animal.

For evaluating the compound effects, the hind limb grip force was conducted 20 days following the intra-articular injection of MIA. A group of age-matched naïve (not injected with MIA) animals was added as a comparator to the drug-dosed groups. The vehicle control response for each group of MIA-treated animals was defined as the 0% response (0% effect), whereas the naïve control group was defined as the normal response and as 100% effect. The % effects for each dose group was expressed as % return of response to normalcy, compared to the naïve group. That is, the % effect= (Treatment $CF_{max}$–Vehicle $CF_{max}$)/Vehicle $CF_{max}$]×100). All experiments evaluating drug effects in this model were conducted in a randomized blinded fashion.

The following table of representative histamine $H_4$ receptor ligands is provided, along with potency values:

| Compound Name (Example number) | dose injected, micromole/kg, i.p. (intraperitoneally) | % Effect |
| --- | --- | --- |
| 5-Chloro-1H-indol-2-yl)-(4-methyl-piperazin-1-yl)-methanone (Example 3) | 100 | 21 |
| 5-Chloro-1H-indol-2-yl)-(4-methyl-piperazin-1-yl)-methanone (Example 3) | 250 | 47 |
| Sulfamide, N-[(3,4-dichlorophenyl)methyl]-N'-[2-(1H-imidazol-4-yl)ethyl]- (Example 7) | 100 | 22 |

Representative compounds are active in this model, with preferred compounds of the invention active in the model at doses of ranging about 100-250 micromoles/kg of body weight.

Activity of histamine $H_4$ Receptor Ligands in Inflammatory Pain Models Determination of Analgesic Effect Against Inflammatory Pain To assess the effectiveness of representative compounds of the invention against acute model inflammatory pain, animals were tested in an acute model of carrageenan-induced thermal hyperalgesia (see for example, Honore, et al. *Behavioural Brain Research* 167 (2006) 355-364; Porreca, et al. *Journal of Pharmacology and Experimental Therapeutics* (2006) vol. 318 pp. 195-205). Carrageenan was injected into the test paw of the animal, and after 90 minutes, the test drug was administered by intraperitoneal dosing. The effect on thermal hyperalgesia was assessed in a hotbox assay which was done 30 minutes after the intraperitoneal dosing of the test drug, and the MPE (maximal percent effect) reported by comparison to the control paw (not injected with carrageenan), according to 100 times the withdrawal latency of the carrageenan injected paw (in seconds) divided by the withdrawal latency of the control (not injected with carrageenan) paw.

The following table of representative histamine $H_4$ receptor ligands is provided, along with potency values:

| Compound Name (Example number) | dose injected, micromole/kg, i.p. (intraperitoneally) | MPE (%) |
| --- | --- | --- |
| 4-(2-amino-6-(4-methylpiperazin-1-yl)pyrimidin-4-yl)benzonitrile, maleate (Example 1) | 30 | 36 |
| 4-(2-amino-6-(4-methylpiperazin-1-yl)pyrimidin-4-yl)benzonitrile, maleate | 100 | 100 |

| Compound Name (Example number) | dose injected, micromole/kg, i.p. (intraperitoneally) | MPE (%) |
|---|---|---|
| (Example 1) | | |
| 5-Chloro-1H-indol-2-yl)-(4-methyl-piperazin-1-yl)-methanone (Example 3) | 30 | 23 |
| 5-Chloro-1H-indol-2-yl)-(4-methyl-piperazin-1-yl)-methanone (Example 3) | 100 | 49 |
| 5-Chloro-1H-indol-2-yl)-(4-methyl-piperazin-1-yl)-methanone (Example 3) | 300 | 96 |
| 4-((3R)-3-Amino-pyrrolidin-1-yl)-6,7-dihydro-5H-benzo[6,7]cyclohepta[1,2-d]pyrimidin-2-ylamine (Example 4) | 100 | 68 |
| 4-Piperazin-1-yl-6,7-dihydro-5H-benzo[6,7]cyclohepta[1,2-d]pyrimidin-2-ylamine (Example 5) | 100 | 23 |
| 4-(3-Methylamino-azetidin-1-yl)-6,7-dihydro-5H-benzo[6,7]cyclohepta[1,2-d]pyrimidin-2-ylamine (Example 6) | 100 | 41 |
| Sulfamide, N-[(3,4-dichlorophenyl)methyl]-N'-[2-(1H-imidazol-4-yl)ethyl]-(Example 7) | 3 | 33 |
| Sulfamide, N-[(3,4-dichlorophenyl)methyl]-N'-[2-(1H-imidazol-4-yl)ethyl]-(Example 7) | 10 | 42 |
| Sulfamide, N-[(3,4-dichlorophenyl)methyl]-N'-[2-(1H-imidazol-4-yl)ethyl]-(Example 7) | 30 | 93 |

Representative compounds are active in this model, with preferred compounds of the invention active in the model at doses of ranging about 3-300 micromoles/kg of body weight.

Determination of Analgesic Effect Against Hyperalgesia

To assess the effectiveness of representative compounds of the invention against hyperalgesia, animals were tested in an acute model of adjuvant-induced thermal hyperalgesia (see for example, Honore, et al. *Behavioural Brain Research* 167 (2006) 355-364; Carroll, et al. US Patent application US 2006/0025614A 1). To prepare animals for the model, a solution of Complete Freund's adjuvant (150 microliters of a 50% aqueous solution, Sigma Chemical Company, St. Louis, Mo.) was injected into the plantar surface of test paw of the animal (rat). Rats so injected develop a hyperalgesia to thermal stimulation which is assessed 48 hours after injection of the Complete Freund's adjuvant using a commercially available paw thermal stimulator (UARDG, Dept. of Anesthesiology, Univ. California at San Diego, La Jolla, Calif.). For testing, rats were placed individually in a so-called 'hot box' (i.e. Plexiglass cubicles mounted on a glass surface) maintained at 30° C., and allowed a 30 minute habituation period. A thermal stimulus, in the form of radiant heat emitted from a focused projection bulb, was then applied to the plantar surface of each hind paw. The stimulus current was maintained (e.g. at 4.5 Amp) and the time of exposure set to limit the extent of possible tissue damage (e.g. maximum of 20 seconds exposure to thermal heating from the projection bulb). The time (in seconds) for the withdrawal of the paw that was injected with the Complete Freund's adjuvant (CFA) and subjected to the thermal stimulus was recorded, and this was compared to the time (in seconds) for withdrawal of the uninjected paw subjected to the same thermal stimulus. The paw injected with CFA develops a thermal hyperalgesia which is expressed as a shorter time (typically around 6 seconds) before paw withdrawal under thermal stimulus; uninjected paws do not show thermal hyperalgesia and have a normal withdraw time (typically around 10-12 seconds). To test the effect of a compound on the hyperalgesia, the test compound is dissolved in a vehicle (e.g. water or saline) and administered by i.p. (intraperitoneal) injection 30 minutes before the testing of the animal's response to the thermal stimulus to the paws. The antihyperalgesic activity of the compound in blocking the pain is shown by an increase in the time to withdraw the CFA-injected paw subjected to thermal stimulus. Experiments are done with single-dose and escalating-dosages of the test compound, and dose response curves constructed to determine $ED_{50}$ values.

The following table of representative histamine $H_4$ receptor ligands is provided, along with potency values:

| Compound Name (Example number) | dose injected, micromole/kg, i.p. (intraperitoneally) | MPE (%) |
|---|---|---|
| 4-(2-amino-6-(4-methylpiperazin-1-yl)pyrimidin-4-yl)benzonitrile, maleate (Example 1) | 30 | 62 |
| 4-(2-amino-6-(4-methylpiperazin-1-yl)pyrimidin-4-yl)benzonitrile, maleate (Example 1) | 100 | 88 |
| 4-(4-methylpiperazin-1-yl)-6-(pyridin-3-yl)pyrimidin-2-amine, maleate (Example 2) | 30 | 51 |
| 4-(4-methylpiperazin-1-yl)-6-(pyridin-3-yl)pyrimidin-2-amine, maleate (Example 2) | 100 | 83 |
| 5-Chloro-1H-indol-2-yl)-(4-methyl-piperazin-1-yl)-methanone (Example 3) | 30 | 27 |
| 5-Chloro-1H-indol-2-yl)-(4-methyl-piperazin-1-yl)-methanone (Example 3) | 300 | 81 |

Representative compounds are active in this model, with preferred compounds of the invention active in the model at doses of ranging about 30-300 micromoles/kg of body weight.

In a separate method of assessing the effectiveness of representative compounds of the invention against hyperalgesia, animals were tested in the acute model of adjuvant-induced hyperalgesia using Complete Freund's Adjuvant (CFA) as described above, but in this case, tactile allodynia to a mechanical stimulus was measured using calibrated von Frey filaments (Stoelting, Wood Dale, Ill.). Animals were prepared as described above: a solution of Complete Freund's adjuvant (150 microliters of a 50% aqueous solution, Sigma Chemical Company, St. Louis, Mo.) was injected into the plantar surface of test paw of the animal (rat). Rats so injected develop a hyperalgesia to mechanical (touch) stimulation which is assessed 48 hours after injection of the Complete Freund's adjuvant. Withdrawal threshold was determined by increasing and decreasing stimulus intensity, and estimated using the Dixon's up-down method (Dixon, Annual Rev. Pharmacol. Toxicol. (1980) vol. 20, pp. 441-462; Chaplan et al. "Quantitative assessment of tactile allodynia in the rat paw" J. Neuroscience Methods (1994) vol. 53 pp. 55-63). Rats were placed into inverted individual plastic containers (20×12.5× 20 cm) on top of a suspended wire mesh with a 1 cm² grid to provide access to the ventral side of the hind paws, and acclimated to the test chambers for 20 min. The von Frey filaments were presented perpendicularly to the plantar surface of the selected hind paw, and then held in this position for approximately 8 seconds with enough force to cause a slight bend in the filament. Positive responses included an abrupt withdrawal of the hind paw from the stimulus, or flinching behavior immediately following removal of the stimulus. Withdrawal threshold was determined using an up-down procedure (Dixon, Annual Rev. Pharmacol. Toxicol. (1980) vol. 20, pp. 441-462; Chaplan et al. "Quantitative assessment of tactile allodynia in the rat paw" J. Neuroscience Methods (1994) vol. 53 pp. 55-63). The strength of the maximum filament used for von Frey testing was 15.0 g.

The following table of representative histamine $H_4$ receptor ligands is provided, along with potency values:

| Compound Name (Example number) | dose injected, micromole/kg, i.p. (intraperitoneally) | MPE (%) |
|---|---|---|
| 4-(2-amino-6-(4-methylpiperazin-1-yl)pyrimidin-4-yl)benzonitrile, maleate (Example 1) | 30 | 42 |
| 4-(2-amino-6-(4-methylpiperazin-1-yl)pyrimidin-4-yl)benzonitrile, maleate (Example 1) | 100 | 63 |
| 5-Chloro-1H-indol-2-yl)-(4-methyl-piperazin-1-yl)-methanone (Example 3) | 30 | 55 |
| 5-Chloro-1H-indol-2-yl)-(4-methyl-piperazin-1-yl)-methanone (Example 3) | 300 | 71 |
| 4-(3-Methylamino-azetidin-1-yl)-6,7-dihydro-5H-benzo[6,7]cyclohepta[1,2-d]pyrimidin-2-ylamine (Example 6) | 30 | 35 |
| 4-(3-Methylamino-azetidin-1-yl)-6,7-dihydro-5H-benzo[6,7]cyclohepta[1,2-d]pyrimidin-2-ylamine (Example 6) | 100 | 49 |

Representative compounds are active in this model, with preferred compounds of the invention active in the model at doses of ranging about 30-100 micromoles/kg of body weight.

Compounds of the invention are histamine $H_4$ receptor ligands that modulate function of the histamine $H_4$ receptor by altering the activity of the receptor. They may be antagonists, inverse agonists, or partial agonists. Preferrably the compounds are antagonists. More preferably the ligands are histamine $H_4$ receptor inverse agonists.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations, or methods, or any combination of such changes and modifications of use of the invention, may be made without departing from the spirit and scope thereof.

What is claimed is:

1. A method of treating pain comprising administering to a subject a therapeutically effective amount of a compound of Formula (VI):

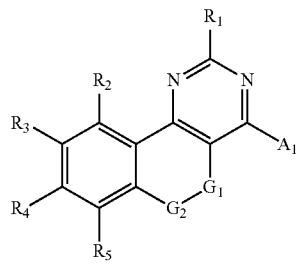

Formula (VI)

or a pharmaceutically acceptable salt thereof,
wherein:

$G_1$ is alkylene;

$G_2$ is alkylene;

wherein each carbon of the alkylene $G_1$ and $G_2$ may be optionally substituted with one or more groups selected from alkyl, fluoroalkyl, cyanoalkyl, cycloalkyl, fluorocycloalkyl, cycloalkoxyalkyl, alkylcycloalkyl, alkylfluorocycloalkyl, fluorine, acyl, acyloxy, alkenyl, alkoxy, alkoxyalkoxy, alkoxyalkyl, alkoxycarbonyl, alkylcarbonyl, alkylsulfonyl, alkynyl, amido, carboxy, cyano, fluoroalkoxy, formyl, haloalkoxy, haloalkyl, halogen, hydroxy, hydroxyalkyl, mercapto, nitro, alkylthio, and oxo, $R_1$ is selected from H, $NH_2$, —NH (acyl), —NH(alkyl), —N(alkyl)$_2$, —NH(C=)aryl, —NH—alkylene(NR$_8$R$_9$), —NH(C=O)-alkylene(NR$_8$R$_9$), —NR$_8$(C=O), —NR$_8$R$_9$, —NH-alkylene-heteroaryl, —NHOH, —NHOCH$_3$, —O-alkylene(NR$_8$R$_9$), alkyl, piperazine, fluoroalkyl, cyanoalkyl, cycloalkyl, fluorocycloalkyl, hydroxyalkyl, cyano, alkoxycarbonyl, carboxy, —(C=O)—(NR$_8$R$_9$), —(C=O)—NH-alkylene (NR$_8$R$_9$), and alkoxy;

$R_2$, $R_3$, $R_4$ and $R_5$ are each independently selected hydrogen, alkyl fluoroalkyl, cyanoalkyl, cycloalkyl, fluorocycloalkyl, cycloalkoxyalkyl, alkylcycloalkyl, alkylfluorocycloalkyl, aryl, heteroaryl, heterocycle, O-aryl, O-heteroaryl, S-aryl, CONR$_8$R$_9$, NR$_8$CO-alkyl, NR$_8$(C=O)O-alkyl, acyl, acyloxy, alkenyl, alkoxy, alkoxyalkoxy, alkoxyalkyl, alkoxycarbonyl, alkoxyimino, alkoxysulfonyl, alkylcarbonyl, alkylsulfonyl, alkynyl, amido, carboxy, cyano, fluoroalkoxy, formyl, haloalkoxy, haloalkyl, halogen, hydroxy, hydroxyalkyl, mercapto, nitro, alkylthio —NR$_8$R$_9$, -carbonyl(NR$_8$R$_9$), —SO$_2$ NR$_8$R$_9$), and N(R$_8$)SO$_2$(R$_9$), or $R_3$ and $R_4$ taken to ether are —CH$_2$CH$_2$CH$_2$—, —CH$_2$CH$_2$CH$_2$CH$_2$—, or —CH$_2$OCH$_2$—;

$R_6$ is selected from hydrogen, alkyl, fluoroalkyl, cyanoalkyl, hydroxyalkyl, alkoxyalkyl, cycloalkyl, fluorocycloalkyl, cycloalkoxyalkyl, alkylcycloalkyl, and alkylfluorocycloalkyl;

$R_7$ is selected from fluoroalkyl, hydroxyalkyl, alkoxyalkyl, fluorocycloalkyl, and alkylfluorocycloalkyl;

$R_8$ and $R_9$ are each independently selected from hydrogen, alkyl, fluoroalkyl, cycloalkyl, cyanoalkyl, fluorocycloalkyl, cycloalkoxyalkyl, alkylcycloalkyl, alkylfluorocycloalkyl, aryl, heteroaryl, heterocycle, acyl, alkoxy alkyl, alkoxycarbonyl, alkylcarbonyl, alkylsulfonyl, amido, formyl, hydroxy, and hydroxyalkyl;
$A_1$ is a group of structure $A_2$ or $A_3$
wherein $A_2$ is selected from
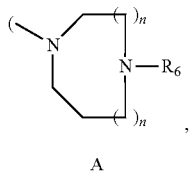
A
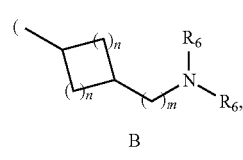
B
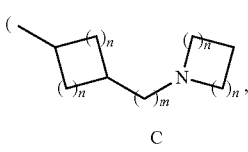
C
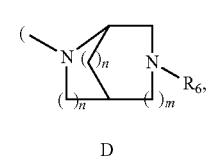
D
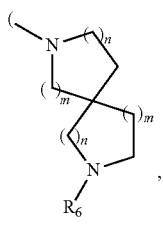
E
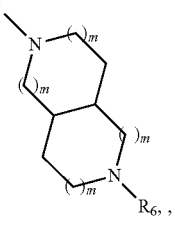
F
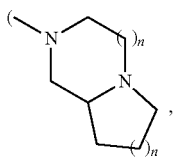
G
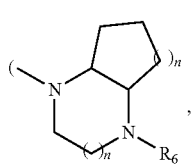
F
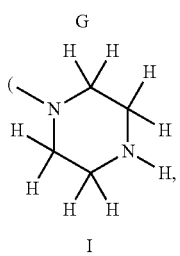
I
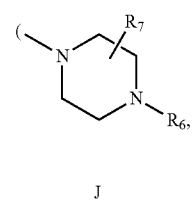
J
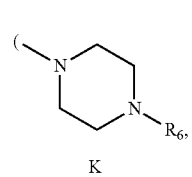
K
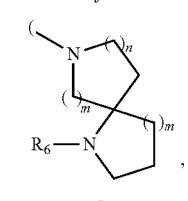
L
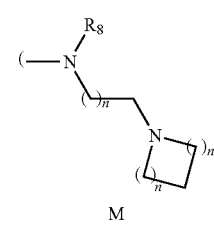
M
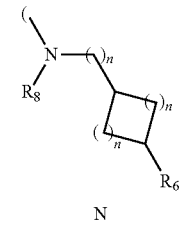
N
-continued
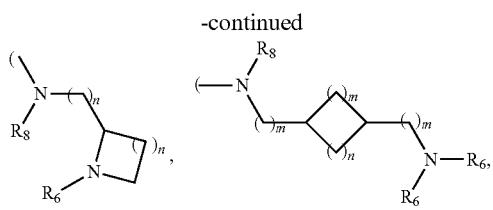
O   P
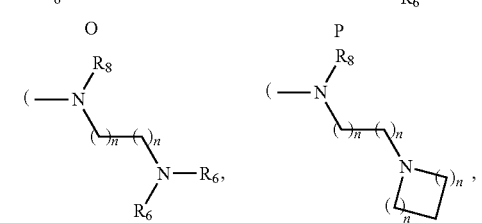
Q   R
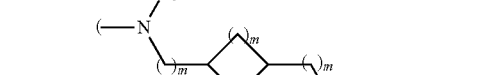
S
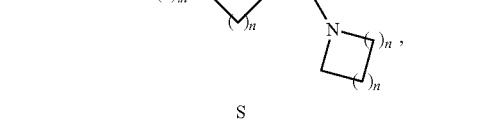
T   U
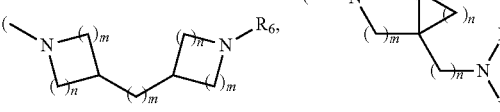
V   W
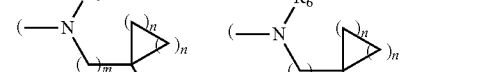
X
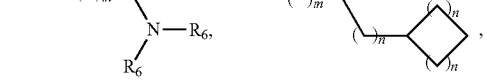
Y1
Y2   Y3
Y4   Y5

-continued

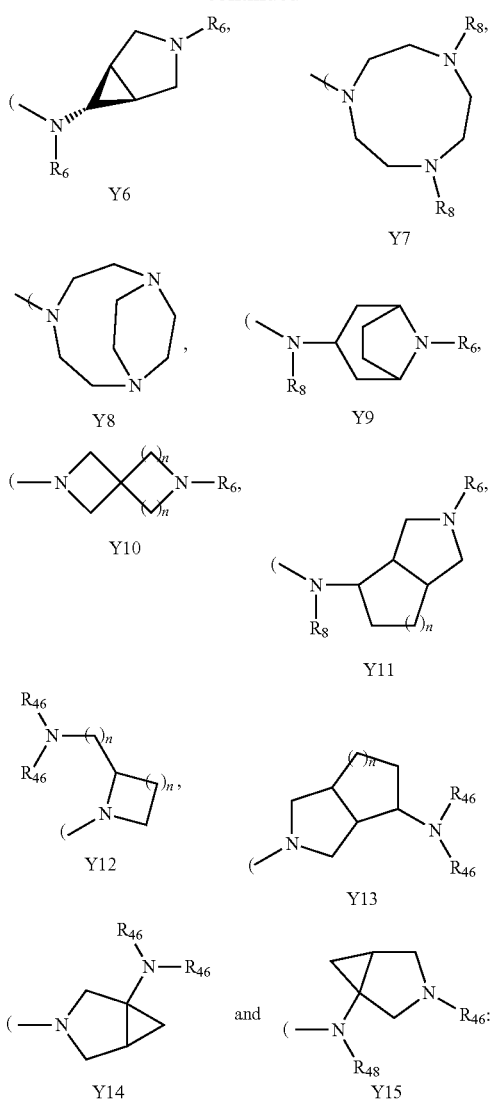

and A₃ is selected from

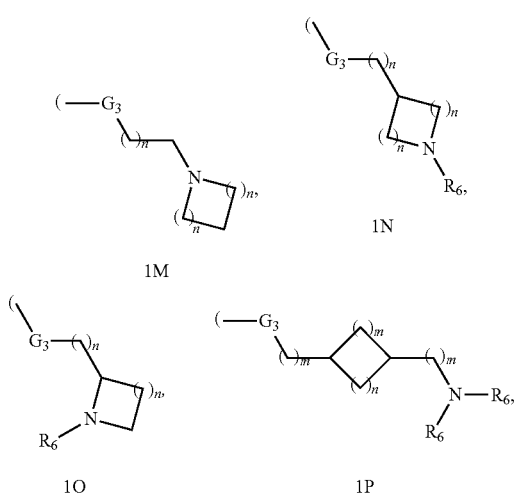

-continued

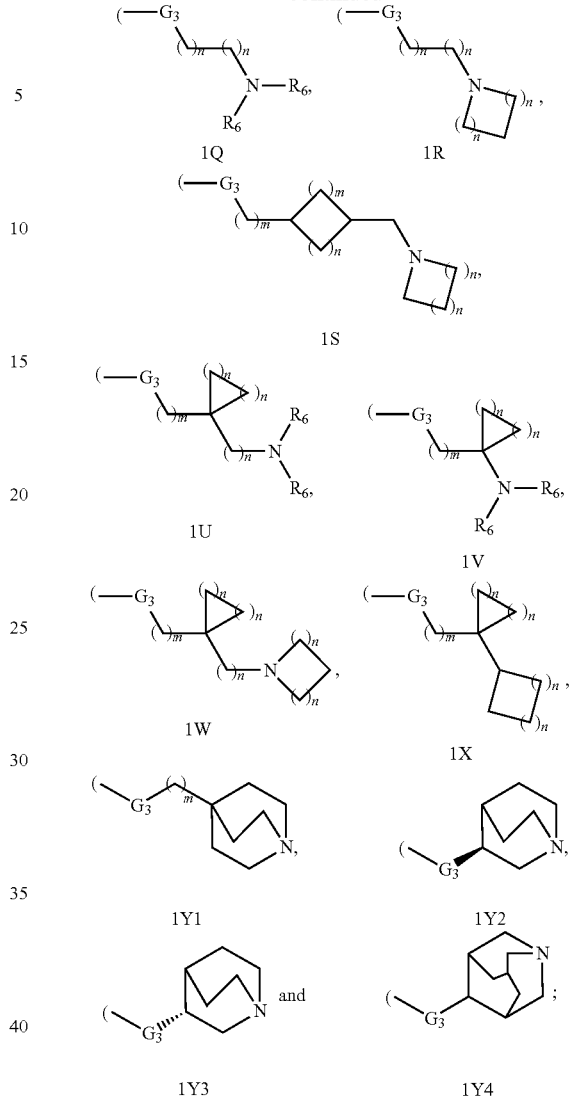

wherein G₃ is O, S, S(O), or S(O)₂; n is 1, 2, or 3; and m is 0, 1, or 2;

wherein each carbon atom of groups A₁ may be optionally substituted with one or more groups selected from alkyl, fluoroalkyl, cyanoalkyl, cycloalkyl, fluorocycloalkyl, cycloalkoxyalkyl, alkylcycloalkyl, alkylfluorocycloalkyl, fluorine, acyl, acyloxy, alkenyl, alkoxy, alkoxyalkoxy, alkoxyalkyl, alkoxycarbonyl, alkylcarbonyl, alkylsulfonyl, alkynyl, amido, carboxy, cyano, fluoroalkoxy, formyl, haloalkoxy, haloalkyl, halogen, hydroxy, hydroxyalkyl, mercapto, nitro, and alkylthio;

provided that when G₁ is CH₂CH₂ and G₂ is CH₂ and R₁ is selected from NH₂, NHalkyl or alkyl, then A₁ is not a group of structure K.

2. The method of claim 1, wherein the pain is inflammatory pain, inflammatory hyperalgesia, hyperalgesia, neuropathic pain, migraine, cancer pain, visceral pain, osteoarthritis pain, or post-surgical pain.

3. The method of claim 1, wherein the pain is neuropathic pain, migraine, cancer pain, visceral pain, osteoarthritis pain, or post-surgical pain.

4. The method of claim 1, wherein the pain is neuropathic pain, osteoarthritis pain, or post-surgical pain.

5. The method of claim 1, wherein the pain is osteoarthritis pain.

6. The method of claim 1, wherein the pain is post-surgical pain.

7. The method of claim 1, wherein the pain is neuropathic pain.

8. The method of claim 1, wherein the neuropathic pain is peripheral neuropathic pain syndrome, chemotherapy-induced neuropathy, complex regional pain syndrome, HIV sensory neuropathy, neuropathy secondary to tumor infiltration, painful diabetic neuropathy, phantom limb pain, postherpetic neuralgia, postmastectomy pain, trigeminal neuralgia, central neuropathic pain syndrome, central poststroke pain, multiple sclerosis pain, Parkinson disease pain, or spinal cord injury pain.

9. The method of claim 1, wherein the compound is
4-((R)-3-amino-pyrrolidin-1-yl)-6,7-dihydro-5H-benzo[6,7]cyclohepta[1,2-d]pyrimidin-2-ylamine;
4-piperazin-1-yl-6,7-dihydro-5H-benzo[6,7]cyclohepta[1,2-d]pyrimidin-2-yl amine; or
4-(3-methylamino-azetidin-1-yl)-6,7-dihydro-5H-benzo[6,7]cyclohepta-[1,2-d]pyrimidin-2-ylamine.

10. The method of claim 1, wherein the compound of Formula (VI) or the salt thereof is administered, in combination with at least one selected from a histamine $H_1$ antagonist; a histamine $H_2$ antagonist, histamine $H_3$ antagonist; a modulator of TNF-α, an anti-inflammatory corticocosteroid; a 5-lipoxygenase inhibitor; a leukotriene antagonist; a LTB4 antagonist; a non-steroidal anti-inflammatory drug; a COX-2 inhibitor; an anti-nociceptive opiate agonist, an anti-nociceptive alpha adrenergic agonist, a TRPV1 antagonist, a nicotinic acetylcholine receptor agonist, a CB-1 agonist; a CB-2 agonist; a P2X7 antagonist; and a metabotropic glutamate receptor antagonist.

11. The method of claim 3, wherein the compound is
4-((R)-3-amino-pyrrolidin-1-yl)-6,7-dihydro-5H-benzo[6,7]cyclohepta[1,2-d]pyrimidin-2-ylamine;
4-piperazin-1-yl-6,7-dihydro-5H-benzo[6,7]cyclohepta[1,2-d]pyrimidin-2-yl-amine; or
4-(3-methylamino-azetidin-1-yl)-6,7-dihydro-5H-benzo[6,7]cyclohepta-[1,2-d]pyrimidin-2-ylamine.

12. The method of claim 1, wherein $G_1$ is —$CH_2$—, —$CH_2CH_2$—, —$CH_2CH_2CH_2$—, or —$CH_2CH_2CH_2CH_2$—, and $G_2$ is —$CH_2$— or —$CH(CH_3)$—.

13. The method of claim 1, wherein $R_1$ is selected from H, —$NH_2$, —$NHCH_3$,

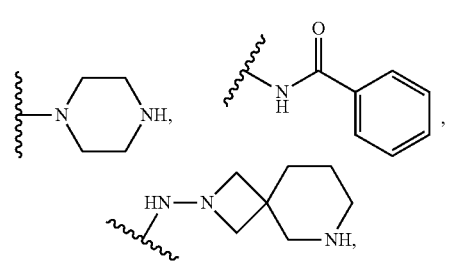

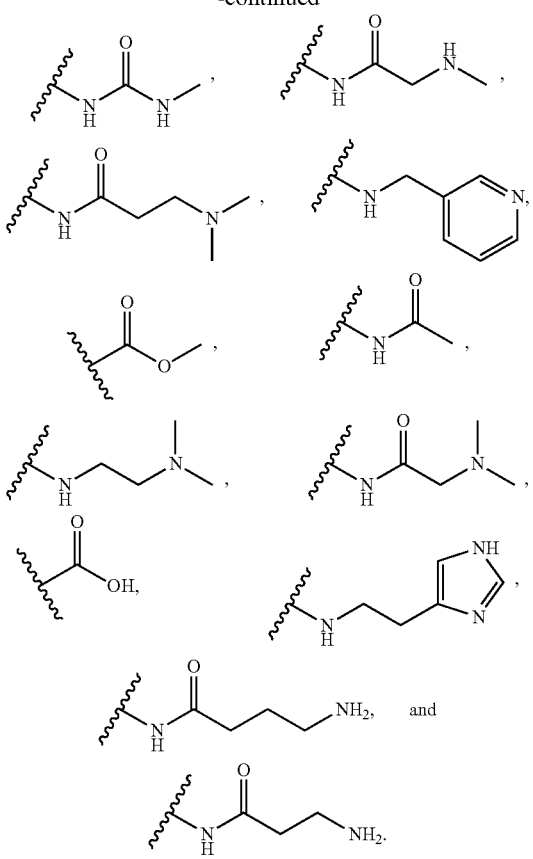

14. The method of claim 1, wherein $A_1$ is selected from

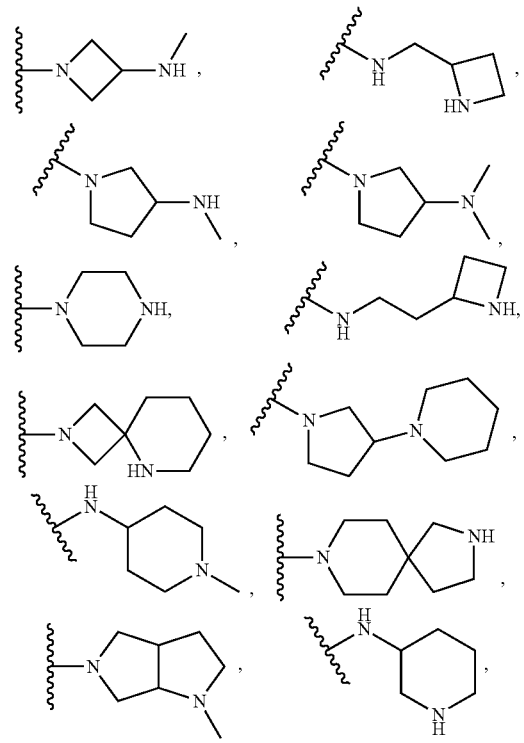

-continued

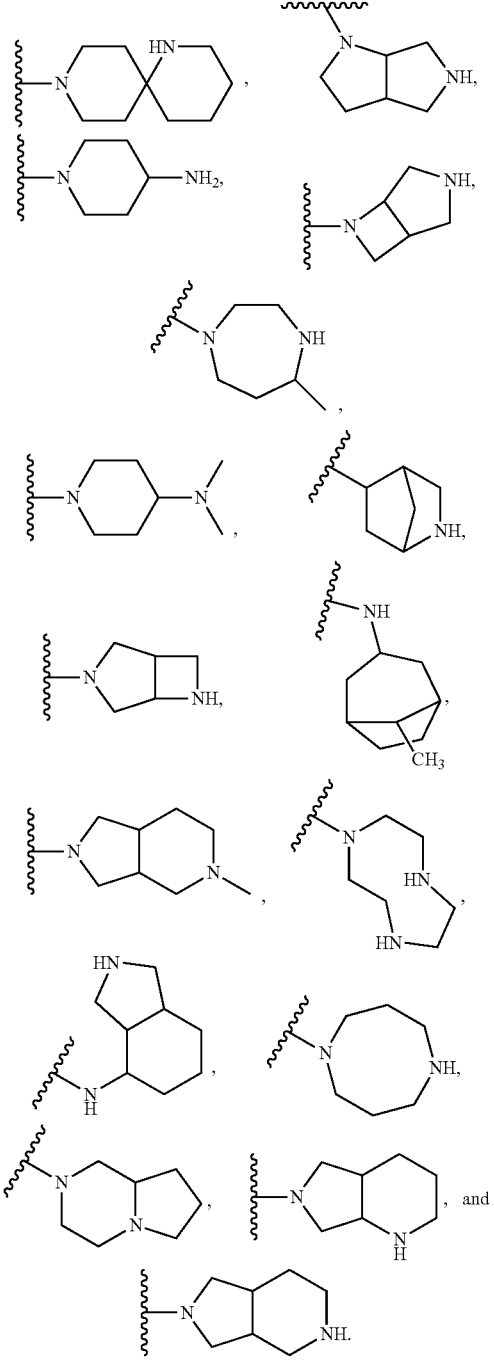

15. The method of claim 1, wherein $R_2$, $R_3$, $R_4$, and $R_5$ are independently selected from H, fluoro, methyl, methoxy, pyridin-3-yl, phenyl, —(C═O)OCH$_3$, cyano, —NHCH$_3$, —NH(C═O)CH$_3$, and

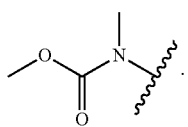

16. The method of claim 1, wherein the compound is selected from

6-Methyl-4-[(3R)-3-methylamino-pyrrolidin-1-yl]-5,6-dihydro-benzo[h]quinazolin-2-ylamine;

6-Methyl-4-(3-methylamino-azetidin-1-yl)-5,6-dihydro-benzo[h]quinazolin-2-ylamine;

6-Methyl-4-piperazin-1-yl-5,6-dihydro-benzo[h]quinazolin-2-ylamine;

4-(3-(R)-Methylamino-pyrrolidin-1-yl)-5,6-dihydro-benzo[h]quinazolin-2-ylamine;

4-(3-Methylamino-azetidin-1-yl)-5,6-dihydro-benzo[h]quinazolin-2-ylamine;

4-piperazin-1-yl-5,6-dihydro-benzo[h]quinazolin-2-ylamine;

(2,6-Diaza-spiro[3.5]non-2-yl)-6,7-dihydro-5H-benzo[6,7]cyclohepta[1,2-d]pyrimidin-2-ylamine;

$N^4$-(2-azetidin-2-ylethyl)-6,7-dihydro-5H-benzo[6,7]cyclohepta[1,2-d]pyrimidine-2,4-diamine;

$N^4$-[(2R)-azetidin-2-ylmethyl]-6,7-dihydro-5H-benzo[6,7]cyclohepta[1,2-d]pyrimidine-2,4-diamine;

$N^4$-(1-methylpiperidin-4-yl)-6,7-dihydro-5H-benzo[6,7]cyclohepta[1,2-d]pyrimidine-2,4-diamine;

$N^4$-(3-Piperidin-1-yl-propyl)-6,7-dihydro-5H-benzo[6,7]cyclohepta[1,2-d]pyrimidine-2,4-diamine;

$N^4$-Piperidin-3-yl-6,7-dihydro-5H-benzo[6,7]cyclohepta[1,2-d]pyrimidine-2,4-diamine;

$N^4$-(Octahydro-isoindol-4-yl)-6,7-dihydro-5H-benzo[6,7]cyclohepta[1,2-d]pyrimidine-2,4-diamine;

$N^4$-[(1R,5S)-8-methyl-8-azabicyclo[3.2.1]oct-3-yl]-6,7-dihydro-5H-benzo[6,7]cyclohepta[1,2-d]pyrimidine-2,4-diamine;

4-(3-Methylamino-azetidin-1-yl)-6,7-dihydro-5H-benzo[6,7]cyclohepta[1,2-d]pyrimidin-2-ylamine;

4-(3-(R)-Methylamino-pyrrolidin-1-yl)-6,7-dihydro-5H-benzo[6,7]cyclohepta[1,2-d]pyrimidin-2-ylamine;

4-piperazin-1-yl-6,7-dihydro-5H-benzo[6,7]cyclohepta[1,2-d]pyrimidin-2-ylamine;

10-Fluoro-4-(3-(R)-methylamino-pyrrolidin-1-yl)-6,7-dihydro-5H-benzo[6,7]cyclohepta[1,2-d]pyrimidin-2-ylamine;

10-Fluoro-4-(3-methylamino-azetidin-1-yl)-6,7-dihydro-5H-benzo[6,7]cyclohepta[1,2-d]pyrimidin-2-ylamine;

10-Fluoro-4-piperazin-1-yl-6,7-dihydro-5H-benzo[6,7]cyclohepta[1,2-d]pyrimidin-2-ylamine;

4-[(3S)-3-Methylamino-pyrrolidin-1-yl]-6,7-dihydro-5H-benzo[6,7]cyclohepta[1,2-d]pyrimidin-2-ylamine;

4-((3R)-3-Amino-pyrrolidin-1-yl)-6,7-dihydro-5H-benzo[6,7]cyclohepta[1,2-d]pyrimidin-2-ylamine;

4-(3-Piperidin-1-yl-pyrrolidin-1-yl)-6,7-dihydro-5H-benzo[6,7]cyclohepta[1,2-d]pyrimidin-2-ylamine;

4-(1,5-Diazocan-1-yl)-6,7-dihydro-5H-benzo[6,7]cyclohepta[1,2-d]pyrimidin-2-amine;

4-(4-Aminopiperidin-1-yl)-6,7-dihydro-5H-benzo[6,7]cyclohepta[1,2-d]pyrimidin-2-amine;

4-(5-Methyl-1,4-diazepan-1-yl)-6,7-dihydro-5H-benzo[6,7]cyclohepta[1,2-d]pyrimidin-2-amine;

4-((R)-3-Dimethylamino-pyrrolidin-1-yl)-6,7-dihydro-5H-benzo[6,7]cyclohepta[1,2-d]pyrimidin-2-ylamine;

N-(4-piperazin-1-yl-6,7-dihydro-5H-benzo[6,7]cyclohepta[1,2-d]pyrimidin-2-yl)-acetamide;

N-(4-piperazin-1-yl-6,7-dihydro-5H-benzo[6,7]cyclohepta[1,2-d]pyrimidin-2-yl)-benzamide;
2-Dimethylamino-N-(4-piperazin-1-yl-6,7-dihydro-5H-benzo[6,7]cyclohepta[1,2-d]pyrimidin-2-yl)-acetamide;
2-Methylamino-N-(4-piperazin-1-yl-6,7-dihydro-5H-benzo[6,7]cyclohepta[1,2-d]pyrimidin-2-yl)-acetamide;
2-Amino-N-(4-piperazin-1-yl-6,7-dihydro-5H-benzo[6,7]cyclohepta[1,2-d]pyrimidin-2-yl)-acetamide;
1-Methyl-3-(4-piperazin-1-yl-6,7-dihydro-5H-benzo[6,7]cyclohepta[1,2-d]pyrimidin-2-yl)-urea;
4-Amino-N-(4-piperazin-1-yl-6,7-dihydro-5H-benzo[6,7]cyclohepta[1,2-d]pyrimidin-2-yl)-butyramide;
3-Amino-N-(4-piperazin-1-yl-6,7-dihydro-5H-benzo[6,7]cyclohepta[1,2-d]pyrimidin-2-yl)-propionamide;
4-[1,4,7]Triazonan-1-yl-6,7-dihydro-5H-benzo[6,7]cyclohepta[1,2-d]pyrimidin-2-ylamine;
N,N-Dimethyl-N'-(4-piperazin-1-yl-6,7-dihydro-5H-benzo[6,7]cyclohepta[1,2-d]pyrimidin-2-yl)-ethane-1,2-diamine;
4-((R)-3-Methylamino-pyrrolidin-1-yl)-6,7,9,10,11,12-hexahydro-5H-1,3-diaza-benzo[3,4]cyclohepta[1,2-b]naphthalen-2-ylamine;
4-piperazin-1-yl-6,7,9,10,11,12-hexahydro-5H-1,3-diaza-benzo[3,4]cyclohepta[1,2-b]naphthalen-2-ylamine;
2,4-Dipiperazin-1-yl-6,7-dihydro-5H-benzo[6,7]cyclohepta[1,2-d]pyrimidine;
4-(4-Dimethylamino-piperidin-1-yl)-6,7-dihydro-5H-benzo[6,7]cyclohepta[1,2-d]pyrimidin-2-ylamine;
4-[1,4]Diazepan-1-yl-6,7-dihydro-5H-benzo[6,7]cyclohepta[1,2-d]pyrimidin-2-ylamine;
4-piperazin-1-yl-6,7-dihydro-5H-benzo[6,7]cyclohepta[1,2-d]pyrimidine;
Methyl-(4-piperazin-1-yl-6,7-dihydro-5H-benzo[6,7]cyclohepta[1,2-d]pyrimidin-2-yl)-amine;
4-(3-(R)-Methylamino-pyrrolidin-1-yl)-6,7-dihydro-5H-benzo[6,7]cyclohepta[1,2-d]pyrimidine;
[1-(6,7-Dihydro-5H-benzo[6,7]cyclohepta[1,2-d]pyrimidin-4-yl)-azetidin-3-yl]-amine;
8,10-Dimethyl-4-piperazin-1-yl-6,7-dihydro-5H-benzo[6,7]cyclohepta[1,2-d]pyrimidin-2-ylamine;
(2-Amino-4-piperazin-1-yl-6,7-dihydro-5H-benzo[6,7]cyclohepta[1,2-d]pyrimidin-10-yl)-methyl-carbamic acid methyl ester;
10-N-Methyl-4-piperazin-1-yl-6,7-dihydro-5H-benzo[6,7]cyclohepta[1,2-d]pyrimidine-2,10-diamine;
(2-Amino-4-octahydro-pyrrolo[3,4-b]pyridin-6-yl-6,7-dihydro-5H-benzo[6,7]cyclohepta[1,2-d]pyrimidin-10-yl)-methyl-carbamic acid methyl ester;
10-N-methyl-4-[(4aR,7aR)-octahydro-6H-pyrrolo[3,4-b]pyridin-6-yl]-6,7-dihydro-5H-benzo[6,7]cyclohepta[1,2-d]pyrimidine-2,10-diamine;
N-(2-Amino-4-piperazin-1-yl-6,7-dihydro-5H-benzo[6,7]cyclohepta[1,2-d]pyrimidin-11-yl)-acetamide;
4-((3aR,6aR)-1-Methyl-hexahydro-pyrrolo[3,4-b]pyrrol-5-yl)-6,7-dihydro-5H-benzo[6,7]cyclohepta[1,2-d]pyrimidin-2-ylamine;
4-((1S,4S)-2,5-Diazabicyclo[2.2.1]hept-2-yl)-6,7-dihydro-5H-benzo[6,7]cyclohepta[1,2-d]pyrimidin-2-ylamine;
4-((3aR,6aR)-Hexahydropyrrolo[3,4-b]pyrrol-1-yl)-6,7-dihydro-5H-benzo[6,7]cyclohepta[1,2-d]pyrimidin-2-ylamine;
4-(Hexahydropyrrolo[3,4-c]pyrrol-2-yl)-6,7-dihydro-5H-benzo[6,7]cyclohepta[1,2-d]pyrimidin-2-yl-amine;
4-Octahydro-6H-pyrrolo[3,4-b]pyridin-6-yl-6,7-dihydro-5H-benzo[6,7]cyclohepta[1,2-d]pyrimidin-2-amine;
4-(2,8-Diazaspiro[4.5]dec-8-yl)-6,7-dihydro-5H-benzo[6,7]cyclohepta[1,2-d]pyrimidin-2-amine;
4-(1,9-Diazaspiro[5.5]undec-9-yl)-6,7-dihydro-5H-benzo[6,7]cyclohepta[1,2-d]pyrimidin-2-ylamine;
4-(2,5-Diazaspiro[3.5]non-2-yl)-6,7-dihydro-5H-benzo[6,7]cyclohepta[1,2-d]pyrimidin-2-ylamine;
4-(Octahydropyrrolo[3,4-c]pyridin-2-yl)-6,7-dihydro-5H-benzo[6,7]cyclohepta[1,2-d]pyrimidin-2-ylamine;
4-(Octahydropyrrolo[1,2-a]pyrazin-2-yl)-6,7-dihydro-5H-benzo[6,7]cyclohepta[1,2-d]pyrimidin-2-ylamine;
4-(3,6-Diazabicyclo[3.2.1]oct-6-yl)-6,7-dihydro-5H-benzo[6,7]cyclohepta[1,2-d]pyrimidin-2-ylamine;
4-(2,6-Diazabicyclo[3.2.1]oct-2-yl)-6,7-dihydro-5H-benzo[6,7]cyclohepta[1,2-d]pyrimidin-2-ylamine;
4-(5-Methyl-octahydro-pyrrolo[3,4-c]pyridin-2-yl)-6,7-dihydro-5H-benzo[6,7]cyclohepta[1,2-d]pyrimidin-2-ylamine;
4-(3-Methyl-3,6-diaza-bicyclo[3.2.1]oct-6-yl)-6,7-dihydro-5H-benzo[6,7]cyclohepta[1,2-d]pyrimidin-2-ylamine;
6-(2-Pyridin-3-ylmethylamino-6,7-dihydro-5H-benzo[6,7]cyclohepta[1,2-d]pyrimidin-4-yl)octahydro-1H-pyrrolo[3,4-b]pyridine;
4-(Octahydro-pyrrolo[3,4-b]pyridin-6-yl)-6,7,9,10,11,12-hexahydro-5H-1,3-diaza-benzo[3,4]cyclohepta[1,2-b]naphthalen-2-ylamine;
10-Fluoro-4-octahydro-6H-pyrrolo[3,4-b]pyridin-6-yl-6,7-dihydro-5H-benzo[6,7]cyclohepta[1,2-d]pyrimidin-2-amine;
(1R,5S)-4-(3,6-Diaza-bicyclo[3.2.0]hept-6-yl)-6,7-dihydro-5H-benzo[6,7]cyclohepta[1,2-d]pyrimidin-2-ylamine;
(3aS,6aS)-4-(Hexahydro-pyrrolo[3,4-b]pyrrol-1-yl)-6,7-dihydro-5H-benzo[6,7]cyclohepta[1,2-d]pyrimidin-2-ylamine;
(1S,5S)-4-(3,6-Diaza-bicyclo[3.2.0]hept-3-yl)-6,7-dihydro-5H-benzo[6,7]cyclohepta[1,2-d]pyrimidin-2-ylamine;
6-(2-(1H-imidazol-4-yl)ethylamino-6,7-dihydro-5H-benzo[6,7]cyclohepta[1,2-d]pyrimidin-4-yl)octahydro-1H-pyrrolo[3,4-b]pyridine;
4-(Octahydro-pyrrolo[3,4-b]pyridin-6-yl)-6,7-dihydro-5H-benzo[6,7]cyclohepta[1,2-d]pyrimidine-2-carboxylic acid methyl ester;
4-(Octahydro-pyrrolo[3,4-b]pyridin-6-yl)-6,7-dihydro-5H-benzo[6,7]cyclohepta[1,2-d]pyrimidine-2-carboxylic acid;
4-piperazin-1-yl-5,6,7,8-tetrahydro-1,3-diaza-dibenzo[a,c]cycloocten-2-ylamine;
4-[(3R)-3-(Methylamino)pyrrolidin-1-yl]-5,6,7,8-tetrahydrobenzo[7,8]cycloocta[1,2-d]pyrimidin-2-amine;

4-[(3R)-3-Aminopyrrolidin-1-yl]-5,6,7,8-tetrahydrobenzo[7,8]cycloocta[1,2-d]pyrimidin-2-amine;
4-[(3S)-3-Aminopyrrolidin-1-yl]-5,6,7,8-tetrahydrobenzo[7,8]cycloocta[1,2-d]pyrimidin-2-amine;
4-(3-Aminoazetidin-1-yl)-5,6,7,8-tetrahydrobenzo[7,8]cycloocta[1,2-d]pyrimidin-2-amine;
4-[(3aR,6aR)-Hexahydropyrrolo[3,4-b]pyrrol-1(2H)-yl]-5,6,7,8-tetrahydrobenzo[7,8]cycloocta[1,2-d]pyrimidin-2-amine;
4-piperazin-1-yl-6,7,8,9-tetrahydro-5H-1,3-diaza-dibenzo[a,c]cyclononen-2-ylamine;
4-(3-(R)-Methylamino-pyrrolidin-1-yl)-6,7,8,9-tetrahydro-5H-1,3-diaza-dibenzo[a,c]cyclononen-2-ylamine;
4-((R)-3-Amino-pyrrolidin-1-yl)-6,7,8,9-tetrahydro-5H-1,3-diaza-dibenzo[a,c]cyclononen-2-ylamine;
4-((S)-3-Amino-pyrrolidin-1-yl)-6,7,8,9-tetrahydro-5H-1,3-diaza-dibenzo[a,c]cyclononen-2-ylamine;
4-(3-Methylamino-azetidin-1-yl)-6,7,8,9-tetrahydro-5H-1,3-diaza-dibenzo[a,c]cyclononen-2-ylamine;
4-((3aS,6aS)-Hexahydro-pyrrolo[3,4-b]pyrrol-1-yl)-6,7,8,9-tetrahydro-5H-1,3-diaza-dibenzo[a,c]cyclononen-2-ylamine; and
4-((1S,4S)-2,5-Diaza-bicyclo[2.2.1]hept-2-yl)-6,7,8,9-tetrahydro-5H-1,3-diaza-dibenzo[a,c]cyclononen-2-ylamine.

17. The method of claim 1, wherein the compound is selected from
4-((S)-Pyrrolidin-3-yloxy)-6,7-dihydro-5H-benzo[6,7]cyclohepta[1,2-d]pyrimidin-2-ylamine;
4-((S)-1-Methyl-pyrrolidin-3-yloxy)-6,7-dihydro-5H-benzo[6,7]cyclohepta[1,2-d]pyrimidin-2-ylamine;
4-(1-Methyl-piperidin-4-yloxy)-6,7-dihydro-5H-benzo[6,7]cyclohepta[1,2-d]pyrimidin-2-ylamine;
4-(Piperidin-4-yloxy)-6,7-dihydro-5H-benzo[6,7]cyclohepta[1,2-d]pyrimidin-2-ylamine;
4-(1-Methyl-piperidin-3-yloxy)-6,7-dihydro-5H-benzo[6,7]cyclohepta[1,2-d]pyrimidin-2-ylamine;
4-(2-Dimethylamino-ethoxy)-6,7-dihydro-5H-benzo[6,7]cyclohepta[1,2-d]pyrimidin-2-ylamine; and
4-((R)-1-Methyl-pyrrolidin-3-yloxy)-6,7-dihydro-5H-benzo[6,7]cyclohepta[1,2-d]pyrimidin-2-ylamine.

\* \* \* \* \*